US012083115B2

(12) United States Patent
Crawford et al.

(10) Patent No.: US 12,083,115 B2
(45) Date of Patent: Sep. 10, 2024

(54) METHODS FOR TREATING NEUROLOGICAL SYMPTOMS ASSOCIATED WITH LYSOSOMAL STORAGE DISEASES

(71) Applicant: Genzyme Corporation, Cambridge, MA (US)

(72) Inventors: Nigel Patrick Somerville Crawford, Tewksbury, NJ (US); Tanya Zaremba Fischer, Newton, MA (US)

(73) Assignee: Genzyme Corporation, Cambridge, MA (US)

( * ) Notice: Subject to any disclaimer, the term of this patent is extended or adjusted under 35 U.S.C. 154(b) by 165 days.

(21) Appl. No.: 17/166,863

(22) Filed: Feb. 3, 2021

(65) Prior Publication Data

US 2021/0251982 A1  Aug. 19, 2021

Related U.S. Application Data

(60) Provisional application No. 63/072,714, filed on Aug. 31, 2020, provisional application No. 63/029,154, filed on May 22, 2020, provisional application No. 62/969,568, filed on Feb. 3, 2020.

(51) Int. Cl.
| | |
|---|---|
| *A61B 5/055* | (2006.01) |
| *A61K 31/439* | (2006.01) |
| *A61K 31/4748* | (2006.01) |
| *A61K 38/47* | (2006.01) |
| *A61P 3/06* | (2006.01) |
| *A61P 25/00* | (2006.01) |

(52) U.S. Cl.
CPC .......... *A61K 31/4748* (2013.01); *A61B 5/055* (2013.01); *A61K 31/439* (2013.01); *A61K 38/47* (2013.01); *A61P 3/06* (2018.01); *A61P 25/00* (2018.01); *C12Y 302/01045* (2013.01)

(58) Field of Classification Search
CPC .............................. A61K 31/439; A61P 25/00
See application file for complete search history.

(56) References Cited

U.S. PATENT DOCUMENTS

| | | |
|---|---|---|
| 3,119,742 A | 1/1964 | Heimlich et al. |
| 3,492,397 A | 1/1970 | David et al. |
| 3,538,214 A | 11/1970 | Gerald et al. |
| 3,749,787 A | 7/1973 | Hepworth et al. |
| 4,060,598 A | 11/1977 | Groppenbacher et al. |
| 4,173,626 A | 11/1979 | Dempski et al. |
| 4,593,034 A | 6/1986 | Munson et al. |
| 4,983,600 A | 1/1991 | Ward et al. |
| 5,025,022 A | 6/1991 | Naylor et al. |
| 5,106,851 A | 4/1992 | Turconi et al. |
| 5,236,838 A | 8/1993 | Rasmussen et al. |
| 5,242,929 A | 9/1993 | Varasi et al. |
| 5,272,071 A | 12/1993 | Chappel et al. |
| 5,549,892 A | 8/1996 | Friedman et al. |
| 5,668,144 A | 9/1997 | Sabb et al. |
| 5,968,502 A | 10/1999 | Treco et al. |
| 5,998,429 A | 12/1999 | Macor et al. |
| 6,066,626 A | 5/2000 | Yew et al. |
| 6,124,354 A | 9/2000 | Akerblom et al. |
| 6,468,998 B1 | 10/2002 | Kuroita |
| 6,492,386 B2 | 12/2002 | Myers et al. |
| 6,599,916 B2 | 7/2003 | Myers et al. |
| 6,780,861 B2 | 8/2004 | Nozulak |
| 6,916,828 B2 | 7/2005 | Farrerons Gallemi et al. |
| 6,953,855 B2 | 10/2005 | Mazurov et al. |
| 6,987,106 B1 | 1/2006 | Gallet et al. |
| 7,115,629 B2 | 10/2006 | Farrerons Gallemi et al. |
| 7,138,410 B2 | 11/2006 | Luithe et al. |
| 7,273,872 B2 | 9/2007 | Tracey et al. |
| 7,332,524 B2 | 2/2008 | Linders et al. |
| 7,435,742 B2 | 10/2008 | Prat Quinones et al. |
| 7,776,879 B2 | 8/2010 | Buil Albero et al. |
| 7,985,760 B2 | 7/2011 | Ali et al. |
| 8,003,617 B2 | 8/2011 | Cheng et al. |
| 8,039,483 B2 | 10/2011 | Amari et al. |
| 8,252,789 B2 | 8/2012 | Lingwood et al. |
| 8,349,319 B2 | 1/2013 | Schuchman et al. |
| 8,367,696 B2 | 2/2013 | Nagashima et al. |
| 8,389,517 B2 | 3/2013 | Ibraghimov et al. |
| 8,729,075 B2 | 5/2014 | Ibraghimov-Beskrovnaya et al. |

(Continued)

FOREIGN PATENT DOCUMENTS

| | | |
|---|---|---|
| CA | 2066696 | 3/1991 |
| CA | 2182568 | 8/1995 |

(Continued)

OTHER PUBLICATIONS

Aerts, et al., "Elevated Globotriaosylsphingosine is a Hallmark of Fabry Disease," PNAS USA, 105: 2812-2817 (2008).

Alam, et al., "Glucosylceramide synthase inhibitors differentially affect expression of glycosphingolipds," Glycobiology, 25(4): 351-356 (2015).

Barton, et al., "Replacement Therapy for Inherited Enzyme Deficiency-Macrophage-targeted Glucocerebrosidase for Gaucher's Disease," New England Journal of Medicine, 324: 1464-1470 (1991).

Beniaminovitz, et al., "Prevention of Rejection in Cardiac Transplantation by Blockade of the Interleukin-2 Receptor with a Monoclonal Antibody," New England Journal of Medicine, 342: 613-619 (2000).

(Continued)

*Primary Examiner* — Amanda L. Aguirre
(74) *Attorney, Agent, or Firm* — Hoxie & Associates LLC

(57) ABSTRACT

Methods are provided for treating or preventing neurological symptoms and disorders which are associated with, e.g., lysosomal storage diseases. The methods include enhancing neuronal connectivity within the brain of a subject, increasing brain tissue volume, or preventing or delaying loss of brain tissue volume in a subject. Also provided are methods for monitoring the progression or regression of a neurological disorder, or assessing the onset of a neurological disorder, associated with a lysosomal storage disease, in which brain tissue volume of the subject is measured.

37 Claims, 1 Drawing Sheet

(56) References Cited

U.S. PATENT DOCUMENTS

| | | | |
|---|---|---|---|
| 8,791,123 B2 | 7/2014 | Allen et al. | |
| 8,993,556 B2 | 3/2015 | Brasca et al. | |
| 9,108,975 B2 | 8/2015 | Tamura et al. | |
| 9,126,993 B2 | 9/2015 | Bourque et al. | |
| 9,139,580 B2 | 9/2015 | Bourque et al. | |
| 9,440,976 B2 | 9/2016 | Dyke et al. | |
| 9,481,671 B2 | 11/2016 | Ibraghimov-Beskrovnaya et al. | |
| 9,518,049 B2 | 12/2016 | Siegel et al. | |
| 9,655,946 B2 | 5/2017 | Alexiou et al. | |
| 9,682,975 B2 | 6/2017 | Siegel et al. | |
| 9,845,327 B2 | 12/2017 | Krainc et al. | |
| 10,065,949 B2 | 9/2018 | Siegel et al. | |
| 10,604,518 B2 | 3/2020 | Siegel et al. | |
| 10,954,230 B2 | 3/2021 | Siegel et al. | |
| 11,008,316 B2 | 5/2021 | Bourque et al. | |
| 2002/0177591 A1 | 11/2002 | O'Donnell et al. | |
| 2004/0002513 A1 | 1/2004 | Mazurov et al. | |
| 2005/0239774 A1 | 10/2005 | Ernst et al. | |
| 2006/0058349 A1 | 3/2006 | Ali et al. | |
| 2007/0213350 A1 | 9/2007 | Tracey et al. | |
| 2007/0249588 A1 | 10/2007 | Ernst et al. | |
| 2008/0234324 A1 | 9/2008 | Orchard et al. | |
| 2009/0131470 A1 | 5/2009 | Walmsley et al. | |
| 2009/0163500 A1 | 6/2009 | Lingwood et al. | |
| 2009/0017847 A1 | 7/2009 | Lee et al. | |
| 2009/0318491 A1 | 12/2009 | Picciotto et al. | |
| 2010/0113517 A1 | 5/2010 | Palling | |
| 2010/0190761 A1 | 7/2010 | Ogawa et al. | |
| 2011/0052559 A1 | 3/2011 | Schuchman et al. | |
| 2012/0157464 A1 | 6/2012 | Feurbach et al. | |
| 2014/0228575 A1 | 8/2014 | Bellunt et al. | |
| 2014/0255381 A1 | 9/2014 | Bourque et al. | |
| 2014/0371460 A1 | 12/2014 | Bourque et al. | |
| 2015/0210681 A1 | 7/2015 | Bourque et al. | |
| 2016/0039805 A1 | 2/2016 | Siegel et al. | |
| 2016/0039806 A1 | 2/2016 | Siegel et al. | |
| 2016/0207933 A1 | 7/2016 | Bourque et al. | |
| 2016/0361301 A1 | 12/2016 | Leonard et al. | |
| 2017/0334903 A1 | 11/2017 | Siegel et al. | |
| 2018/0036295 A1 | 2/2018 | Cheng et al. | |
| 2018/0065957 A1 | 3/2018 | Bourque et al. | |
| 2019/0030082 A1* | 1/2019 | Bae | A61K 9/00 |
| 2019/0031652 A1 | 1/2019 | Siegel et al. | |
| 2020/0048266 A1 | 2/2020 | Bourque et al. | |
| 2020/0181137 A1 | 6/2020 | Siegel et al. | |
| 2021/0251982 A1 | 8/2021 | Crawford et al. | |
| 2021/0261557 A1 | 8/2021 | Bourque et al. | |
| 2022/0016092 A1 | 1/2022 | Crawford et al. | |
| 2022/0110922 A1 | 4/2022 | Ibraghimov-Beskrovnaya et al. | |
| 2022/0193059 A1* | 6/2022 | Hayden | A61K 31/451 |

FOREIGN PATENT DOCUMENTS

| | | | |
|---|---|---|---|
| CA | 2398754 | 8/2001 | |
| DE | 1768808 | 1/1972 | |
| DE | 1326510 | 2/1995 | |
| EP | 0505778 | 10/1995 | |
| EP | 0382687 | 12/1995 | |
| EP | 0 747 355 | 12/1996 | |
| EP | 1300407 | 4/2003 | |
| EP | 2119716 | 11/2009 | |
| EP | 2154136 | 2/2010 | |
| GB | 725228 | 3/1955 | |
| JP | H-08198751 | 8/1996 | |
| JP | 2002302490 | 10/2002 | |
| JP | 2003267977 | 9/2003 | |
| WO | WO 1995/021820 | 8/1995 | |
| WO | WO 98/04517 | 2/1998 | |
| WO | WO 2000/026186 | 5/2000 | |
| WO | WO 2001/085727 | 11/2001 | |
| WO | WO 2002/015662 | 2/2002 | |
| WO | WO 2002/016356 | 2/2002 | |
| WO | WO 2003/078431 | 9/2003 | |
| WO | WO 2004/000840 | 12/2003 | |
| WO | WO 2004/007453 | 1/2004 | |
| WO | WO 2004/016617 | 2/2004 | |
| WO | WO 2004/011430 | 5/2004 | |
| WO | WO 2004/052365 | 6/2004 | |
| WO | WO 2004/056745 | 7/2004 | |
| WO | WO 2005/061510 | 7/2005 | |
| WO | WO 2005/068426 | 7/2005 | |
| WO | WO 2005/073183 | 8/2005 | |
| WO | WO 2006/053043 | 5/2006 | |
| WO | WO 2006/134318 | 12/2006 | |
| WO | WO 2007/038367 | 4/2007 | |
| WO | WO 2007/083978 | 7/2007 | |
| WO | WO 2007/100430 | 9/2007 | |
| WO | WO 2008/156721 | 12/2008 | |
| WO | WO 2010/015324 | 2/2010 | |
| WO | WO 2010/091104 | 8/2010 | |
| WO | WO 2010/091164 | 8/2010 | |
| WO | WO 2010/121963 | 10/2010 | |
| WO | WO 2011/006074 | 1/2011 | |
| WO | WO 2011/073263 | 6/2011 | |
| WO | WO 2012/129084 | 9/2012 | |
| WO | WO-2012129084 A2 * | 9/2012 | ........... A61K 31/439 |
| WO | WO 2014/041425 | 3/2014 | |
| WO | WO-2014152215 A1 * | 9/2014 | ............ A61P 25/00 |

OTHER PUBLICATIONS

Brenkert, et al., "Synthesis of Galactosyl Ceramide and Glucosyl Ceramide by Rat Brain: Assay Procedures and Changes with Age," Brain Research, 36: 183-193 (1971).

Cabrera-Salazar, et al., "Intracerebroventricular Delivery of Glucocerebrosidase Reduces Substrates and Increases Lifespan in a Mouse Model of Neuronopathic Gaucher Disease," Experimental Neurology, 225: 436-444 (2010).

Chirmule, et al., "Readministration of Adenovirus Vector in Non-human Primate Lungs by Blockade of CD40-CD40 Ligand Interactions," J. Virol., 74: 3345-3352 (2000).

Conradi, et al., "Late-infantile Gaucher Disease in a Child with Myoclonus and Bulbar Signs: Neuropathological and Neurochemical Findings," Acta Neuropathologica, 82: 152-157 (1991).

Czartoryska, et al., "Changes in Serum Chitotriosidase Activity with Cessation of Replacement Enzyme (Cerebrosidase) Administration in Gaucher Disease," Clin. Biochem., 33: 147-149 (2000).

Czartoryska, et al., "Serum Chitotriosidase Activity in Gaucher Patients on Enzyme Replacement Therapy (ERT)," Clin. Biochem., 31: 417-420 (1998).

Den Tandt, et al., "Marked Increase of Methylumbelliferyl-tetra-N-acetylchitotetraoside Hydrolase Activity in Plasma from Gaucher Disease Patients," J. Inherit. Metab. Dis., 19: 344-350 (1996).

El Alwani, et al., "Regulation of the Sphingolipidsignaling Pathways in the Growing and Hypoxic Rat Heart," Prostaglandins & Other Lipid Mediators, 78(1-4): 249-263 (2005).

Enquist, et al., "Murine Models of Acute Neuronopathic Gaucher Disease," PNAS, 104: 17483-17488 (2007).

European Search Report for EP 2685986, "Glucosylceramide Synthase Inhibitors," mailed Feb. 4, 2015.

Fishwild, et al., "Differential Effects of Administration of a Human Anti-CD4 Monoclonal Antibody, HM6G, in Nonhuman Primates," Clin. Immunol., 92: 138-152 (1999).

Gaziev, et al., "Chronic graft-versus-host disease: is there an alternative to the conventional treatment?" Bone Marrow Transplant, 25: 689-696 (2000).

Giri, et al., "Krabbe Disease: Psychosine-mediated Activation of Phospholipase A2 in Oligodendrocyte Cell Death," Journal of Lipid Research, 47: 1478-1492 (2006).

Gummert, et al., "Newer Immunosuppressive Drugs: A Review," J. Am. Soc. Nephrol., 10: 1366-1380 (1999).

Guo, et al., "Elevated Plasma Chiotriosidase Activity in Various Lysosomal Storage Disorders," J. Inherit. Metab. Dis., 18: 717-722 (1995).

Hollak, et al., "Marked Elevation of Plasma Chitotriosidase Activity: A Novel Hallmark of Gaucher Disease," J. Clin. Invest., 93: 1288-1292 (1994).

(56) References Cited

OTHER PUBLICATIONS

Ida, et al., "Clinical and Genetic Studies of Japanese Homozygotes for the Gaucher Disease L444P Mutation," Human Genetics, 105: 120-126 (1999).
International Search Report for WO 2012/0129084, dated Jul. 2, 2013.
Ito, et al., "Induction of CTL Responses by Simultaneous Administration of Liposomal Peptide Vaccine with Anti-CD40 and Anti-CTLA-4 mAb," J. Immunol., 164: 1230-1235 (2000).
Johnson, et al., "Relationship between drug activity in NCI preclinical in vitro and in vivo models and early clinical trials," British Journal of Cancer, 84(10): 1424-1431 (2001).
Leonard, et al., "Cytokine receptor signaling pathways," J. Allergy Clin. Immunol., 105: 877-888 (2000).
Liu, et al., "Mice with type 2 and 3 Gaucher Disease Point Mutations Generated by a Single Insertion Mutagenesis Procedure (SIMP)," PNAS, 95: 2503-2508 (1998).
Marinova-Mutafchieva, et al., "A Comparative Study into the Mechanisms of Action and Anti-Tumor Necrosis Factor a/Anti-CD4, and Combined Anti-Tumor Necrosis Factor a/Anti-CD4 Treatment in Early Collagen-Induced Arthritis," Arthritis Rheum., 43: 638-644 (2000).
Marks, et al., "Identification of Active Site Residues in Glucosylceramide Synthase," Journal of Biological Chemistry, 276: 26492-26498 (2001).
Marshall, et al., "Substrate Reduction Augments the Efficacy of Enzyme Therapy in a Mouse Model of the Fabry Disease," PLoS One, 53: 15033 (2010).
Natoli Ta., "Inhibition of glucosylceramide accumulation results in effective blockade of polycystic kidney disease in mouse models," Nat Med., 16(7): 788-792 (2010).
Nevins, "Overview of new immunosuppressive therapies," Curr. Opin. Pediatr., 12: 146-150 (2000).
O'Donnell, C.J., et al., "Synthesis and SAR Studies of 1,4-diazibicyclo[3.2.2]nonane phenyl carbamates—Subtype Selective, High Affinity α7 Nicotinic Acetylcholine Receptor Agonists," Bioorganic and Medicinal Chemistry Letters, 19: 4747-4751 (2009).
Orvisky, et al., "Glucosylsphingosine Accumulation in Mice and Patients with Type 2 Gaucher Disease Begins Early in Gestation," Pediatric Research, 48: 233-237 (2000).
Pastores, et al., "Enzyme Therapy in Gaucher Disease Type 1: Dosage Efficacy and Adverse Effects in 33 Patients Treated for 6 to 24 Months," Blood, 82: 408-416 (1993).
Przepiorka, et al., "A Phase II Study of BTI-322, a Monoclonal Anti-CD2 Antibody, for Treatment of Steroid-Resistant Acute Graft-Versus-Host Disease," Blood, 92: 4066-4071 (1998).
Qi, et al., "Effect of Tacrolimus (FK506) and Sirolimus (Rapamycin) Mono- and Combination Therapy in Prolongation of Renal Allograft Survival in the Monkey," Transplantation, 69: 1275-1283 (2000).
Registry(STN) [online], Oct. 13, 2005 [searched on Oct. 9, 2015] CAS registration No. 8565147-82-6.
Registry(STN) [online], Nov. 4, 2008, CAS registration No. 1070460-12-6.
Shapiro, et al., "Islet Transplantation in Seven Patients with Type 1 Diabetes Mellitus Using a Glucocorticoid-Free Immunosuppressive Regimen," New England Journal of Medicine, 343: 230-238 (2000).
Shayman, JA., "Targeting Glucosylceramide Synthesis in the Treatment of Rare and Common Renal Disease," Semin Nephrol., 38(2):183-192, (2018).
Sun, et al., "Neuronopathic Gaucher Disease in the Mouse Viable Combined Selective Saposin C Deficiency and Mutant Glucocerebrosidase (V394L) Mice with Glucosylsphingosine and Glucosylceramide Accumulation and Progressive Neurological Deficits," Hum. Mol. Genet., 19: 1088-1097 (2010).
Turzanski, et al., "P-Glycoprotein is Implicated in the Inhibition of Ceramide-induced Apoptosis in TF-1 Acute Myeloid Leukemia Cells by Modulation of the Glucosylceramide Synthase Pathway," Experimental Hematology, 33(1): 62-72 (2005).

Wolff, et al., "Some consideration for prodrug design," Burger's Medicinal Chemistry and Drug Discovery, Fifth Edition, 1: 975-977 (1995).
Wong, Manfred E., "Neuropathology Provides Clues to the Pathophysiology of Gaucher Disease," Molecular Genetics and Metabolism, 82: 192-207 (2004).
Yamashita, et al., "A vital role for glycosphingolipid synthesis during development and differentiation," Proc. Natl. Acad. Sci., 99(16): 9142-9147 (1999).
Baosheng Fu, et al. (Eds.), "Highlights and Difficult Cases in Neurology," Science and Technology Literature Press, 1st edition, Feb. 2017, p. 53 (Partial English Translation).
Berard J.L., et al., "A Review of Interleukin-2 Receptor Antagonists in Solid Organ Transplantation," Pharmacotherapy, 1999, vol. 19 (10), pp. 1127-1137.
Chinese Search Report for CN 202080025346.0, mailed May 25, 2023, English Translation.
Davidson et al., The Neuronal Ceroid Lipofuscinosis, Clinical Features and Molecular Basis of Disease, Lysosomal Storage Disorders, {2007), pp. 371-388. Springer, New York, U.S.A.
Dodelson De Kremer R., et al., "[Plasma Chitotriosidase Activity in Argentinian Patients with Gaucher Disease, Various Lysosomal Diseases and Other Inherited Metabolic Disorders]," Medicina, 1997, vol. 57 (6), pp. 677-684.
Dörwald, F. Zaragoza. Side Reactions in Organic Synthesis: A Guide to Successful Synthesis Design, Weinheim: Wiley-VCH Verlag GmbH & Co. KGaA, 2005, Preface.
Eckhoff D.E., et al., "The Safety and Efficacy of a Two-Dose Daclizumab (Zenapax) Induction Therapy in Liver Transplant Recipients," Transplantation, 2000, vol. 69 (9), pp. 1867-1872.
Ekberg H., et al., "Daclizumab Prevents Acute Rejection and Improves Patient Survival Post Transplantation: 1 Year Pooled Analysis," Transplant International, 2000, vol. 13 (2), pp. 151-159.
Goker-Alpan O., et al., "Phenotypic Continuum in Neuronopathic Gaucher Disease: An Intermediate Phenotype Between Type 2 and Type 3," The Journal of Pediatrics, 2003, vol. 143 (2), pp. 273-276.
Grabowski G.A., et al., "Enzyme Therapy in Type 1 Gaucher Disease: Comparative Efficacy of Mannose-Terminated Glucocerebrosidase from Natural and Recombinant Sources," Annals of Internal Medicine, 1995, vol. 122 1), pp. 33-39.
Graler et al., Lysophospholipids and their G protein-coupled receplorsin inflammation and immunity, Molecular and Cell Biology of Lipids 1582: 168-174 (2002).
Henry M.L., et al., "Cyclosporine and Tacrolimus (FK506): A Comparison of Efficacy and Safety Profiles," Clinical Transplantation, 1999, vol. 13 (3), pp. 209-220.
Hers H.G., "Inborn Lysosomal Diseases," Gastroenterology, 1965, vol. 48, pp. 625-633.
Hong J.C., et al., "Immunosuppressive Agents in Organ Transplantation: Past, Present, and Future," Seminars in Nephrology, 2000, vol. 20 (2), pp. 108-125.
Ideguchi M., et al., "Local Adenovirus-Mediated CTLA4-Immunoglobulin Expression Suppresses the Immune Responses to Adenovirus Vectors in the Brain," Neuroscience, 2000, vol. 95 (1), pp. 217-226.
Mazurov A., et al., "2-{Arylmethyl)-3-Substituted Quinuclidines as Selective Alpha 7 Nicotinic Receptor Ligands," Bioorganic & Medicinal Chemistry Letters, 2005, vol. 15 (8), pp. 2073-2077.
Mehta, et al., "Fabry disease: a review of current management strategies," 2010, vol. 103, pp. 641-659.
Mistry P.K., et al., "A Practical Approach to Diagnosis and Management of Gaucher's Disease," Baillieres Clinical Haematology, 1997, vol. 10 (4), pp. 817-838.
Morales L.E., "Gaucher's Disease: A Review," Annals of Pharmacotherapy, 1996, vol. 30 (4), pp. 381-388.
Oberholzer A., et al., "Cytokine Signaling-Regulation of the Immune Response in Normal and Critically ill States," Critical Care Medicine, 2000, vol. 28 { Suppl 4), pp. N3-N12.
Pelled et al., The increased sensitivity of neurons with elevated glucocerebroside to neurotoxic agents can be reversed by imiglucerase, Journal of Inherited Metabolic Disease 23: 175-184 (2000).
Ponticelli C., et al., "Promising New Agents in the Prevention of Transplant Rejection," Drugs in Rand D, 1999, vol. 1 (1), pp. 55-60.

(56) References Cited

OTHER PUBLICATIONS

Potter M.A., et al., "Review—The Use of Immunosuppressive Agents to Prevent Neutralizing Antibodies against a Transgene Product," Annals of the New York Academy of Sciences, 1999, vol. 875, pp. 159-174.
Rosenthal D.I., et al., "Enzyme Replacement Therapy for Gaucher Disease: Skeletal Responses to Macrophage-Targeted Glucocerebrosidase," Pediatrics, 1995, vol. 96 (4 Pt 1), pp. 629-637.
Rubinstein M., et al., "Recent Advances in Cytokines, Cytokine Receptors and Signal Transduction," Cytokine & Growth Factor Reviews, 1998, vol. 9 (2), pp. 175-181.
Salsano, et al., "Vertical supranuclear gaze palsy in Niemann-Pick type C disease," Neurol Sci, 2012, vol. 33, pp. 1225-1232.
Schueler et al., Toxicity of glucosylsphingosine (glucopsychosine) to cultured neuronalcells: a model system for assessing neuronal damage in Gaucher disease type 2 and 3, Neurobiology of Disease 14: 595-601 (2003).
Slavik J.M., et al., "CD28/CTLA-4 and CD80/CD86 Families: Signaling and Function," Immunologic Research, 1999, vol. 19 (1), pp. 1-24.
Weidong, Zhou (Ed.), "Cognitive Neurology," Military Medical Sciences Press, 1st edition, Aug. 2013, p. 227 (Partial English Translation).
Weinreb N.J., et al., "Effectiveness of Enzyme Replacement Therapy in 1028 Patients with Type 1 Gaucher Disease after 2 to 5 Years of Treatment: A Report from the Gaucher Registry," The American Journal of Medicine, 2002, vol. 113 (2), pp. 112-119.
Wiseman L.R., et al., "Daclizumab: A Review of its use in the Prevention of Acute Rejection in Renal Transplant Recipients," Drugs, 1999, vol. 58 (6), pp. 1029-1042.
Young E., et al., "Plasma Chitotriosidase Activity in Gaucher Disease Patients Who Have Been Treated either by Bone Marrow Transplantation or by Enzyme Replacement Therapy with Alglucerase," Journal of Inherited Metabolic Disease, 1997, vol. 20 (4), pp. 595-602.
Auray-Blais C., et al., "How Well Does Urinary Lyso-gb3 Function as a Biomarker in Fabry Disease?" Clinica Chimica Acta, 2010, vol. 411 (23-24), pp. 1906-1914.
Bangari, et al., "Progressive Organ Pathology Resembles the Type 2 Later-Onset Phenotype of Fabry Disease," The American Journal of Pathology, 185(3):651-665 (2015).
Banker et al., "B. Prodrugs," Modern Pharmaceutics: Third Edition, Revised and Expanded, p. 596, (1996).
Blandini et al., "Glucocerebrosidase Mutations and Synucleinopathies: Toward a Model of Precision Medicine" Mov Disord 2019; 34: 9-21.
Branco L., et al., "Selective Deletion of Antigen-Specific, Activated T Cells by a Humanized MAB to CO2 { Medi-507) s Mediated by NK Cells," Transplantation, 1999, vol. 68 (10), pp. 1588-1596.
Brat, et al., "Tau-associated Neuropathology in ganglion cell tumours increases with patient age but appears unrelated to ApoE genotype," Neuropathology and Applied Neurobiology, vol. 27 (2001), pp. 197-205.
Bremova-Ertl et al., "Oculomotor and Vestibular Findings in Gaucher Disease Type 3 and Their correlation with neurological Findings" Frontiers in Neurology 2018, vol. 8, pp. 1-19.
Ceravolo R et al., "A review of adverse events linked to dopamine agonists in the treatment of Parkinson's disease" 2016; 15:181-98.
Cerbai et al., Acetylene derivatives with antispastic activity. II. Amino esters of propylpropargylacetic acid, Farrnaco, Edizione Scientifica, 1972, vol. 27(3): 217-234.
Conradi et al., Neuropathology of the Norrbottnian Type of Gaucher Disease, Acta Neuropathologica 65: 99-109(1984).
Cullen, et al., "Acid β-Glucosidase Mutants Linked to Gaucher Disease, Parkinson Disease, and Lewy Body Dementia Alter α-Synuclein Processing" American Neurological Association, 2011, vol. 69, pp. 940-953. DeMaagd et al., "Parkinson's Disease and Its Management" 2015; 40: 504-32.

Demain et al., Enantiomeric purity determination of 3-aminoquinuclidine by diastereomeric derivatization and high-performance liquid chromatographic separation, Journal of Chromatography, vol. 466: 415-420 (1989).
Feuerbach, et al., "JN403, in vitro characterization of a novel nicotinic acetylcholine receptor a7 selective agonist," pp. 61-65 Neuroscience Letters (2007).
Gambarin, F., et al., "When Should Cardiologists Suspect Anderson-Fabry Disease?" The American Journal of Cardiology, 106(10): 1492-1499 (2010).
Gaenslen, A., et al., "The Patient's Perception of Prodromal Symptoms Before the Initial Diagnosis of Parkinson's Disease," Movement Disorders: Official Journal of Movement Disorder Society, 26(4): 653-658, 656 (2011).
Goedert, "Tau Gene Mutations and Their Effects," Movement Disorders, vol. 20 (2005), pp. S45-S52.
Goetz et al., "Movement Disorder Society-Sponsored Revision of the Unified Parkinson's Disease Rating Scale (MDS-UPDRS): Process, Format, and Clinimetric Testing Plan" Mov Disord 2007; 22: 41-7.
Goetz et al., "Movement Disorder Society-Sponsored Revision of the Unified Parkinson's Disease Rating Scale (MDS-UPDRS): Scale Presentation and Clinimetric Testing Results" Mov Disord 2008; 23:2129-70.
Grover S et al., "Psychiatric aspects of Parkinson's disease" J Neurosci Rural Pract 2015; 6: 65-76.
Gura, Trisha, "Systems for identifying new drugs are often faulty," Science 7, 278(5340): 1041-1042 (1997).
He Lin et al. (Eds.), Clinical Genetics (Shanghai Science and Technology Press, $1^{st}$ edition, May 31, 2013), p. 447, left column, paragraph 1, and p. 448, left column, paragraph 2.
He Lin et al. (Eds.), Clinical Genetics (Shanghai Science and Technology Press, $1^{st}$ edition, May 31, 2013), p. 447, left column paragraph 1, and p. 448, left column paragraph 2, English Language Translation.
Hoehn MM, Yahr MD. "Parkinsonism: onset, progression and mortality" Neurology 1967; 17: 427-42.
Hollak, et al., (Expert Opinion Ther. Targets (2007) 11:821-833). (Year: 2007).
Irvine et al. (Mol Med. Jul.-Aug. 2008; 14(7-8): 451-464).
Jordan, V. C. Nature Reviews: Drug Discovery, 2, 2003, pp. 205-213.
Kloe, G., et al., "Surface Plasmon Resonance Biosensor Based Fragment Screening Using Acetylcholine Binding Protein Identifies Ligand Efficiency Hot Spots (LE Hot Spots) by Deconstruction of Nicotinic Acetylcholine Receptor a7 Ligands," Journal of Medicinal Chemistry, 53: 7192-7201 (2010).
Kurlberg G., et al., "Blockade of the B7-CD28 Pathway by CTLA4-1g Counteracts Rejection and Prolongs Survival n Small Bowel Transplantation," Scandinavian Journal of Immunology, 2000, vol. 51 (3), pp. 224-230.
Lee, V., "Mechanisms of Parkinson's Disease Linked to Pathological a-Synuclein: New Targets for Drug Discovery," Elsevier Inc., Neuron 52:33-38 (2006).
Mashkovsky, The Relationship Between the Chemical Structure and Pharmacological Activity of Some Esters of3-Hydroxyquinuclidine (Quinuclidine-3-0L}, Proc. Intern. Pharrnacol. Meeting, 1st, Stockholm, 1961, 1963, vol. 7: 356-366.
Masjedizadeh, et al., "Synthesis of Tritium Labelled (R) and (S)-3-Aminoquinuclidine: A Ubiquitous Component of Serotonin Receptor Lignads, Part 1," Journal of Labelled Compounds and Radiopharmaceuticals (1996).
Marshall, J., et al., "CNS-accessible Inhibitor of Glucosylceramide Synthase for Substrate Reduction Therapy of Neuronpathic Gaucher Disease," Official Journal of the American Society of Gene & Cell Therapy, 2016, vol. 24(6), pp. 1019-1029.
Mazzuli, et al., "Gaucher Disease Glucocerebrosidase and α-Synuclein Form a Bidirectional Pathogenic Loop in Synucleinopathies" Cell, 2011, vol. 146, pp. 37-52.
Migdalska-Richards et al., "The relationship between glucocerebrosidase mutations and Parkinson disease" J Neurochem 2016; 139:77-90.
Mitsui J et al., "Mutations for Gaucher Disease Confer High Susceptibility to Parkinson Disease" Arch Neurol 2009; 66: 571-6.

(56) References Cited

OTHER PUBLICATIONS

Merrill et al., Sphingolipidomics: High-throughput, structure-speciWc,and quantitative analysis of sphingolipids by liquid chromatographytandem mass spectrometry, Methods 36: 207-224 (2005).
Naito, R., et al., "Selective Muscarinic Antagonists. 11.(1) Synthesis and Antimuscarinic Properties of Biphenylylcarbamate Derivatives," Chem. Pharm. Bull., 1998, vol. 46(8), pp. 1286-1294.
Nasreddine et al., "The Montreal Cognitive Assessment, MoCA: A Brief Screening Tool for Mild Cognitive Impairment" *J Am Geriatr Soc* 2005; 53: 695-9.
Nilsson et al., "Accumulation of Glucosylceramide and Glucosylsphingosine (Psychosine) in Cerebrum and Cerebellum in Infantile and Juvenile Gaucher Disease," Journal of Neurochemistry, 1982, vol. 39 (3), pp. 709-718.
Noelker, C., et al., "Glucocerebrosidase deficiency and mitochondrial impairment in experimental Parkinson disease," Journal of the Neurological Sciences, Elsevier, 356(1-2): 129-136 (2015).
Orr, et al., "A Brief Overview of Tauopathy: Causes, Consequences, and Therapeutic Strategies," Trends Pharmacol Sci. (2017) 38(7): pp. 637-648. doi: 10.1016/j .tips.2017 .03 .011.
Palavra, et al., (Neurology Research International (2013) p. 1-8, ID:576091).
Poirier et al., "Gastrointestinal Dysfunctions in Parkinson's Disease: Symptoms and Treatments" *Parkinsons Dis* 2016; 2016: 6762528.
Riboldi et al., "GBA, Gaucher Disease, and Parkinson's Disease: From Genetic to Clinic to New Therapeutic Approaches" *Cells* 2019; 8(4):364.
Ross, C. & Poirier, M., "Protein aggregation and neurodegenerative disease," Nature Medicine 10, S 10-S 17, Abstract (2004).
Ryan E.A., et al., "Clinical Outcomes and Insulin Secretion after Islet Transplantation with the Edmonton Protocol," Diabetes, 2001, vol. 50 (4), pp. pp. 710-719.
Sardi et al., Proc Natl Acad Sci USA 2017; 114: 2699-704.
Sidransky et al., "Multi-center analysis of glucocerebrosidase mutations in Parkinson disease" *N Engl J Med* 2009; 361: 1651-61.
Skorvanek M et al., Mov Disord Clin Pract 2017; 4: 536-544.
Scholl, M., et al., "In Vivo Braak Staging Using 18F-AV1451 Tau PET Imaging," Alzheimer's & Dementia 11(7): Suppl. P4 (Jul. 2015).
Shen, W., et al., "Inhibition of glucosylceramide synthase stimulates autophagy flux in neurons," Journal of Neurochemistry, 129: 884-894 (2014).
"Tauopathy," Standardofcare.com, https://standardofcare.com/tauopathy/ (2022).
Thurberg, et al., "Cardiac Microvascular Pathology in Fabry Disease Evaluation of Endomyocardial Biopsies Before and After Enzyme Replacement Therapy," Circulation, 119(19):2561-2567 (2009).
Thurberg, B., et al., "Monitoring the 3-Year Efficacy of Enzyme Replacement Therapy in Fabry Disease by Repeated Skin Biopsies" The Journal of Investigative Dermatology, 2004, vol. 122, pp. 900-908.
Urbanelli, L., et al., "Therapeutic Approaches for Lysosomal Storage Diseases: A Patent Update," Recent Patents on CNS Drug Discovery, 8(2): 1-19 (2013).
Wiersma, et al., "Untangling the origin and function of granulovacuolar degeneration bodies in neurodegenerative proteinopathies," Acta Neuropathologica Communications vol. 8 (2020) pp. 153.
WO1995021820, Yamanouchi Pharma Co. Ltd., "Novel Carbamate Derivative and Medicinal Composition Containing the Same," Aug. 17, 1995, English language machine translation of abstract, Espacenet, date obtained: Apr. 5, 2019, 2 pages <https : / /worldwide.espacenet.com/publicationDetails/biblio ?CC=WO&NR=95 21820A1&KC=A1&FT=D&ND=3&date=19950817&DB=&locale=en EP>.
WO2000026186, Yoshitomi Pharmaceutical, "Pyrrolidine Compounds and Medicinal Utilization Thereof," May 11, 2000, English language machine translation of abstract, Espacenet, date obtained: Apr. 5, 2019, 2 pages <https : / /worldwide.espacenet.com/ publicationDetails/biblio ?CC=WO&NR=0026186 A1&KC=A1 &FT=D&ND=3&date=20000511&DB=&locale=en EP>.
WO2003078431, Bayer AG, "AZA-Bicyclic N-Biarylamides with Affinity for the Alpha-7 Nicotinic Acetylcholine Receptor," Sep. 25, 2003, English language machine translation of abstract, Espacenet, date obtained: Apr. 5, 2019, 2 pages <https : / /worldwide.espacenet.com/publicationDetails/biblio ?CC=WO&NR=030784 31 A1&KC=A1&FT=D&ND=4&date=20030925&DB=&locale=en EP>.
Wemheuer, W., et al., "Types and Strains: Their Essential Role in Understanding Protein Aggregation in Neurodegenerative Diseases," Frontiers in Aging Neuroscience, 9: 187 (2017).

* cited by examiner

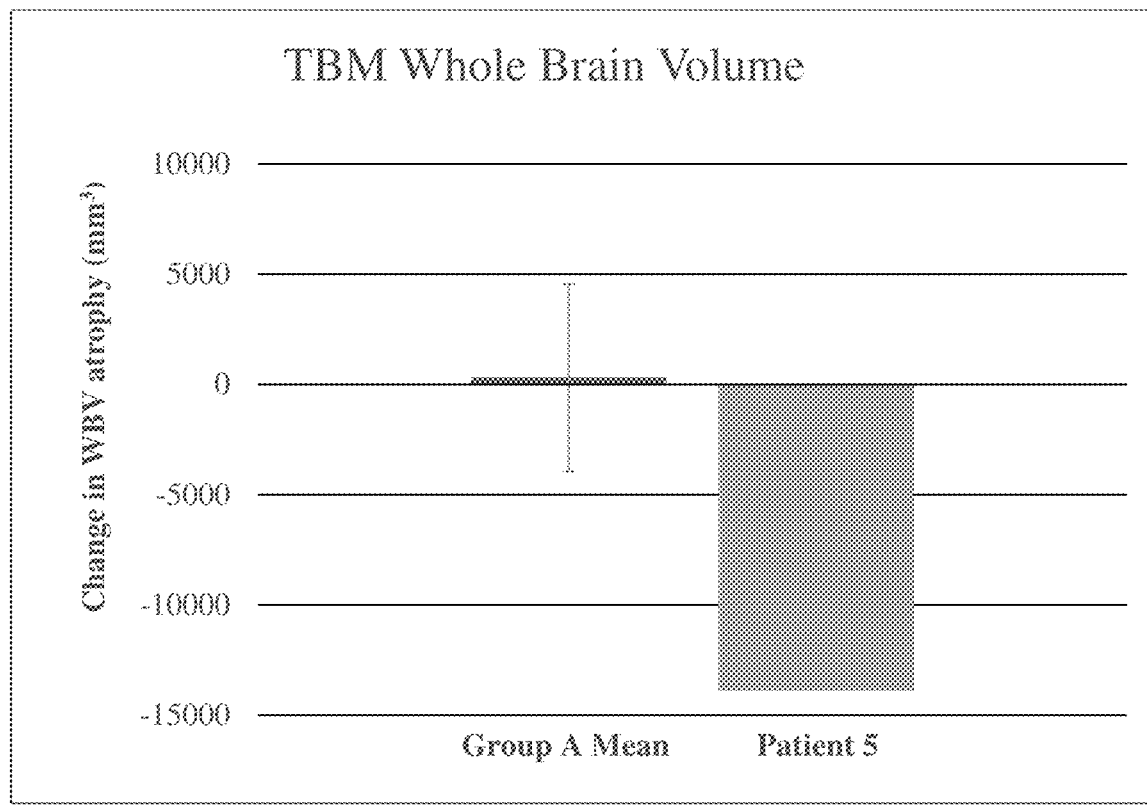

METHODS FOR TREATING NEUROLOGICAL SYMPTOMS ASSOCIATED WITH LYSOSOMAL STORAGE DISEASES

CROSS-REFERENCE TO RELATED APPLICATIONS

This application is a non-provisional application filed under 35 U.S.C. 111(a) which claims priority to, and the benefit of, U.S. Provisional Applications Ser. No. 62/969, 568, filed on Feb. 3, 2020, and Ser. No. 63/029,154, filed on May 22, 2020, and Ser. No. 63/072,714, filed on Aug. 31, 2020, the contents of each of which are hereby incorporated by reference in their entireties.

FIELD

This invention relates to methods for treating or preventing particular symptoms and disorders which are associated with, e.g., lysosomal storage diseases using quinuclidine compounds of formula (I), optionally in combination with enzyme replacement therapy. The methods enhance neuronal connectivity within the brain of a subject, increase brain tissue volume, or prevent or delay loss of brain tissue volume in a subject. The invention also relates to methods for monitoring the progression or regression of a neurological disorder, or assessing the onset of a neurological disorder, associated with a lysosomal storage disease, in which brain tissue volume of the subject is measured.

BACKGROUND

Lysosomal Storage Diseases

Lysosomal storage diseases (LSDs) are a group of about 50 rare inherited metabolic diseases caused by defects in lysosomal function. Generally, patients with an LSD accumulate harmful levels of a substrate (i.e., material stored) in lysosomes due to a deficiency or defect in an enzyme responsible for metabolizing the substrate, or due to a deficiency in an enzymatic activator required for proper enzymatic function. Most LSDs are caused by a single enzymatic defect or deficiency, usually for an enzyme involved in the metabolism of lipids or glycoproteins. Some of the more common LSDs include Gaucher disease, Fabry disease, and Niemann-Pick disease (type C). Gaucher, Fabry, and Niemann-Pick are examples of sphingolipidoses. Each of these diseases is associated with a constellation of symptoms which are directly or indirectly caused by the underlying genetic defects. As a result, it is often difficult to predict which symptoms or disorders associated with each disease can be effectively treated with different treatment methods. Symptoms which are common across several LSDs include alterations in saccadic eye movements, cognitive dysfunction, and gait disorders, such as ataxia. These symptoms are particularly common in Gaucher disease (e.g., type 3) and in Neiman-Pick disease (type C).

Gaucher disease (GD) is a rare, autosomal recessive, lysosomal storage disease. GD patients have a mutation in the GBA1 gene which encodes glucosylceramidase (GC), also known as beta-glucocerebrosidase. This enzyme is responsible for breaking down glycosphingolipids into their components, such as breaking down glucosylceramide (GLC; also known as glucocerebroside) into glucose and ceramide. Monocytes and macrophages have a particularly high content of lysosomes containing GLC, and in GD patients these cells become enlarged and accumulate toxic concentrations of GLC. These so-called "Gaucher cells" accumulate in several organs, including the bone, bone marrow, spleen, liver, lung, and brain. Systemically, this results in splenomegaly, hepatomegaly, anemia, thrombocytopenia, leukopenia, osteopenia, osteonecrosis, and other pathologic abnormalities.

There are three subtypes of Gaucher disease, which differ in the age of onset, severity, and presence of neurological manifestations. Type 1 Gaucher disease (GD-1), non-neuronopathic GD, is the most common form, with median age at diagnosis of 28, and mildly reduced life expectancy. In GD-1, the GC enzyme retains some functionality, and there is no neurological involvement. Type-2 GD (GD-2) is acute neuronopathic GD, with diagnosis during infancy, severe neurological involvement, and death usually within the first two years of life. The GC enzyme in a Type-2 patient is more severely compromised in function compared to that of GD-1. Type-3 GD (GD-3) is chronic neuronopathic GD, with diagnosis during childhood, gradually worsening neurological involvement, and life expectancy usually not more than 30 years. Symptoms of GD-3 include spleen and liver abnormalities, fatigue, bleeding, seizures, and supranuclear gaze palsy. The neurological manifestations in GD-3 patients gradually develop over the course of the disease. One of the more debilitating features is gaze palsy, which is a defect in the neuronal pathways controlling saccadic eye movement. During early stages of the disease, there is a slowing in horizontal saccades. The disease progresses to complete horizontal saccadic palsy along with varying degrees of vertical saccadic palsy. The VOR may also be impaired in GD-3 patients. These features of the disease have a profound impact on the quality of life of GD-3 patients and can hinder education and employment prospects.

Existing treatment for GD-1 and GD-3 are limited to recombinant enzyme replacement therapy (ERT) using imiglucerase, velaglucerase, or taliglucerase, and substrate reduction therapy (SRT) using miglustat or eliglustat. See, e.g., Lunawati L. Bennett & Chris Fellner, *Pharmacotherapy of Gaucher Disease: Current and Future Options*, P&T 43(5): 274-280, 309 (2018). Imiglucerase, the leading treatment regimen, is a recombinant version of human GC, made in Chinese hamster ovary cells and administered by slow intravenous injection (typically over 1-2 hours) every 1-2 weeks. It has been available since 1998 in the U.S. Velaglucerase is another recombinant human GC analog, this one made in a fibrosarcoma cell line, and it was FDA-approved in 2010. Taliglucerase is similar, made using genetically modified carrot plant root cells, and has been approved since 2012. These treatments all require IV administration in a hospital or other medical setting, and the recombinant enzymes do not cross the blood-brain barrier and are therefore not capable of treating the neurological symptoms of GD. Thus, while these ERT regimes have proven effective in treating GD-1 patients, in GD-3 patients they are only effective in treating the non-neurological symptoms of the disease.

Substrate-reduction therapy is an alternative approach to treating GD. The goal of this therapy is to reduce the accumulation of GLC by inhibiting the enzyme which is responsible for synthesizing GLC. Glucosylceramide synthase (GCS), also known as UDP-glucose ceramide synthase, is the enzyme which catalyzes the initial glycosylation step of ceramide to form glucosylceramide.

GCS inhibitors have been proposed for the treatment of a variety of diseases, including glycolipid storage diseases and lysosomal storage diseases, including Gaucher disease. See for example, WO 2005/068426 (Actelion Pharm. Ltd.).

Miglustat (Zavesca), is an iminoglucose GCS inhibitor. It is an N-alkylated iminosugar and acts as a reversible competitive inhibitor of GCS, binding in the enzyme's active site. While it was developed to treat the neuronopathic forms of GD, GD-2 and GD-3, the FDA has only approved it for the treatment of patients with mild to moderate GD-1, and only as a second-line therapy (patients must be unable to receive ERT treatment). While miglustat does cross the blood-brain barrier, in clinical trials it was found to be ineffective in treating the neurological manifestations of GD-3. Eliglustat is also a GCS inhibitor, and it is an analogue of the ceremide. It has only been FDA-approved for treatment of the systemic symptoms in GD-1 patients.

Niemann-Pick Disease Type C (NPC) is also a lysosomal storage disease. Although its cause is quite different than Gaucher disease, in some ways the net result is similar. NPC is caused by mutations in either the NPC1 or NPC2 genes. NPC1 is a membrane protein which mediates intracellular trafficking of cholesterol to post-lysosomal destinations. Specifically, NPC1 acts in concert with NPC2 to promote the egress of cholesterol from the endosomal/lysosomal compartment. Unesterified cholesterol that has been released from low density lipoproteins in the lumen of the late endosomes/lysosomes is transferred by NPC2 to the cholesterol-binding pocket of NPC1. Approximately 95% of NPC patients have mutations in NPC1, while most of the remainder have mutations in NPC2. One of the effects of this disrupted cholesterol trafficking is the accumulation of cholesterol and glycosphingolipids (including GLC), in liver, spleen, and brain cells. One of the hallmarks of NPC, like GD-3, is the progressive development of supranuclear gaze palsy, including horizontal and vertical saccadic palsies.

Another group of diseases and disorders commonly associated with saccadic gaze palsies include the GM2-gangliosidoses (such as Tay Sachs disease, Sandhoff disease, and AB variant GM2 gangliosidosis).

GM2 gangliosidoses are, similar to Gaucher disease, lysosomal storage diseases marked by genetic defects in glycosphingolipid metabolism. GM2 gangliosidoses are marked by defects in the enzyme hexosaminidase A and/or its co-factor GM2 activator protein, which are responsible for the breakdown of GM2 to GM3. GM2 and GM3 are related gangliosides which are part of the same metabolic pathway in which glucosylceramide is degraded to ceramide. As such, GM3 is made by a stepwise process that begins with the conversion of ceramide to glucosylceramide (by GLC), followed by conversion to a galactosyl-glucosyl-ceramide, followed by conversion to GM3 (N-acetyl-a-neuraminidyl-galactosyl-glucosylceramide), followed by conversion to GM2 (N-acetyl-galactosyl N-acetyl-a-neuraminidyl-galactosyl-glucosylceramide). The pathological accumulation of GM2 that is the hallmark of GM2 gangliosidoses can thus be ameliorated by a GCS inhibitor which inhibits the earlier synthetic step of glucosylceramide.

The quinuclidine compounds described herein have activity as inhibitors of the enzyme glucosylceramide synthase (GCS). These compounds have been disclosed as generally being useful in the treatment lysosomal storage diseases such as Fabry disease, Gaucher disease, and Niemann-Pick disease. See, e.g., WO 2012/129084 and U.S. 2016/0361301.

There is a real need in the art to develop therapeutics effective in alleviating or managing the neurological symptoms associated with Gaucher Disease Type 3.

SUMMARY OF THE INVENTION

The present invention relates to a quinuclidine compound (Compound 1) according to formula (I),

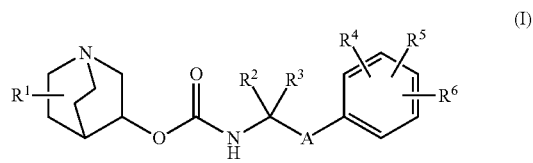

or a pharmaceutically acceptable salt or prodrug thereof, wherein:

$R^1$ is selected from hydrogen, halogen (e.g., fluorine), cyano, nitro, hydroxy, thio, amino, $C_{1-6}$-alkyl (e.g., methyl or ethyl), $C_{2-6}$-alkenyl, $C_{2-6}$-alkynyl, $C_{1-6}$-alkyloxy, $C_{2-6}$-alkenyloxy, and $C_{2-6}$-alkynyloxy, wherein said alkyl, alkenyl, alkynyl, alkyloxy, alkenyloxy, or alkynyloxy is optionally substituted with one or more (e.g., 1, 2, or 3) groups selected from halogen, cyano, nitro, hydroxy, thio, and amino;

$R^2$ and $R^3$ are independently selected from $C_{1-3}$-alkyl, optionally substituted by one or more (e.g., 1, 2, or 3) halogens, or $R^2$ and $R^3$ together form a cyclopropyl or cyclobutyl group, optionally substituted by one or more (e.g., 1 or 2) halogens;

$R^4$, $R^5$, and $R^6$ are each independently selected from hydrogen, halogen, nitro, hydroxy, thio, amino, $C_{1-6}$-alkyl, and $C_{1-6}$-alkyloxy, wherein said alkyl or alkyloxy is optionally substituted by one or more (e.g., 1, 2, or 3) groups selected from halogen, hydroxy, cyano, and $C_{1-6}$-alkyloxy; and A is a 5- or 6-membered aryl or heteroaryl group, optionally substituted with 1, 2, or 3 groups independently selected from a halogen, hydroxy, thio, amino, nitro, $C_{1-6}$-alkoxy, and $C_{1-6}$-alkyl.

In a first aspect the present application provides a method for treating or preventing cognitive dysfunction and/or gait abnormalities, including ataxia, associated with a lysosome storage disease, in a subject, such as in a subject in need thereof, the method comprising administering to the subject an effective amount of a quinuclidine compound as described herein, e.g., a compound according to Formula (I). In other aspects, the present application further provides use of the quinuclidine compounds described herein, for the treatment or prevention of cognitive dysfunction and/or gait abnormalities, including ataxia, associated with a lysosome storage disease, and/or for the manufacture of a medicament for the treatment or prevention of cognitive dysfunction and/or gait abnormalities, including ataxia, associated with a lysosome storage disease.

In a second aspect, the present application provides a method for enhancing neuronal connectivity within the brain of a subject, such as in a subject in need thereof, the method comprising administering to the subject an effective amount of a quinuclidine compound as described herein, e.g., a compound according to Formula (I). In other aspects, the present application further provides use of the quinuclidine compounds described herein, for enhancing neuronal connectivity within the brain of a subject, and/or for the manufacture of a medicament for enhancing neuronal connectivity within the brain of a subject.

In a third aspect, the present application provides a method for increasing brain tissue volume, or preventing or delaying loss of brain tissue volume, in a subject, such as in a subject in need thereof, said method comprising administering to the subject an effective amount of a quinuclidine compound as described herein, e.g., a compound according to Formula (I). In other aspects, the present application further provides the quinuclidine compounds described herein for use in increasing brain tissue volume, or preventing or delaying loss of brain tissue volume, in a subject in need thereof, and/or for the manufacture of a medicament for in increasing brain tissue volume, or preventing or delaying loss of brain tissue volume, in a subject in need thereof.

In a fourth aspect, the present application provides a method for monitoring the progression or regression of a neurological disorder associated with a lysosome storage disease in a subject, wherein the subject is undergoing a treatment which comprises administering to the subject an effective amount of a quinuclidine compound as described herein, e.g., of a compound of Formula (I); said method comprising measuring brain tissue volume of the subject over a time period during the course of the treatment, e.g., using volumetric magnetic resonance imaging (vMRI), and assessing the extent of any change in brain tissue volume over said time period.

In a fifth aspect, the present application provides a method for assessing the onset of a neurological disorder associated with a lysosome storage disease in a subject at risk of developing said neurological disorder, said method comprising: a) measuring the brain tissue volume of the subject (e.g. using vMRI) and comparing against a reference standard to assess whether brain tissue volume is lower than the reference standard; and b) where the brain tissue volume identified in step (a) is lower than the reference standard, identifying the onset of said neurological disorder; the method optionally further comprising: c) commencing treatment of the subject by administering to the subject an effective amount of a quinuclidine compound as described herein, e.g., a compound of Formula (I), or a pharmaceutically acceptable salt or prodrug thereof.

Additional features and advantages of compounds, compositions and methods disclosed herein will be apparent from the following detailed description.

DETAILED DESCRIPTION

Although specific embodiments of the present disclosure will now be described with reference to the preparations and schemes, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

Definitions

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present invention, exemplary methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present disclosure will employ, unless otherwise indicated, conventional techniques of tissue culture, immunology, molecular biology, microbiology, cell biology, and recombinant DNA, which are within the skill of the art.

All numerical designations, e.g., pH, temperature, time, concentration, molecular weight, including ranges, are approximations which are varied (+) or (−) by increments of 0.1 or 1.0, where appropriate. It is to be understood, although not always explicitly stated, that all numerical designations are preceded by the term "about." It also is to be understood, although not always explicitly stated, that the reagents described herein are merely exemplary and that equivalents of such are known in the art.

As used herein, the term "optionally substituted" is meant to be equivalent to the phrase "non-substituted or substituted by."

As used herein, the phrase "in a method of treating or preventing" (such as in the phrase "in a method of treating or preventing pain") is meant to be equivalent to the phrase "in the treatment or prevention of" (such as in the phrase "in the treatment or prevention of pain").

As used in the specification and claims, the singular form "a", "an", and "the" include plural references unless the context clearly dictates otherwise. For example, the term "a cell" includes a plurality of cells, including mixtures thereof. Unless specifically stated or obvious from context, as used herein, the term "or" is understood to be inclusive. The term "including" is used herein to mean, and is used interchangeably with, the phrase "including but not limited to".

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention. Use of the term "comprising" herein is intended to encompass "consisting essentially of" and "consisting of."

A "subject," "individual," or "patient" is used interchangeably herein, and refers to a vertebrate, such as a mammal. Mammals include, but are not limited to, murines, rats, rabbit, simians, bovines, ovine, porcine, canines, felines, farm animals, sport animals, pets, equines, primates, and humans. In one embodiment, the mammals include horses, dogs, and cats. In some embodiments, the mammal is a human, e.g., a human suffering from a particular disease or disorder, such as Gaucher disease (e.g., GD-3) or Niemann-Pick disease Type C. "Administering" is defined herein as a means of providing an agent or a composition containing the agent to a subject in a manner that results in the agent being inside the subject's body. Such an administration can be by any route including, without limitation, oral, transdermal (e.g., vagina, rectum, oral mucosa), by injection (e.g., subcutaneous, intravenous, parenterally, intraperitoneally, into the CNS), or by inhalation (e.g., oral or nasal). Pharmaceutical preparations are, of course, given by forms suitable for each administration route.

"Treating" or "treatment" of a disease generally includes: (1) inhibiting the disease, i.e., arresting or reducing the development of the disease or its clinical symptoms; and/or (2) relieving the disease, i.e., causing regression of the disease or its clinical symptoms.

As used herein, "treating" and "treatment" also refer to either a reversal of the cognitive dysfunction and/or gait abnormalities of the disease or a stabilization of such symptoms. This is because the diseases and disorders described herein are progressive disorders—in the absence of treatment, the condition of the patient will continue to deteriorate. For example, early in the course of disease, a patient may suffer from mild cognitive dysfunction and/or gait abnormalities, but as the disease progresses, patients may develop much more severe symptoms. Treatment thus embraces both a slowing of this progressive deterioration (e.g., stabilization), as well as reversal of this progressive deterioration (e.g., improvement).

"Preventing" or "prevention" of a disease generally includes causing the clinical symptoms of the disease not to develop in a patient that may be predisposed to the disease but does not yet experience or display symptoms of the disease.

As used herein, "preventing" or "prevention" also embraces the prevention of development of cognitive dysfunction and/or gait abnormalities in a patient suspected of having or diagnosed as having a disease or disorder described herein. Because the diseases and disorders described herein are progressive disorders, different signs and symptoms may manifest progressively as the disease advances. Thus, for example, a patient may be diagnosed with GD-3 or NPC before cognitive dysfunction and/or gait abnormalities begin developing. In such a patient, the methods of treatment described herein may be effective in preventing the cognitive dysfunction and/or gait abnormalities from developing.

The term "palsy" is synonymous with "paralysis" and includes any degree of loss of motor function of one or more skeletal muscles. As used herein, the term "palsy" thus embraces both complete palsy, i.e., complete paralysis, as well as partial palsy, i.e., partial paralysis.

Complete palsy means that a muscle or group of muscles, for example the extraocular muscles, have lost the ability to contract. As such, the affected eye or eyes may be unable to move. Partial palsy may be manifested as an inhibition of movement, a slowing of movement, or other defects in movement. These may include a loss of range of motion. As applied to saccades, this can include inhibition of initiating saccades (e.g., in response to stimuli), changes in the frequency of saccades, changes in the peak velocity of saccades, changes in the amplitude of saccades, changes in the latency between saccades, and/or a loss of the ability to hold gaze or to shift gaze. As used herein, in some embodiments, palsy includes ophthalmoparesis and/or ophthalmoplegia. As such, the term embraces both weakness and paralysis of the extraocular muscles. The extraocular muscles include any one or more of the superior recti, inferior recti, medial recti, lateral recti, inferior oblique, and superior oblique muscles of the eye. Weakness and/or paralysis may include one or more of horizontal movement, vertical movement, or rotational movement.

The term "suffering" as it relates to the term "treatment" refers to a patient or individual who has been diagnosed with the disease. The term "suffering" as it relates to the term "prevention" refers to a patient or individual who is predisposed to the disease. A patient may also be referred to being "at risk of suffering" from a disease because of a history of disease in their family lineage or because of the presence of genetic mutations associated with the disease. A patient at risk of a disease has not yet developed all or some of the characteristic pathologies of the disease.

The term "increasing" as it relates to methods of increasing brain tissue volume refers to increasing the volume of at least one, preferably a plurality, of individual brain tissue regions and is typically accompanied by an increase in the whole brain tissue volume (i.e., the total volume of the subject's brain tissue).

An "effective amount" or "therapeutically effective amount" is an amount sufficient to effect beneficial or desired results. An effective amount can be administered in one or more administrations, applications, or dosages. Such delivery is dependent on a number of variables including the time period for which the individual dosage unit is to be used, the bioavailability of the therapeutic agent, and the route of administration. It is understood, however, that specific dose levels of the therapeutic agents of the present invention for any particular subject depends upon a variety of factors including, for example, the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks. Consistent with this definition, as used herein, the term "therapeutically effective amount" is an amount sufficient to treat (e.g., improve) one or more symptoms associated with a disease or disorder described herein (e.g., in any of Methods 1 et seq.) ex vivo, in vitro, or in vivo.

As used herein, the term "pharmaceutically acceptable excipient" encompasses any of the standard pharmaceutical excipients, including carriers such as a phosphate buffered saline solution, water, and emulsions, such as an oil/water or water/oil emulsion, and various types of wetting agents. Pharmaceutical compositions also can include stabilizers and preservatives. For examples of carriers, stabilizers, and adjuvants, see Remington's Pharmaceutical Sciences (20th ed., Mack Publishing Co. 2000).

As used herein, the term "prodrug" means a pharmacological derivative of a parent drug molecule that requires biotransformation, either spontaneous or enzymatic, within the organism to release the active drug. For example, prodrugs are variations or derivatives of the quinuclidine compounds described herein that have groups cleavable under certain metabolic conditions, which when cleaved, become the quinuclidine compounds described herein, e.g., a compound of Formula (I). Such prodrugs then are pharmaceutically active in vivo when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form. Prodrug forms often offer advantages of solubility, tissue compatibility, or delayed release in the mammalian organism.

Prodrugs commonly known in the art include well-known acid derivatives, such as, for example, esters prepared by reaction of acid compounds with a suitable alcohol, amides prepared by reaction of acid compounds with an amine, and basic groups reacted to form an acylated base derivative. Other prodrug derivatives may be combined with other features disclosed herein to enhance bioavailability. As such, those of skill in the art will appreciate that certain of the presently disclosed compounds having, for example, free amino or hydroxy groups can be converted into prodrugs. Prodrugs include compounds having an amino acid residue, or a polypeptide chain of two or more (e.g., two, three or four) amino acid residues which are covalently joined through peptide bonds to free amino, hydroxy, or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline, homocysteine, homoserine, ornithine, and methionine sulfone. Prodrugs also include compounds having a carbonate, carbamate, amide, or alkyl ester moiety covalently bonded to any of the above substituents disclosed herein.

As used herein, the term "pharmaceutically acceptable salt" means a pharmaceutically acceptable acid addition salt or a pharmaceutically acceptable base addition salt of a currently disclosed compound that may be administered without any resultant substantial undesirable biological effect(s) or any resultant deleterious interaction(s) with any other component of a pharmaceutical composition in which it may be contained.

As used herein, the term "$C_{1-6}$-alkyl" means a saturated linear or branched free radical consisting essentially of 1 to 6 carbon atoms and a corresponding number of hydrogen atoms. Exemplary $C_{1-6}$-alkyl groups include methyl, ethyl, n-propyl, isopropyl, n-butyl, and isobutyl. Other $C_{1-6}$-alkyl groups will be readily apparent to those of skill in the art given the benefit of the present disclosure. The terms "$C_{1-3}$-alkyl," "$C_{1-4}$-alkyl," etc., have equivalent meanings, i.e., saturated linear or branched free radical consisting essentially of 1 to 3 (or 4) carbon atoms and a corresponding number of hydrogen atoms.

As used herein, the term "$C_{2-6}$-alkenyl" means an unsaturated linear or branched free radical consisting essentially of 2 to 6 carbon atoms and a corresponding number of hydrogen atoms, which free radical comprises at least one carbon-carbon double bond. Exemplary $C_{2-6}$-alkenyl groups include ethenyl, prop-1-enyl, prop-2-enyl, isopropenyl, but-1-enyl, 2-methyl-prop-1-enyl, and 2-methyl-prop-2-enyl. Other $C_{2-6}$-alkenyl groups will be readily apparent to those of skill in the art given the benefit of the present disclosure.

As used herein, the term "$C_{2-6}$-alkynyl" means an unsaturated linear or branched free radical consisting essentially of 2 to 6 carbon atoms and a corresponding number of hydrogen atoms, which free radical comprises at least one carbon-carbon triple bond. Exemplary $C_{2-6}$-alkynyl groups include ethynyl, prop-1-ynyl, prop-2-ynyl, but-1-ynyl, and 3-methyl-but-1-ynyl. Other $C_{2-6}$-alkynyl groups will be readily apparent to those of skill in the art given the benefit of the present disclosure.

As used herein, the term "$C_{1-6}$-alkyloxy" means a saturated linear or branched free radical consisting essentially of 1 to 6 carbon atoms (and a corresponding number of hydrogen atoms) and an oxygen atom. A $C_{1-6}$-alkyloxy group is attached via the oxygen atom. Exemplary $C_{1-6}$-alkyloxy groups include methyloxy, ethyloxy, n-propyloxy, isopropyloxy, n-butyloxy, and isobutyloxy. Other $C_{1-6}$-alkyloxy groups will be readily apparent to those of skill in the art given the benefit of the present disclosure. The terms "$C_{1-3}$-alkyloxy," "$C_{1-4}$-alkyloxy," and the like, have an equivalent meaning, i.e., a saturated linear or branched free radical consisting essentially of 1 to 3 (or 4) carbon atoms (and a corresponding number of hydrogen atoms) and an oxygen atom, wherein the group is attached via the oxygen atom.

As used herein, the term "$C_{2-6}$-alkenyloxy" means an unsaturated linear or branched free radical consisting essentially of 2 to 6 carbon atoms (and a corresponding number of hydrogen atoms) and an oxygen atom, which free radical comprises at least one carbon-carbon double bond. A $C_{2-6}$-alkenyloxy group is attached via the oxygen atom. An exemplary $C_{2-6}$-alkenyloxy group is ethenyloxy; others will be readily apparent to those of skill in the art given the benefit of the present disclosure.

As used herein, the term "$C_{2-6}$-alkynyloxy" means an unsaturated linear or branched free radical consisting essentially of 2 to 6 carbon atoms (and a corresponding number of hydrogen atoms) and an oxygen atom, which free radical comprises at least one carbon-carbon triple bond. A $C_{2-6}$-alkenyloxy group is attached via the oxygen atom. An exemplary $C_{2-6}$-alkenyloxy group is ethynyloxy; others will be readily apparent to those of skill in the art given the benefit of the present disclosure.

As used herein, the term "heteroaryl" means an aromatic free radical having 5 or 6 atoms (i.e., ring atoms) that form a ring, wherein 1 to 5 of the ring atoms are carbon and the remaining 1 to 5 ring atom(s) (i.e., hetero ring atom(s)) is selected independently from the group consisting of nitrogen, sulfur, and oxygen. Exemplary 5-membered heteroaryl groups include furyl, thienyl, thiazolyl (e.g., thiazol-2-yl), pyrazolyl, isothiazolyl, oxazolyl, isoxazolyl, pyrrolyl, triazolyl, imidazolyl, oxadiazolyl and thiadiazolyl. Exemplary 6-membered heteroaryl groups include pyridyl, pyrimidyl, pyrazinyl, pyridazinyl, 1,2,4-triazinyl, benzoxazolyl, benzothiazolyl, benzisothiazolyl, benzisoxazolyl, and benzimidazolyl. Other heteroaryl groups will be readily apparent to those of skill in the art given the benefit of the present disclosure. In general, the heteroaryl group typically is attached to the main structure via a carbon atom. However, those of skill in the art will realize that certain other atoms, e.g., hetero ring atoms, can be attached to the main structure.

As used herein, the term "aryl" means an aromatic free radical having 5 or 6 atoms (i.e., ring atoms) that form a ring, wherein all of the ring atoms are carbon. An exemplary aryl group is a phenyl group.

As used herein, the term "aliphatic" means a non-aromatic compound containing carbon and hydrogen atoms, e.g., containing 1 to 9 carbon atoms. Aliphatic compounds may be straight-chained or branched, may contain one or more ring structures, and may contain one or more carbon-carbon double bonds (provided that the compound does not contain an unsaturated ring structure having aromatic character). Examples of aliphatic compounds include ethane, propylene, cyclobutane, and cyclohexadiene.

As used herein, the terms "halo" and "halogen" mean fluorine, chlorine, bromine, or iodine. These terms are used interchangeably and may refer to a halogen free radical group or to a halogen atom as such. Those of skill in the art will readily be able to ascertain the identification of which in view of the context in which this term is used in the present disclosure.

As used herein, the term "cyano" means a free radical having a carbon atom linked to a nitrogen atom via a triple bond. The cyano radical is attached via its carbon atom.

As used herein, the term "nitro" means an —NO$_2$ radical which is attached via its nitrogen atom.

As used herein, the terms "hydroxy" and "hydroxyl" mean an —OH radical which is attached via its oxygen atom. The term "thio" means an —SH radical which is attached via its sulfur atom.

As used herein, the term "amino" means a free radical having a nitrogen atom and 1 or 2 hydrogen atoms. As such, the term "amino" generally refers to primary and secondary amines. In that regard, as used herein, a tertiary amine is represented by the general formula RR'N—, wherein R and R' are carbon radicals that may or may not be identical. Nevertheless, the term "amino" generally may be used herein to describe a primary, secondary, or tertiary amine, and those of skill in the art will readily be able to ascertain the identification of which in view of the context in which this term is used in the present disclosure.

As used herein, the term and "oxo" means an oxygen radical which is attached via a double bond. Where an atom bonded to this oxygen is a carbon atom, the bond is a carbon-oxygen double bond which may be denoted as —(C=O)— and which may be referred to as a ketone.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The following abbreviations are used herein:
br Broad signal
CDI Carbonyldiimidazole
CNS Central Nervous System
CSF Cerebrospinal fluid
d Doublet
dd Doublet of doublets
DME Dimethoxyethane
DMSO-d6 Dimethyl sulfoxide-d6
DMF Dimethylformamide
DNA Deoxyribonucleic acid
EDTA Ethylenediaminetetraacetic acid
EtMgBr Ethylmagnesium bromide
EtOAc Ethyl acetate
GL1 Glucosylceramide (GlcCer)
GM3 Monosialodihexosylganglioside
HPLC High pressure/performance liquid chromatography
HSA Human serum albumin
IPA Isopropyl alcohol
J Coupling constant
LCMS Liquid chromatography mass spectrometry
m Multiplet
ppm Parts per million
rHA Recombinant human albumin
s Singlet
TBME Tert-Butyl Methyl Ether
THF Tetrahydrofuran
Tris Tris(hydroxymethyl)aminomethane
TWEEN20 Polysorbate 20
TWEEN80 Polysorbate 80
VOR Vestibulo-ocular reflex
UPLCMS Ultra performance liquid chromatography mass spectrometry Compounds The present disclosure relates to quinuclidine compounds for use in therapeutic methods relating to the treatment or prevention of the diseases and disorders discussed herein. In all of its various aspects, the invention relates to a quinuclidine compound (Compound 1) according to formula (I),

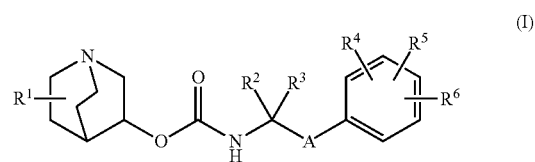

or a pharmaceutically acceptable salt or prodrug thereof, wherein:

$R^1$ is selected from hydrogen, halogen (e.g., fluorine), cyano, nitro, hydroxy, thio, amino, $C_{1-6}$-alkyl (e.g., methyl or ethyl), $C_{2-6}$-alkenyl, $C_{2-6}$-alkynyl, $C_{1-6}$-alkyloxy, $C_{2-6}$-alkenyloxy, and $C_{2-6}$-alkynyloxy, wherein said alkyl, alkenyl, alkynyl, alkyloxy, alkenyloxy, or alkynyloxy is optionally substituted with one or more (e.g., 1, 2, or 3) groups selected from halogen, cyano, nitro, hydroxy, thio, or amino;

$R^2$ and $R^3$ are independently selected from $C_{1-3}$-alkyl, optionally substituted by one or more (e.g., 1, 2, or 3) halogens, or $R^2$ and $R^3$ together form a cyclopropyl or cyclobutyl group, optionally substituted by one or more (e.g., 1 or 2) halogens;

$R^4$, $R^5$ and $R^6$ are each independently selected from hydrogen, halogen, nitro, hydroxy, thio, amino, $C_{1-6}$-alkyl, and $C_{1-6}$-alkyloxy, wherein said alkyl or alkyloxy is optionally substituted by one or more (e.g., 1, 2 or 3) groups selected from halogen, hydroxy, cyano, and $C_{1-6}$-alkyloxy; and A is a 5- or 6-membered aryl or heteroaryl group (e.g., phenyl or thiazolyl), optionally substituted with 1, 2, or 3 groups independently selected from halogen, hydroxy, thio, amino, nitro, $C_{1-6}$-alkoxy, and $C_{1-6}$-alkyl.

In further embodiments of the any aspects of the present disclosure, the present disclosure further relates to Compounds as follows:

1.1 Compound 1, wherein $R^1$ is selected from hydrogen, halogen, cyano, nitro, hydroxy, thio, amino, $C_{1-6}$-alkyl, and $C_{1-6}$-alkyloxy, wherein said alkyl or alkyloxy is optionally substituted with one or more (e.g., 1, 2, or 3) groups selected from halogen, cyano, nitro, hydroxy, thio, and amino;

1.2 Compound 1, wherein $R^1$ is selected from hydrogen, halogen, $C_{1-6}$-alkyl, and $C_{1-6}$-alkyloxy, wherein said alkyl or alkyloxy is optionally substituted with one or more (e.g., 1, 2, or 3) groups selected from halogen, cyano, nitro, hydroxy, thio, and amino;

1.3 Compound 1, wherein $R^1$ is selected from hydrogen, halogen, $C_{1-4}$-alkyl, and $C_{1-4}$-alkyloxy, wherein said alkyl or alkyloxy is optionally substituted with one or more (e.g., 1, 2, or 3) groups selected from halogen, cyano, nitro, hydroxy, thio, and amino;

1.4 Compound 1, wherein $R^1$ is selected from hydrogen, halogen, $C_{1-4}$-alkyl, and $C_{1-4}$-alkyloxy, wherein said alkyl or alkyloxy is optionally substituted with one or more (e.g., 1, 2, or 3, or 1 or 2) groups selected from cyano, nitro, hydroxy, thio, and amino;

1.5 Compound 1, wherein $R^1$ is selected from hydrogen, halogen, and $C_{1-4}$-alkyl, wherein said alkyl is optionally substituted with one or more (e.g., 1 or 2) groups selected from halogen, hydroxy, thio, and amino;

1.6 Compound 1, wherein $R^1$ is selected from hydrogen, fluorine, methyl, and ethyl, wherein said methyl or ethyl is optionally substituted with 1 or 2 groups selected from halogen, hydroxy, thio, and amino;

1.7 Compound 1, wherein $R^1$ is selected from hydrogen and methyl, wherein said methyl is optionally substituted with 1 or 2 halogens;

1.8 Compound 1, wherein $R^1$ is hydrogen;

1.9 Compound 1, or any of 1.1-1.8, wherein $R^1$ is not attached to the nitrogen atom of the quinuclidine moiety;

1.10 Compound 1, or any of 1.1-1.9, wherein $R^2$ and $R^3$ are each independently $C_{1-3}$-alkyl, optionally substituted by one or more (e.g., 1, 2, or 3) halogens;

1.11 Compound 1.10, wherein $R^2$ and $R^3$ are each independently methyl or ethyl, optionally substituted by 1 or 2 halogens;

1.12 Compound 1.10, wherein $R^2$ and $R^3$ are each independently selected from methyl and ethyl, optionally substituted by one or more fluorines, e.g., 1, 2, 3 or 4 fluorines;

1.13 Compound 1.10, wherein $R^2$ and $R^3$ are each independently methyl substituted with 0, 1, 2, or 3 fluorines;

1.14 Compound 1.10, wherein $R^2$ and $R^3$ are each methyl or trifluoromethyl;

1.15 Compound 1.10, $R^2$ and $R^3$ are each methyl;

1.16 Compound 1, or any of 1.1-1.9, wherein $R^2$ and $R^3$ together form a cyclopropyl or cyclobutyl group, optionally substituted by one or more (e.g., 1 or 2) halogens;

1.17 Compound 1.16, wherein $R^2$ and $R^3$ together form a cyclopropyl group;

1.18 Compound 1 or any of 1.1-1.9, wherein $R^2$ and $R^3$ are each methyl or $R^2$ and $R^3$ together form a cyclopropyl group;

1.19 Compound 1, or any of 1.1-1.9, wherein $R^4$, $R^5$, and $R^6$ are each independently selected from hydrogen, halogen, $C_{1-6}$-alkyl, and $C_{1-6}$-alkyloxy, wherein said alkyl or alkyloxy is optionally substituted by one or more (e.g., 1, 2, or 3) groups selected from halogen, hydroxy, cyano, and $C_{1-6}$-alkyloxy;

1.20 Compound 1, or any of 1.1-1.9, wherein $R^4$, $R^5$, and $R^6$ are each independently selected from hydrogen, halogen, $C_{1-3}$-alkyl, and $C_{1-3}$-alkyloxy, wherein said alkyl or alkyloxy is optionally substituted by one or more (e.g., 1, 2, or 3) groups selected from halogen, hydroxy, cyano, and $C_{1-3}$-alkyloxy;

1.21 Compound 1.19, wherein $R^4$, $R^5$, and $R^6$ are each independently selected from hydrogen, halogen, $C_{1-3}$-alkyl, and $C_{1-3}$-alkyloxy, wherein said alkyl or alkyloxy is optionally substituted by one or more (e.g., 1, 2, or 3) groups selected from halogen, cyano, and $C_{1-3}$-alkyloxy;

1.22 Compound 1.19, wherein $R^4$, $R^5$, and $R^6$ are each independently selected from hydrogen, halogen, $C_{1-3}$-alkyl, and $C_{1-3}$-alkyloxy, wherein said alkyl or alkyloxy is optionally substituted by one or more (e.g., 1, 2, or 3) groups selected from halogen and $C_{1-3}$-alkyloxy;

1.23 Compound 1.19, wherein $R^4$, $R^5$, and $R^6$ are each independently selected from halogen, $C_{1-3}$-alkyl, and $C_{1-3}$-alkyloxy, wherein said alkyl or alkyloxy is optionally substituted by one or more (e.g., 1, 2, or 3) groups selected from halogen and $C_{1-3}$-alkyloxy 1.24 Compound 1, or any of 1.19-1.23, wherein $R^4$ is selected from hydrogen, halogen, $C_{1-3}$-alkyl, and $C_{1-3}$-alkyloxy, wherein said alkyl or alkyloxy is optionally substituted by one or more (e.g., 1, 2, or 3) groups selected from halogen and $C_{1-3}$-alkyloxy;

1.25 Compound 1.24, wherein $R^4$ is selected from halogen (e.g., fluorine), $C_{1-3}$-alkyl (e.g., methyl), and $C_{1-3}$-alkyloxy (e.g., methoxy or ethoxy), wherein said alkyl or alkyloxy is optionally substituted by one or more (e.g., 1, 2, or 3) groups selected from halogen and $C_{1-3}$-alkyloxy (e.g., methoxy or ethoxy);

1.26 Compound 1.25, wherein $R^4$ is selected from halogen (e.g., fluorine) and $C_{1-3}$-alkyloxy (e.g., methoxy or ethoxy), wherein said alkyloxy is optionally substituted by one or more (e.g., 1, 2, or 3) groups selected from halogen and $C_{1-3}$-alkyloxy (e.g., methoxy or ethoxy);

1.27 Compound 1.26, wherein $R^4$ is fluorine or $C_{1-3}$-alkyloxy (e.g., ethoxy), optionally substituted by one or more (e.g., 1, 2, or 3) groups selected from halogen and $C_{1-3}$-alkyloxy (e.g., methoxy);

1.28 Compound 1.26, wherein $R^4$ is fluorine or ethoxy optionally substituted by one or more (e.g., 1, 2, or 3) $C_{1-3}$-alkyloxy (e.g., methoxy);

1.29 Compound 1, or any of 1.19-1.28, wherein $R^6$ is hydrogen;

1.30 Compound 1, or any of 1.19-1.28, wherein $R^5$ and $R^6$ are each hydrogen;

1.31 Compound 1, or any of 1.19-1.28, $R^5$ and $R^6$ are each hydrogen, and $R^4$ is fluorine or $C_{1-3}$-alkyloxy (e.g., ethoxy), optionally substituted by one or more (e.g., 1, 2, or 3) groups selected from halogen and $C_{1-3}$-alkyloxy (e.g., methoxy);

1.32 Compound 1.31, wherein $R^5$ and $R^6$ are each hydrogen, and $R^4$ is fluorine or ethoxy optionally substituted by one or more (e.g., 1, 2 or 3) $C_{1-3}$-alkyloxy (e.g., methoxy);

1.33 Compound 1.32, wherein $R^5$ and $R^6$ are each hydrogen, and $R^4$ is fluorine or ethoxy substituted with methoxy (e.g., 2-methoxyethoxy);

1.34 Compound 1.32, wherein $R^4$ is fluorine or 2-methoxyethoxy;

1.35 Compound 1, or any of 1.1-1.34, wherein at least one of $R^4$, $R^5$, and $R^6$ is not hydrogen;

1.36 Compound 1, or any of 1.1-1.35, wherein $R^6$ is hydrogen, and $R^4$ and $R^5$ are positioned at the 2, 4, or 6 positions of the phenyl ring to which they are attached (i.e., ortho or para to the A substituent);

1.37 Compound 1, or any of 1.1-1.35, wherein $R^6$ is hydrogen, and $R^4$ and $R^5$ are positioned independently at the 2 and 3 (i.e., adjacent ortho and meta), 3 and 4 (i.e., adjacent meta and para), or 3 and 5 positions (i.e., meta) of the phenyl ring to which they are attached (with respect to the A substituent);

1.38 Compound 1, or any of 1.1-1.35, wherein $R^6$ is hydrogen, and $R^4$ and $R^5$ are positioned at the 3 and 5 positions (i.e., meta) of the phenyl ring to which they are attached (with respect to the A substituent);

1.39 Compound 1, or any of 1.1-1.35, wherein $R^5$ and $R^6$ are hydrogen, and $R^4$ is positioned at the 2, 3, or 4 position of the phenyl ring to which it is attached (e.g., ortho, meta, or para or to the A substituent);

1.40 Compound 1, or any of 1.1-1.35, wherein $R^5$ and $R^6$ are hydrogen, and $R^4$ is positioned at the 2 or 4 position of the phenyl ring to which it is attached (e.g., ortho or para to the A substituent);

1.41 Compound 1, or any of 1.1-1.35, wherein $R^5$ and $R^6$ are hydrogen, and $R^4$ is positioned at the 4 position of the phenyl ring to which it is attached (e.g., para to the A substituent);

1.42 Compound 1, or any of 1.1-1.35, wherein none of $R^4$, $R^5$, and $R^6$ are hydrogen, and each of $R^4$, $R^5$, and $R^6$ are independently positioned at the 2, 4, or 6 positions of the phenyl ring to which they are attached (i.e., ortho or para to the A substituent);

1.43 Compound 1, or any of 1.1-1.42, wherein $R^4$ is positioned at the 4-position of the phenyl ring to which it is attached (i.e., para to the A substituent);

1.44 Compound 1, or any of 1.1-1.43, wherein A is a 6-membered aryl group, a 5-membered heteroaryl group (e.g., containing 1, 2 or 3 heteroatoms in the heteroaryl ring independently selected from N, O and S), or a 6-membered heteroaryl group (e.g., containing 1, 2 or 3 nitrogen atoms in the heteroaryl ring);

1.45 Compound 1.44, wherein A is a 6-membered aryl group or a 5-membered heteroaryl group (e.g., containing 1, 2 or 3 heteroatoms in the heteroaryl ring independently selected from N, O, and S), optionally wherein the 5-membered heteroaryl group contains 1 or 2 heteroatoms selected from N and S (e.g., one N and/or one S);

1.46 Compound 1.44 or 1.45, wherein A is selected from the group consisting of phenyl, furyl, thienyl, thiazolyl, pyrazolyl, isothiazolyl, oxazolyl, isoxazolyl, pyrrolyl, triazolyl, imidazolyl, oxadiazolyl, and thiadiazolyl;

1.47 Compound 1.46, wherein A is selected from the group consisting of phenyl, thienyl, thiazolyl, pyrrolyl, and imidazolyl;

1.48 Compound 1.46, wherein A is selected from the group consisting of phenyl and thiazolyl, e.g., 2-thiazol-4-yl or 4-thiazol-2-yl;

1.49 Compound 1, or any of 1.1-1.48, wherein A is unsubstituted 1.50 Compound 1, or any of 1.1-1.48, wherein A is substituted with one or more (e.g., 1, 2, or 3) groups independently selected from a halogen, hydroxy, thio, amino, nitro, $C_{1-6}$-alkoxy, and $C_{1-6}$-alkyl (e.g., methyl);

1.51 Compound 1.50, wherein A is thiazolyl substituted with one halogen (e.g., fluorine) or $C_{1-6}$-alkyl (e.g., methyl);

1.52 Compound 1.50, wherein A is phenyl substituted with 1, 2, or 3 groups independently selected from halogen (e.g., fluorine) and $C_{1-6}$-alkyl (e.g., methyl);

1.53 Compound 1.52, wherein A is phenyl substituted with 1 or 2 fluorines or methyl groups;

1.54 Compound 1, or any of 1.1-1.53, wherein the two groups attached to the A substituent (i.e., the phenyl ring ($—(C_6H_2R^4R^5R^6)$) and the $—C(R^2R^3)—$ group) are positioned in a 1,2-, 1,3-, or 1,4-relationship to each other (i.e., ortho, meta, or para);

1.55 Compound 1.54, wherein the two groups attached to the A substituent are positioned in a 1,3-relationship to each other (i.e., meta);

1.56 Compound 1.54, wherein the two groups attached to the A substituent are positioned in a 1,4-relationship to each other (i.e., para);

1.57 Any of Compounds 1.54 to 1.56, wherein the A substituent is a 5-membered heteroaryl group and at least one of the two groups attached to the A substituent (i.e., the phenyl ring ($—(C_6H_2R^4R^5R^6)$) or the $—C(R^2R^3)—$ group) is attached to a carbon atom of the heteroaryl ring, optionally wherein both of such groups are attached to carbon atoms of the heteroaryl ring;

1.58 Compound 1, or any of 1.1-1.57, wherein the Compound of Formula (I) can be represented by any one or more of the following substructures:

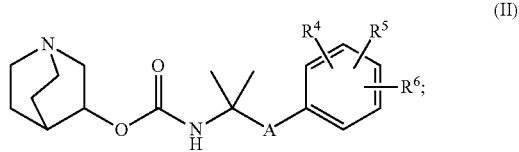

(II)

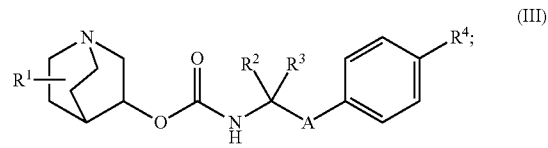

(III)

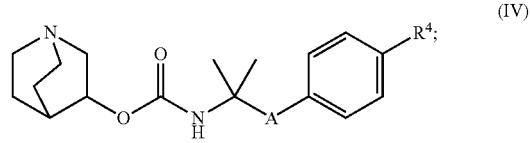

(IV)

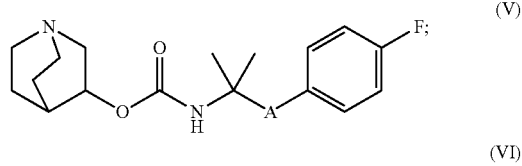

(V)

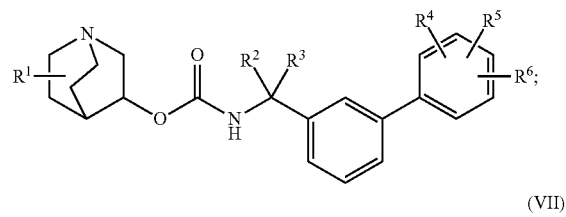

(VI)

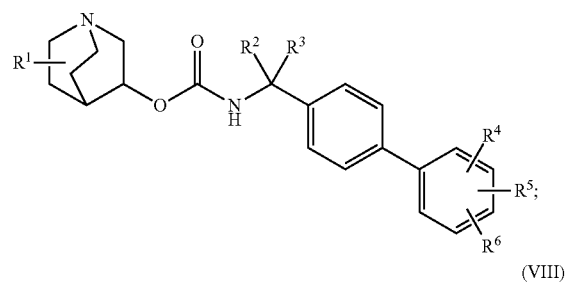

(VII)

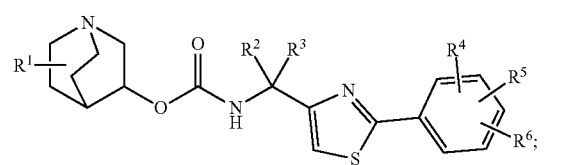

(VIII)

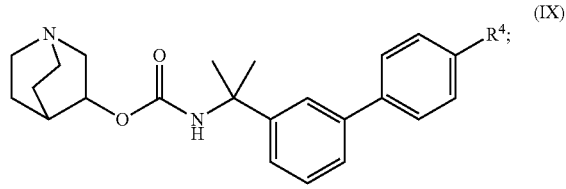

(IX)

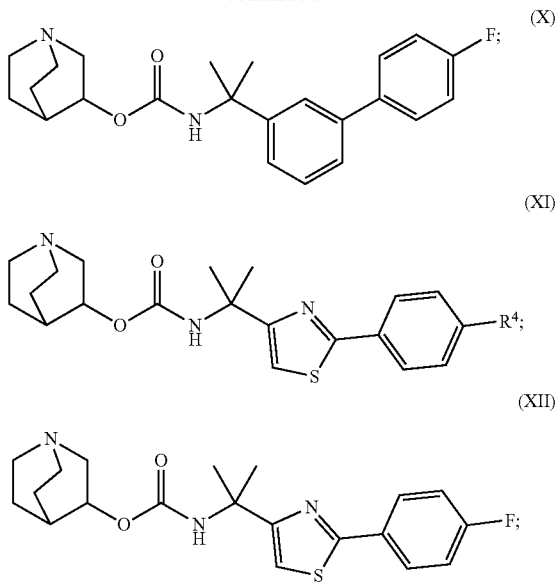

1.59 Compound 1, or any of 1.1-1.58, wherein the compound of Formula (I), or any of Formulas (II) to (XII), has the (S) configuration;
1.60 Compound 1, or any of 1.1-1.58, wherein the compound of Formula (I), or any of Formulas (II) to (XII), has the (R) configuration;
1.61 Compound 1, or any of 1.1-1.60, wherein the compound of Formula (I), or any of Formulas (II) to (XII), has an enantiomeric excess (e.g., of the (S) configuration) of at least 90%, e.g., at least 92%, 93%, 94%, 95%, 96%, 97%, 98%, 99%, 99.5% or 99.9%;
1.62 Compound 1, or any of 1.1-1.58, wherein the compound of Formula (I), or any of Formulas (II) to (XII), is racemic (i.e., approximately a 50:50 ratio of enantiomers), or is a mixture of enantiomers of some other ratio (e.g., less than 50:50 or greater than 50:50);
1.63 Compound 1, or any of 1.1-1.62, wherein the Compound of Formula (I) is selected from the group consisting of:

| Compound No. | Compound |
|---|---|
| 1 | Quinuclidin-3-yl (2-(4'-fluoro-[1,1'-biphenyl]-3-yl)propan-2-yl)carbamate |
| 2 | (S)-quinuclidin-3-yl (2-(2-(4-fluorophenyl)thiazol-4-yl)propan-2-yl)carbamate |
| 3 | (S)-quinuclidin-3-yl (2-(4'-(2-methoxyethoxy)-[1,1'-biphenyl]-4-yl)propan-2-yl)carbamate |
| 4 | 1-azabicyclo[2.2.2]oct-3-yl [2-(biphenyl-3-yl)propan-2-yl]carbamate |
| 5 | (S)-quinuclidin-3-yl 2-(biphenyl-4-yl)propan-2-ylcarbamate |
| 6 | Quinuclidin-3-yl 1-(biphenyl-4-yl)cyclopropylcarbamate |
| 7 | (S)-quinuclidin-3-yl 1-(4'-fluorobiphenyl-4-yl)cyclopropylcarbamate |
| 8 | (S)-1-azabicyclo[2.2.2]oct-3-yl [1-(2',4'-difluorobiphenyl-4-yl)cyclopropyl]carbamate |
| 9 | 1-azabicyclo[2.2.2]oct-3-yl [1-(4'-methoxybiphenyl-4-yl)cyclopropyl]carbamate |
| 10 | Quinuclidin-3-yl 2-(5-(4-fluorophenyl)thiophen-3-yl)propan-2-ylcarbamate |
| 11 | (S)-quinuclidin-3-yl 2-(3-(4-fluorophenyl)isothiazol-5-yl)propan-2-ylcarbamate |
| 12 | (S)-quinuclidin-3-yl 2-(4-(4-fluorophenyl)thiazol-2-yl)propan-2-ylcarbamate |
| 13 | Quinuclidin-3-yl (2-(4'-(2-methoxyethoxy)-[1,1'-biphenyl]-4-yl)propan-2-yl)carbamate |
| 14 | (S)-quinuclidin-3-yl (2-(3'-(2-methoxyethoxy)-[1,1'-biphenyl]-4-yl)propan-2-yl)carbamate |
| 15 | Quinuclidin-3-yl (2-(4'-(2-methoxyethoxy)-[1,1'-biphenyl]-3-yl)propan-2-yl)carbamate |
| 16 | Quinuclidin-3-yl (2-(4'-(3-methoxypropoxy)-[1,1'-biphenyl]-4-yl)propan-2-yl)carbamate |
| 17 | Quinuclidin-3-yl (2-(4'-(hydroxymethyl)-[1,1'-biphenyl]-4-yl)propan-2-yl)carbamate |
| 18 | Quinuclidin-3-yl (2-(4'-(2-hydroxyethyl)-[1,1'-biphenyl]-4-yl)propan-2-yl)carbamate |
| 19 | Quinuclidin-3-yl (2-(2-(4-(3-methoxypropoxy)phenyl)thiazol-4-yl)propan-2-yl)carbamate |
| 20 | Quinuclidin-3-yl (2-(2-(4-(2-methoxyethoxy)phenyl)thiazol-4-yl)propan-2-yl)carbamate |
| 21 | Quinuclidin-3-yl 2-(5-(4-(2-methoxyethoxy)phenyl)pyridin-2-yl)propan-2-ylcarbamate |
| 22 | Quinuclidin-3-yl (2-(4'-(3-cyanopropoxy)-[1,1'-biphenyl]-4-yl)propan-2-yl)carbamate |
| 23 | Quinuclidin-3-yl (2-(4'-(cyanomethoxy)-[1,1'-biphenyl]-4-yl)propan-2-yl)carbamate |

1.64 Compound 1, or any of 1.1-1.63, wherein the compound is selected from quinuclidin-3-yl (2-(4'-fluoro-[1,1'-biphenyl]-3-yl)propan-2-yl)carbamate, (S)-quinuclidin-3-yl (2-(2-(4-fluorophenyl)thiazol-4-yl)propan-2-yl)carbamate, and (S)-quinuclidin-3-yl (2-(4'-(2-methoxyethoxy)-[1,1'-biphenyl]-4-yl)propan-2-yl)carbamate;
1.65 Compound 1, or any of 1.1-1.63, wherein the compound is quinuclidin-3-yl (2-(4'-fluoro-1[1,1'-biphenyl]-3-yl)propan-2-yl)carbamate;
1.66 Compound 1 or any of 1.1-1.63, wherein the compound is quinuclidin-3-yl (2-(2-(4-fluorophenyl)thiazol-4-yl)propan-2-yl)carbamate, e.g., (S)-quinuclidin-3-yl (2-(2-(4-fluorophenyl)thiazol-4-yl)propan-2-yl)carbamate;
1.67 Compound 1, or any of 1.1-1.66, wherein the Compound of Formula (I), or any of (II) to (XII), is in free base form;
1.68 Compound 1, or any of 1.1-1.66, wherein the Compound of Formula (I), or any of (II) to (XII), is in pharmaceutically acceptable salt form;
1.69 Compound 1.68, wherein said salt form is an acid addition salt form;
1.70 Compound 1.69, wherein said acid addition salt form is a salt selected from the hydrochloride, hydrobromide, hydroiodide, nitrate, sulfate, bisulfate, phosphate, acid phosphate, acetate, lactate, citrate, acid citrate, tartrate, bitartrate, succinate, hydroxysuccinate, malate, maleate, fumarate, gluconate, saccharate, benzoate, methanesulfonate, and pamoate;
1.71 Compound 1.70, wherein the acid addition salt form is selected from hydrochloride, hydroxysuccinate (e.g., 2-hydroxysuccinate), and malate;
1.72 Compound 1.68, wherein said salt form is a base addition salt form;
1.73 Compound 1, or any of 1.1-1.72, wherein the compound is (S)-quinuclidin-3-yl (2-(2-(4-fluorophenyl)thiazol-4-yl)propan-2-yl)carbamate in malate salt form;
1.74 Compound 1, or any of 1.1-1.73, wherein the Compound of Formula (I), or any of (II) to (XII), is in the form of a prodrug, as described herein;

1.75 Compound 1, or any of 1.1-1.74, wherein the Compound of Formula (I), or any of (II) to (XII), is in the form of a hydrate, solvate and/or polymorph.

Salts

Presently disclosed compounds, e.g., any of Compounds 1 or 1.1-1.75, that are basic in nature are generally capable of forming a wide variety of different salts with various inorganic and/or organic acids. Although such salts are generally pharmaceutically acceptable for administration to animals and humans, it is often desirable in practice to initially isolate a compound from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds can be readily prepared using conventional techniques, e.g., by treating the base compound with a substantially equivalent amount of the chosen mineral or organic acid in an aqueous solvent medium or in a suitable organic solvent such as, for example, methanol or ethanol. Upon careful evaporation of the solvent, the desired solid salt is obtained. Presently disclosed compounds that are positively charged, e.g., containing a quaternary ammonium, may also form salts with the anionic component of various inorganic and/or organic acids.

Acids which can be used to prepare pharmaceutically acceptable salts of quinuclidine compounds are those which can form non-toxic acid addition salts, e.g., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, malate, maleate, fumarate, gluconate, saccharate, benzoate, methanesulfonate, and pamoate [i.e., 1,1'-methylene-bis-(2-hydroxy-3-naphthoate)] salts.

Presently disclosed compounds that are acidic in nature, e.g., compounds containing a thiol moiety, are generally capable of forming a wide variety of different salts with various inorganic and/or organic bases. Although such salts are generally pharmaceutically acceptable for administration to animals and humans, it is often desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations, and then evaporating the resulting solution to dryness, e.g., under reduced pressure. Alternatively, they also can be prepared by mixing lower alkanolic solutions of the acidic compounds and the desired alkali metal alkoxide together, and then evaporating the resulting solution to dryness in the same manner as before. In either case, stoichiometric quantities of reagents may be employed in order to ensure completeness of reaction and maximum product yields of the desired solid salt.

Bases which can be used to prepare the pharmaceutically acceptable base addition salts of quinuclidine compounds are those which can form non-toxic base addition salts, e.g., salts containing pharmacologically acceptable cations, such as, alkali metal cations (e.g., potassium and sodium), alkaline earth metal cations (e.g., calcium and magnesium), ammonium or other water-soluble amine addition salts such as N-methylglucamine (meglumine), lower alkanolammonium, and other such bases of organic amines.

In one embodiment, the pharmaceutically acceptable salt is a succinate salt. In another embodiment, the pharmaceutically acceptable salt is a 2-hydroxysuccinate salt, e.g., an (S)-2-hydroxysuccinate salt. In another embodiment, the pharmaceutically acceptable salt is a hydrochloride salt (i.e., a salt with HCl). In another embodiment, the pharmaceutically acceptable salt is a malate salt.

Prodrugs

The present disclosure further embraces prodrugs of the compounds 1 and 1.1-1.75. The pharmaceutically acceptable prodrugs disclosed herein are derivatives of quinuclidine compounds which can be converted in vivo into the quinuclidine compounds described herein. The prodrugs, which may themselves have some activity, become pharmaceutically active in vivo when they undergo, for example, solvolysis under physiological conditions or enzymatic degradation. Methods for preparing prodrugs of compounds as described herein would be apparent to one of skill in the art based on the present disclosure.

In one embodiment, the carbamate moiety of the quinuclidine compound is modified. For example, the carbamate moiety of the quinuclidine compound may be modified by the addition of water and/or one or two aliphatic alcohols. In this case, the carbon-oxygen double bond of the carbamate moiety adopts what could be considered a hemiacetal or acetal functionality. In one embodiment, the carbamate moiety of the quinuclidine compound may be modified by the addition of an aliphatic diol such as 1,2-ethanediol.

In one embodiment, one or more of the hydroxy, thio, or amino groups on the quinuclidine compound are modified. For example, one or more of the hydroxy, thio, and/or amino groups on the quinuclidine compound may be modified to form acid derivatives, e.g., esters, thioesters (or thiolesters), and/or amides. The acid derivatives can be formed, for example, by reacting a quinuclidine compound which comprises one or more hydroxy, thio, or amino groups with an acetylating agent. Examples of acetylating agents include anhydrides such as acetic anhydride, acid chlorides such as benzyl chloride, and dicarbonates such as di-tert-butyl dicarbonate.

Stereochemistry

The present disclosure further embraces stereoisomers and mixture of stereoisomers of compounds 1 and 1.1-1.75. Stereoisomers (e.g., cis and trans isomers) and all optical isomers of a presently disclosed compound (e.g., R- and S-enantiomers), as well as racemic, diastereomeric, and other mixtures of such isomers are within the scope of the present disclosure.

In one embodiment, the quinuclidin-3-yl group of a quinuclidine compound as defined herein has the R-configuration. Accordingly, the quinuclidine compound may be selected from the group consisting of compounds of formulae (Ia) to (XIIa):

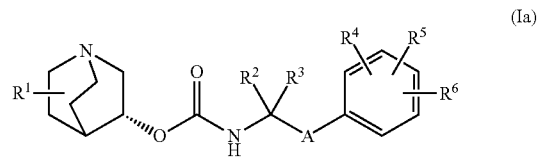

(Ia)

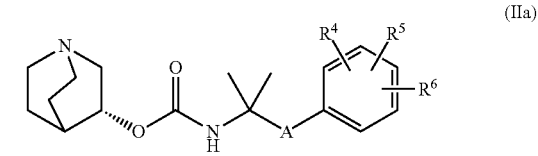

(IIa)

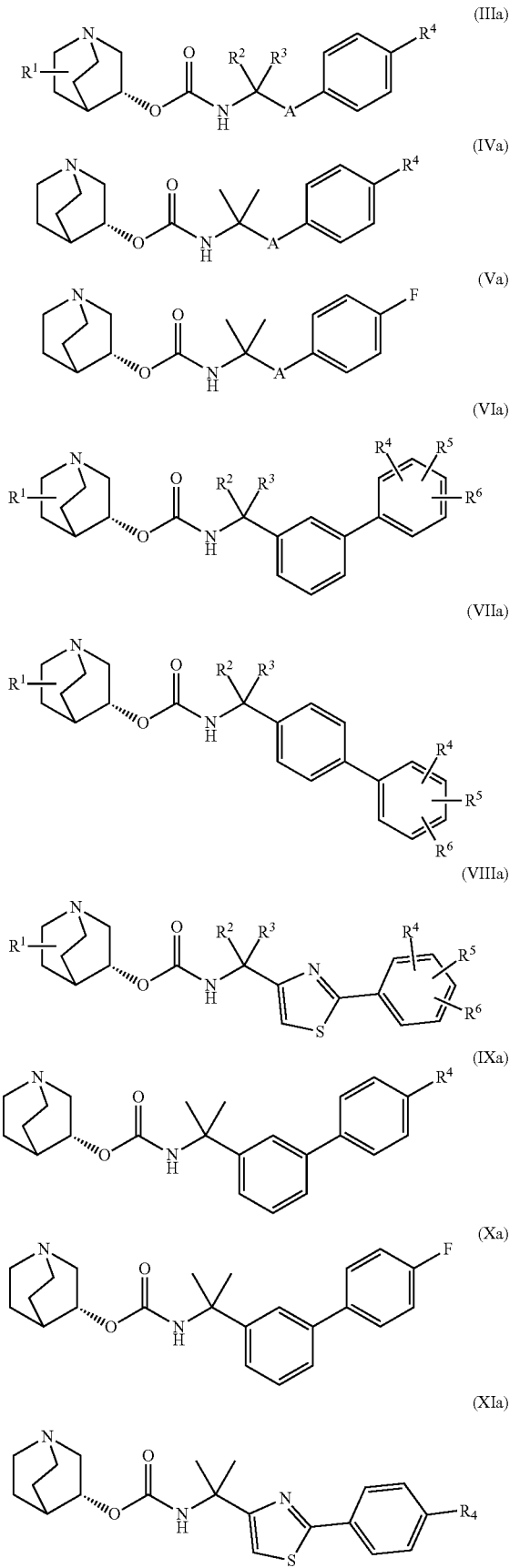
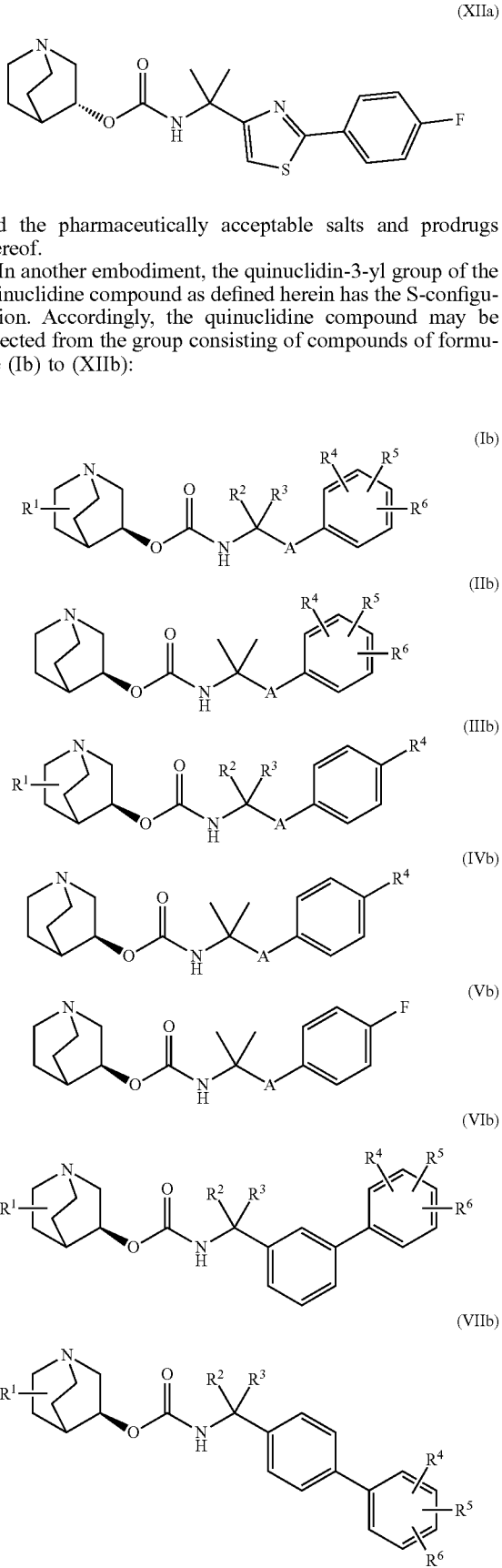
and the pharmaceutically acceptable salts and prodrugs thereof.
In another embodiment, the quinuclidin-3-yl group of the quinuclidine compound as defined herein has the S-configuration. Accordingly, the quinuclidine compound may be selected from the group consisting of compounds of formulae (Ib) to (XIIb):

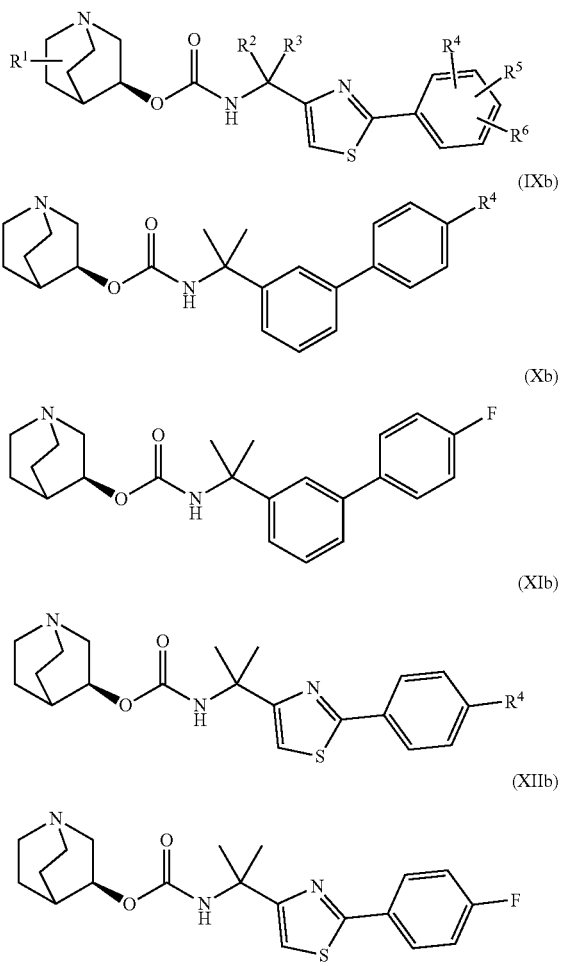

and the pharmaceutically acceptable salts and prodrugs thereof.

In one embodiment the quinuclidine compound is a compound of formula (Xb) or a pharmaceutically acceptable salt or prodrug thereof. In another embodiment the quinuclidine compound is a compound of formula (XIIb) or a pharmaceutically acceptable salt or prodrug thereof.

In one embodiment, the quinuclidin-3-yl group of the quinuclidine compound as defined herein exists in a mixture of isomers having the R- and S-configurations. For example, the quinuclidine compound may be a mixture of compounds selected from the group consisting of compounds of formulae (Ia) and (Ib), (IIa) and (IIb), (IIIa) and (IIIb), (IVa) and (IVb), (Va) and (Vb), (VIa) and (VIb), (VIIa) and (VIIb), (VIIIa) and (VIIIb), (Ixa) and (Ixb), (Xa) and (Xb), (XIa) and (XIb), and (XIIa) and (XIIb), and the pharmaceutically acceptable salts and prodrugs thereof. In one embodiment the quinuclidine compound is present as a racemic mixture, e.g., the R- and S-isomers of the quinuclidin-3-yl group are present in about equal amounts. In another embodiment the quinuclidine compound is present as a mixture of isomers having the R- and S-configurations, wherein the R- and S-isomers are present in different amounts. In one embodiment the S-isomer is present in an enantiomeric excess of at least about 5%, 10%, 25%, 40%, 70%, 80%, 90%, 95%, 97%, 98%, or 99%, e.g., about 100%. In another embodiment, the R-isomer is present in an enantiomeric excess of at least about 5%, 10%, 25%, 40%, 70%, 80%, 90%, 95%, 97%, 98%, or 99%, e.g., about 100%.

Methods for preparing enantioenriched and/or enantiopure quinuclidine compounds would be apparent to the person of skill in the art based on the present disclosure.

The compounds presently disclosed can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, all tautomers are within the scope of the present disclosure.

Atropisomers are also within the scope of the present disclosure. Atropisomers refer to compounds that can be separated into rotationally restricted isomers.

Other Forms

The present disclosure further embraces hydrates, solvates, and polymorphs of Compound 1 and 1.1-1.75. Pharmaceutically acceptable hydrates, solvates, and polymorphs of the quinuclidine compounds described herein are within the scope of the present disclosure. Quinuclidine compounds as described herein may be in an amorphous form and/or in one or more crystalline forms.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine, and chlorine, such as $^2H$, $^3H$, $^{13}C$, $^{14}C$, $^{15}N$, $^{18}O$, $^{17}O$, $^{31}P$, $^{32}P$, $S$, $^{18}F$, and $^{36}Cl$, respectively.

Medical Indications

The quinuclidine compounds, and pharmaceutical compositions containing them, described herein are useful in therapy, in particular in the therapeutic treatment of neurological disorders, including dementia and gait disorders, e.g., in a patient having a disease such as Gaucher disease. Subjects to be treated according to the methods described herein include vertebrates, such as mammals. In particular embodiments the mammal is a human patient.

As discussed above, one of the hallmarks of glycogen storage diseases is the abnormal accumulation of various glycolipids or glycosphingolipids in cells of the body. This accumulation is both a cause of the observable symptoms and signs of the disease, as well as a diagnostic marker evidencing the presence and/or progression of the disease. As used herein the phrase "marked accumulation" in reference to the measurement of GL-3, GL-1, and other biomarkers in plasma, skin, or other soft tissues means an accumulation of more than 25% over the maximum normal concentration of said compound. In some embodiments, "marked accumulation" means more than 50% over the maximum normal concentration of said compound.

In a first aspect, the present invention provides a method (Method 1) for treating or preventing cognitive dysfunction and/or gait abnormalities, including ataxia, associated with a lysosome storage disease, in a subject, such as a subject in need thereof, the method comprising administering to the subject an effective amount of a quinuclidine compound as described herein, e.g., a compound according to Formula (I) or any of (II)-(XII), (Ia)-(XIIa), or (Ib)-(XIIb), or any of Compounds 1 or 1.1 to 1.75. Also provided is a quinuclidine compound as described herein, e.g., a compound according to Formula (I) or any of (II)-(XII), (Ia)-(XIIa), or (Ib)-(XIIb), or any of Compounds 1 or 1.1 to 1.75, for use in a method for treating or preventing cognitive dysfunction and/or gait abnormalities, including ataxia, associated with a lysosome storage disease, in a subject in need thereof, e.g., for use in Method 1 or any of 1.1-1.64. Further provided is the use of a quinuclidine compound as described herein, e.g., a compound according to Formula (I) or any of (II)-(XII), (Ia)-(XIIa), or (Ib)-(XIIb), or any of Compounds 1 or 1.1 to 1.75, in the manufacture of a medicament for use in a method of treating or preventing cognitive dysfunction and/or gait abnormalities, including ataxia, associated with a lysosome storage disease, in a subject in need thereof, e.g., in the manufacture of a medicament for use in Method 1 or any of 1.1-1.64.

In particular further embodiments of Method 1, the present disclosure provides:

1.1. Method 1, wherein the method comprises administering to the subject an effective amount of a compound according to Formula (I) or any of (II)-(XII), (Ia)-(XIIa), or (Ib)-(XIIb), or any of Compounds 1 or any of 1.1 to 1.75;
1.2. Method 1, wherein the method comprises administering to the subject an effective amount of Compound 1 or any one or more of Compounds 1.1 to 1.75;
1.3. Method 1 or any of 1.1-1.2, wherein the method comprises administering to the subject an effective amount of a pharmaceutical composition comprising the compound according to Formula (I) or any of (II)-(XII), (Ia)-(XIIa), or (Ib)-(XIIb), or any of Compounds 1 or any of 1.1 to 1.75;
1.4. Method 1 or any of 1.1-1.2, wherein the method comprises administering to the subject an effective amount of a pharmaceutical composition comprising the Compound 1 or any one or more of Compounds 1.1 to 1.75;
1.5. Method 1.3 or 1.4, wherein the pharmaceutical composition further comprises at least one pharmaceutically acceptable excipient, as described herein;
1.6. Method 1 or any of 1.1-1.5, wherein the method comprising administering a pharmaceutical dosage form comprising an effective amount of the compound or an effective amount of the pharmaceutical composition;
1.7. Method 1.6, wherein the dosage form is an oral dosage form (e.g., a pill, capsule, caplet, tablet, dragee, powder, granule, film, lozenge, or liquid);
1.8. Method 1.7, wherein the dosage form is a chewable tablet;
1.9. Method 1.6, wherein the dosage form is a parenteral dosage form (e.g., wherein the pharmaceutical composition is formulated for injection);
1.10. Method 1.9, wherein the injection is intravenous, intramuscular, intrathecal, or subcutaneous injection, optionally a sterile injection;
1.11. Method 1.6, wherein the dosage form is a topical or rectal dosage form;
1.12. Method 1.6, wherein the dosage form is an intranasal dosage form (e.g., an aerosol);
1.13. Method 1 or any of 1.1 to 1.12, wherein the method further comprises concurrently administering a second active agent, e.g., a second compound capable of treating or preventing cognitive dysfunction and/or gait abnormalities in a patient in need thereof, as described herein;
1.14. Method 1.13, wherein the second active agent is administrated in the same pharmaceutical composition or dosage form as the quinuclidine compound;
1.15. Method 1.13 or 1.14, wherein the second active agent is a GCS inhibitor (e.g., miglustat or eliglustat);
1.16. Method 1, or any of 1.1-1.15, wherein the subject is a mammalian animal;
1.17. Method 1.16, wherein the subject is a primate animal;
1.18. Method 1.17, wherein the subject is a human;
1.19. Method 1 or any of 1.1-1.18, wherein the ataxia is a cerebellar ataxia;
1.20. Method 1.19, wherein the ataxia shows symptoms selected from gait instability, asthenia, asynergy, delayed reaction time, dyschronometria, dysarthria, dysphagia, hypotonia, dysmetria, hypometria, hypermetria, dysdiadochokinesia, speech slurring, voice tremor, ataxic respiration, postural instability, and combinations thereof, for example, wherein the primary ataxic deficit is a gait instability;
1.21. Method 1.19 or 1.20, wherein the subject has a baseline ataxia of at least 0.5 on the Scale for Assessment and Rating of Ataxia (SARA) scale at the initiation of therapy according to the method, e.g., a baseline SARA score of at least 1, or at least 2, or at least 3, or at least 4, or at least 5, or at least 10, or at least 20;
1.22. Method 1, or any of 1.1-1.21, wherein the cognitive dysfunction is a dementia;
1.23. Method 1.22, wherein the dementia shows signs of defects in visual search speed, scanning speed of processing, mental flexibility, and/or executive functioning, e.g., as evidence by a TMT-A of greater than 30 seconds, or greater than 45 seconds, or greater than 60 seconds, and/or a TMT-B of greater than 70 seconds, or greater than 90 seconds, or greater than 120 seconds, or greater than 150 seconds, or greater than 180 seconds, and/or wherein TMT-B minus TMT-A is greater than 40 seconds, or greater than 60 seconds, or greater than 90 seconds, or greater than 120 seconds;
1.24. Method 1, or any of 1.1-1.23, wherein the subject has Gaucher disease Type 3;
1.25. Method 1, or any of 1.1-1.24, wherein the subject has Niemann-Pick disease Type C;
1.26. Method 1, or any of 1.1-1.24, wherein the subject has a GM2-gangliosidosis (e.g., Tay-Sachs disease, Sandhoff disease, or GM2 gangliosidosis AB variant);
1.27. Method 1, or any of 1.1-1.24, wherein the subject is diagnosed with a mutation in the gene GBA1;
1.28. Method 1, or any of 1.1-1.24, wherein the subject is diagnosed with a mutation in the genes NPC1 and/or NPC2;
1.29. Method 1, or any of 1.1-1.24, wherein the subject is diagnosed with a mutation in the gene HEXA (encoding hexosaminidase A) and/or a mutation in the gene HEXB (encoding hexosaminidase B) and/or a mutation in the gene GM2A (encoding the GM2 ganglioside activator protein);
1.30. Method 1, or any of 1.1-1.29, wherein the subject is diagnosed with Parkinson's disease;
1.31. Method 1, or any of 1.1-1.30, wherein the subject undergoes concurrent treatment with enzyme replacement therapy (ERT), e.g., using a glucocerebrosidase (e.g., imiglucerase, velaglucerase, or taliglucerase), optionally wherein in each of such enzyme is a recombinant enzyme;
1.32. Method 1.31, wherein the subject undergoes concurrent treatment with one or more of imiglucerase, velaglucerase (e.g., velaglucerase alfa), and taliglucerase (e.g., taliglucerase alfa);

1.33. Method 1.32, wherein the subject undergoes concurrent treatment with imiglucerase;

1.34. Method 1.33, wherein the subject undergoes concurrent treatment with imiglucerase at a dosage of from 2.5 units/kg body weight to 80 units/kg body weight every 1 to 3 weeks, e.g., 40 to 60 units/kg body weight every 2 weeks (1 unit of imiglucerase is the amount of enzyme that catalyzes the hydrolysis of 1 micromole of the synthetic substrate p-nitrophenyl-β-D-glucopyranoside per minute at 37° C.);

1.35. Method 1.34, wherein the subject's dosage of imiglucerase at each administration (e.g., every 1 to 3 weeks, e.g., every 2 weeks) is administered as an intravenous (IV) infusion over a period of 1-3 hours (e.g., 1-2 hours);

1.36. Method 1 or any of 1.1-1.35, wherein the subject has been administered enzyme replacement therapy (e.g., imiglucerase, velaglucerase, and/or taliglucerase) prior to the initiation of treatment with the compound according to Formula (I) (or any of (II)-(XII), (Ia)-(XIIa), or (Ib)-(XIIb), or any of Compounds 1 or 1.1 to 1.75);

1.37. Method 1.36, wherein the subject has been administered imiglucerase therapy for at least 6 months prior to beginning therapy with the compound according to Formula (I) (or any of (II)-(XII), (Ia)-(XIIa), or (Ib)-(XIIb), or any of Compounds 1 or 1.1 to 1.75), for example, at least 12 months (1 year), or at least 18 months, or at least 2 years, or at least 3 years.

1.38. Method 1.36 or 1.37, wherein the subject has been administered imiglucerase therapy for at least 6 months at a stable dose prior to beginning therapy with the compound according to Formula (I) (or any of (II)-(XII), (Ia)-(XIIa), or (Ib)-(XIIb), or any of Compounds 1 or 1.1 to 1.75);

1.39. Method 1 or any of 1.1-1.38, wherein the method further comprises the step of transitioning the subject from ERT therapy (e.g., imiglucerase, velaglucerase, or taliglucerase) to treatment with the compound according to Formula (I) (or any of (II)-(XII), (Ia)-(XIIa), or (Ib)-(XIIb), or any of Compounds 1 or 1.1 to 1.75);

1.40. Method 1 or any of 1.1-1.39, wherein the subject has a hemoglobin level of at least 11 g/dL for females and at least 12 g/dL for males;

1.41. Method 1, or any of 1.1-1.40, wherein the subject has a platelet count of at least 100,000/cubic millimeter;

1.42. Method 1, or any of 1.1-1.41, wherein the subject has a splenic volume of less than 10 multiples of normal (MN) and/or a hepatic volume of less than 1.5 MN;

1.43. Method 1, or any of 1.1-1.42, wherein the subject is diagnosed with a concurrent dementia, e.g., Alzheimer's disease or Parkinson's disease;

1.44. Method 1, or any of 1.1-1.43, wherein the subject is at least 18 years of age (e.g., 18-30 years of age) at the start of treatment with the compound according to Formula (I) (or any of (II)-(XII), (Ia)-(XIIa), or (Ib)-(XIIb), or any of Compounds 1 or 1.1 to 1.75);

1.45. Method 1, or any of 1.1-1.44, wherein the subject has a glucosylceramide (GL1) concentration of 4.4-11.1 ng/mL in cerebrospinal fluid (CSF) and 4.9-8.3 g/mL in plasma;

1.46. Method 1, or any of 1.1-1.45, wherein the subject has a glucosylsphingosine (lyso-GL1) concentration of 20.1-67.6 pg/mL in CSF and 8.8-159.0 ng/mL in plasma;

1.47. Method 1, or any of 1.1-1.46, wherein the subject is administered a daily dose of about 1 mg to about 150 mg of the compound according to Formula (I) (or any of (II)-(XII), (Ia)-(XIIa), or (Ib)-(XIIb), or any of Compounds 1 or 1.1 to 1.75), e.g., from 5 to 50 mg, or from 10 to 40 mg, or from 10 to 30 mg, or from 10 to 20 mg, or from 20 to 30 mg, or from 30 to 40 mg, or from 40 to 50 mg, or from 5 to 25 mg, or from 20 to 50 mg, or from 5 to 15 mg, or from 15 to 30 mg, or about 15 mg, or selected from 2, 5, 15, 25, 50, 100, or 150 mg;

1.48. Method 1, or any of 1.1-1.47, wherein the subject is a human adult patient, e.g., of an age from 18 to 80 years old, e.g., from 18 to 60 years old, or from 18 to years old, or from 18 to 30 years old, or from 18 to 25 years old;

1.49. Method 1, or any of 1.1-1.47, wherein the subject is a human pediatric patient, e.g., of an age from 0 to 18 years old, e.g., from 1 to 15 years old, or from 1 to 5 years old, or from 5 to 10 years old, or from 10 to 15 years old, or from 10 to 18 years old;

1.50. Method 1, or any of 1.1-1.49, wherein the method is effective to provide a reduction on the SARA ataxia scale of at least 0.5, e.g., a SARA score reduction of at least 1, or at least 2, or at least 3, or at least 5, or at least 10; or wherein the method is effective to reduce the SARA score to between 0.00 and 3.00, or between 0.00 and 2.00, or between 0.00 and 1.50, or between 0.00 and 1.00, or between 0.00 and 0.50.

1.51. Method 1, or any of 1.1-1.50, wherein the method is effective to improve cognitive ability or reduce cognitive deficits, e.g., as measured by a reduction in the time taken to complete the trail-making test (TMT), TMT-A, and/or TMT-B, a reduction in the difference between TMT-A time and TMT-B time (TMT-A−TMT-B), for example, a reduction of at least 10%, or at least 20%, or at least 30%, or at least 40%, or at least 50% (e.g., wherein TMT-A decreases by 5-20%, and/or TMT-B decreases by 25-30%, and/or [TMT-A−TMT-B] decreases by 25-30%);

1.52. Method 1, or any of 1.1-1.51, wherein the method results in reduction in glucosylceramide concentration in CSF and/or in plasma of at least 30% after 6 months of treatment, e.g., at least 40%, at least 50%, at least 60%, or at least 70%;

1.53. Method 1, or any of 1.1-1.52, wherein the method results in an increase in glucosylsphingosine concentration in CSF and/or in plasma of at least 30% after 6 months of treatment, e.g., at least 40%, at least 50%, at least 60%, or at least 70%;

1.54. Method 1, or any of 1.1-1.53, wherein the method results in a statistically or clinically unchanged Modified Severity Scoring Tool (mSST) value for neurological disease after 6 months of treatment;

1.55. Method 1, or any of 1.1-1.54, wherein the method results in increased blood flow in the brain (e.g., in one or more of the frontal, occipital, parietal, or temporal lobes), for example, as shown by fMRI imaging;

1.56. Method 1, or any of 1.1-1.54, wherein the method results in increased nodal connectivity in the brain (e.g., between posterior and anterior aspects of the brain, and/or between occipital-parietal structures and frontal, temporal, and/or limbic structures), for example, as shown by fMRI imaging;
1.57. Method 1, or any of 1.1-1.56, wherein the compound according to Formula (I) (or any of (II)-(XII), (Ia)-(XIIa), or (Ib)-(XIIb), or any of Compounds 1 or 1.1 to 1.75), or pharmaceutically acceptable salt or prodrug thereof, is administered by systemic administration, e.g., via a parenteral route or a non-parenteral route;
1.58. Method 1.57, wherein the route of administration is oral (enteral);
1.59. Method 1.57, wherein the route of administration is parenteral, e.g., by injection, such as by intravenous injection;
1.60. Method 1, or any of 1.1-1.59, wherein the compound according to Formula (I) (or any of (II)-(XII), (Ia)-(XIIa), or (Ib)-(XIIb), or any of Compounds 1 or 1.1 to 1.75), or pharmaceutically acceptable salt or prodrug thereof, is administered by local administration, e.g., by topical administration;
1.61. Method 1, or any of 1.1-1.60, wherein the compound is (S)-quinuclidin-3-yl (2-(2-(4-fluorophenyl)thiazol-4-yl)propan-2-yl)carbamate or quinuclidin-3-yl (2-(4'-fluoro-[1,1'-biphenyl]-3-yl)propan-2-yl)carbamate;
1.62. Method 1.61, wherein the dosage of the compound is 15 mg/day orally administered;
1.63. Method 1.62, wherein the dosage of the compound is 15 mg/day in a single oral dose;
1.64. Method 1, or any of 1.1-1.63, wherein the subject is administered a single daily dose of 5 mg, 10 mg, 15 mg, or 20 mg of the compound, e.g., of (S)-quinuclidin-3-yl (2-(2-(4-fluorophenyl)thiazol-4-yl)propan-2-yl)carbamate, optionally in malate salt acid addition salt form.

In some embodiments of the present disclosure, a subject or subject is diagnosed with having a particular disease or disorder and is also diagnosed to have a particular genetic mutation, for example, one that is known to be a cause of the disease or disorder in question, although it often cannot be proven that a particular patient's disease or disorder is caused by the particular mutation that a person has been diagnosed with having. As used in this manner, the term "diagnosed to have a particular genetic mutation" means that a subject or patient has been tested, e.g., by DNA or RNA sequencing, protein profiling, or other suitable means, and found to have the mutation in question. However, as discussed further below, many genetic diseases and disorders can have multiple genetic causes (e.g., mutations), and patients may have multiple mutations each of which may, under some circumstances, be sufficient to cause the disease or disorder, without it being subject to proof that a particular mutation causes a particular disease or disorder in a particular patient.

The methods according to Method 1 et seq. may be beneficial for subjects who have been diagnosed with a lysosomal storage disease, such as Gaucher Type 3 or Niemann-Pick Type C, but who are not yet experiencing the cognitive and/or ataxic symptoms associated with the disease state. The methods according to Method 1 et seq. may also be beneficial for subjects who are at risk of developing a lysosomal storage disease, such as Gaucher Type 3 or Niemann-Pick Type C, due to, for example, a mutation in the subject or the subject's family lineage known to cause such disease. Therefore, in some embodiments of the methods described herein, the subject has been diagnosed as being at risk of developing said disease or disorder, and the method prevents or delays the onset and/or development of the cognitive and/or ataxic symptoms of the disease or disorder in the subject. In some embodiments, the subject has been diagnosed as being at risk of developing said disease or disorder by virtue of having a mutation in a gene as described herein.

In a second aspect, the present invention provides a method (Method 2) for enhancing neuronal connectivity within the brain of a subject, such as in a subject in need thereof, the method comprising administering to the subject an effective amount of a quinuclidine compound as described herein, e.g., a compound according to Formula (I) or any of (II)-(XII), (Ia)-(XIIa), or (Ib)-(XIIb), or any of Compounds 1 or 1.1 to 1.75. Also provided is a quinuclidine compound as described herein, e.g., a compound according to Formula (I) or any of (II)-(XII), (Ia)-(XIIa), or (Ib)-(XIIb), or any of Compounds 1 or 1.1 to 1.75, for enhancing neuronal connectivity within the brain of a subject, e.g., for use in Method 2 or any of 2.1-2.67. Further provided is the use of a quinuclidine compound as described herein, e.g., a compound according to Formula (I) or any of (II)-(XII), (Ia)-(XIIa), or (Ib)-(XIIb), or any of Compounds 1 or 1.1 to 1.75, in the manufacture of a medicament for enhancing neuronal connectivity within the brain of a subject, e.g., in the manufacture of a medicament for use in Method 2 or any of 2.1-2.67.

In particular further embodiments of Method 2, the present disclosure provides:
2.1. Method 2, wherein the method comprises administering to the subject an effective amount of a compound according to Formula (I) or any of (II)-(XII), (Ia)-(XIIa), or (Ib)-(XIIb), or any of Compounds 1 or any of 1.1 to 1.75;
2.2. Method 2, wherein the method comprises administering to the subject an effective amount of Compound 1 or any one or more of Compounds 1.1 to 1.75;
2.3. Method 2 or any of 2.1-2.2, wherein the method comprises administering to the subject an effective amount of a pharmaceutical composition comprising the compound according to Formula (I) or any of (II)-(XII), (Ia)-(XIIa), or (Ib)-(XIIb), or any of Compounds 1 or any of 1.1 to 1.75;
2.4. Method 2 or any of 2.1-2.2, wherein the method comprises administering to the subject an effective amount of a pharmaceutical composition comprising the Compound 1 or any one or more of Compounds 1.1 to 1.75;
2.5. Method 2.3 or 2.4, wherein the pharmaceutical composition further comprises at least one pharmaceutically acceptable excipient, as described herein;
2.6. Method 2 or any of 2.1-2.5, wherein the method comprising administering a pharmaceutical dosage form comprising an effective amount of the compound or an effective amount of the pharmaceutical composition;
2.7. Method 2.6, wherein the dosage form is an oral dosage form (e.g., a pill, capsule, caplet, tablet, dragee, powder, granule, film, lozenge, or liquid);
2.8. Method 2.7, wherein the dosage form is a chewable tablet;
2.9. Method 2.6, wherein the dosage form is a parenteral dosage form (e.g., wherein the pharmaceutical composition is formulated for injection);
2.10. Method 2.9, wherein the injection is intravenous, intramuscular, intrathecal, or subcutaneous injection, optionally a sterile injection;

2.11. Method 2.6, wherein the dosage form is a topical or rectal dosage form;

2.12. Method 2.6, wherein the dosage form is an intranasal dosage form (e.g., an aerosol);

2.13. Method 2 or any of 2.1 to 2.12, wherein the method further comprises concurrently administering a second active agent, e.g., a second compound capable of reducing levels of glycosylceramide in a patient in need thereof, as described herein;

2.14. Method 2.13, wherein the second active agent is administrated in the same pharmaceutical composition or dosage form as the quinuclidine compound;

2.15. Method 2.13 or 2.14, wherein the second active agent is a GCS inhibitor (e.g., miglustat or eliglustat);

2.16. Method 2, or any of 2.1-2.15, wherein the subject is a mammalian animal;

2.17. Method 2.16, wherein the subject is a primate animal;

2.18. Method 2.17, wherein the subject is a human;

2.19. Method 2 or any of 2.1-2.18, wherein the subject has ataxia, for example, symptoms selected from gait instability, asthenia, asynergy, delayed reaction time, dyschronometria, dysarthria, dysphagia, hypotonia, dysmetria, hypometria, hypermetria, dysdiadochokinesia, speech slurring, voice tremor, ataxic respiration, postural instability, and combinations thereof, for example, wherein the primary ataxic deficit is a gait instability;

2.20. Method 2.19, wherein the subject has a baseline ataxia of at least 0.5 on the Scale for Assessment and Rating of Ataxia (SARA) scale at the initiation of therapy according to the method, e.g., a baseline SARA score of at least 1, or at least 2, or at least 3, or at least 4, or at least 5, or at least 10, or at least 20;

2.21. Method 2 or any of 2.1-2.20, wherein the subject has cognitive dysfunction (e.g., dementia);

2.22. Method 2.21, wherein the cognitive dysfunction is a dementia;

2.23. Method 2.22, wherein the dementia shows signs of defects in visual search speed, scanning speed of processing, mental flexibility and/or executive functioning, e.g., as evidence by a TMT-A of greater than 30 seconds, or greater than 45 seconds, or greater than 60 seconds, and/or a TMT-B of greater than 70 seconds, or greater than 90 seconds, or greater than 120 seconds, or greater than 150 seconds, or greater than 180 seconds, and/or wherein TMT-B minus TMT-A is greater than 40 seconds, or greater than 60 seconds, or greater than 90 seconds, or greater than 120 seconds;

2.24. Method 2, or any of 2.1-2.23, wherein the subject has Gaucher disease Type 3;

2.25. Method 2, or any of 2.1-2.24, wherein the subject has Niemann-Pick disease Type C;

2.26. Method 2, or any of 2.1-2.24, wherein the subject has a GM2-gangliosidosis (e.g., Tay-Sachs disease, Sandhoff disease, or GM2 gangliosidosis AB variant);

2.27. Method 2, or any of 2.1-2.24, wherein the subject is diagnosed with a mutation in the gene GBA1;

2.28. Method 2, or any of 2.1-2.24, wherein the subject is diagnosed with a mutation in the genes NPC1 and/or NPC2;

2.29. Method 2, or any of 2.1-2.24, wherein the subject is diagnosed with a mutation in the gene HEXA (encoding hexosaminidase A) and/or a mutation in the gene HEXB (encoding hexosaminidase B) and/or a mutation in the gene GM2A (encoding the GM2 ganglioside activator protein);

2.30. Method 2, or any of 2.1-2.29, wherein the subject is diagnosed with Parkinson's disease;

2.31. Method 2, or any of 2.1-2.30, wherein the subject undergoes concurrent treatment with enzyme replacement therapy (ERT), e.g., using a glucocerebrosidase (e.g., imiglucerase, velaglucerase, or taliglucerase), optionally wherein in each of such enzyme is a recombinant enzyme;

2.32. Method 2.31, wherein the subject undergoes concurrent treatment with one or more of imiglucerase, velaglucerase (e.g., velaglucerase alfa), and taliglucerase (e.g., taliglucerase alfa);

2.33. Method 2.32, wherein the subject undergoes concurrent treatment with imiglucerase;

2.34. Method 2.33, wherein the subject undergoes concurrent treatment with imiglucerase at a dosage of from 2.5 units/kg body weight to 80 units/kg body weight every 1 to 3 weeks, e.g., 40 to 60 units/kg body weight every 2 weeks (1 unit of imiglucerase is the amount of enzyme that catalyzes the hydrolysis of 1 micromole of the synthetic substrate p-nitrophenyl-β-D-glucopyranoside per minute at 37° C.);

2.35. Method 2.34, wherein the subject's dosage of imiglucerase at each administration (e.g., every 1 to 3 weeks, e.g., every 2 weeks) is administered as an intravenous (IV) infusion over a period of 1-3 hours (e.g., 1-2 hours);

2.36. Method 2 or any of 2.1-2.35, wherein the subject has been administered enzyme replacement therapy (e.g., imiglucerase, velaglucerase, and/or taliglucerase) prior to the initiation of treatment with the compound according to Formula (I) (or any of (II)-(XII), (Ia)-(XIIa), or (Ib)-(XIIb), or any of Compounds 1 or 1.1 to 1.75);

2.37. Method 2.36, wherein the subject has been administered imiglucerase therapy for at least 6 months prior to beginning therapy with the compound according to Formula (I) (or any of (II)-(XII), (Ia)-(XIIa), or (Ib)-(XIIb), or any of Compounds 1 or 1.1 to 1.75), for example, at least 12 months (1 year), or at least 18 months, or at least 2 years, or at least 3 years.

2.38. Method 2.36 or 2.37, wherein the subject has been administered imiglucerase therapy for at least 6 months at a stable dose prior to beginning therapy with the compound according to Formula (I) (or any of (II)-(XII), (Ia)-(XIIa), or (Ib)-(XIIb), or any of Compounds 1 or 1.1 to 1.75);

2.39. Method 2 or any of 2.1-2.38, wherein the method further comprises the step of transitioning the subject from ERT therapy (e.g., imiglucerase, velaglucerase, or taliglucerase) to treatment with the compound according to Formula (I) (or any of (II)-(XII), (Ia)-(XIIa), or (Ib)-(XIIb), or any of Compounds 1 or 1.1 to 1.75);

2.40. Method 2 or any of 2.1-2.39, wherein the subject has a hemoglobin level of at least 11 g/dL for females and at least 12 g/dL for males;

2.41. Method 2, or any of 2.1-2.40, wherein the subject has a platelet count of at least 100,000/cubic millimeter;

2.42. Method 2, or any of 2.1-2.41, wherein the subject has a splenic volume of less than 10 multiples of normal (MN) and/or a hepatic volume of less than 1.5 MN;

2.43. Method 2, or any of 2.1-2.42, wherein the subject is diagnosed with a concurrent dementia, e.g., Alzheimer's disease or Parkinson's disease;

2.44. Method 2, or any of 2.1-2.43, wherein the subject is at least 18 years of age (e.g., 18-30 years of age) at the start of treatment with the compound according to Formula (I) (or any of (II)-(XII), (Ia)-(XIIa), or (Ib)-(XIIb), or any of Compounds 1 or 1.1 to 1.75);

2.45. Method 2, or any of 2.1-2.44, wherein the subject has a glucosylceramide (GL1) concentration of 4.4-11.1 ng/mL in cerebrospinal fluid (CSF) and 4.9-8.3 g/mL in plasma;

2.46. Method 2, or any of 2.1-2.45, wherein the subject has a glucosylsphingosine (lyso-GL1) concentration of 20.1-67.6 pg/mL in CSF and 8.8-159.0 ng/mL in plasma;

2.47. Method 2, or any of 2.1-2.46, wherein the subject is administered a daily dose of about 1 mg to about 150 mg of the compound according to Formula (I) (or any of (II)-(XII), (Ia)-(XIIa), or (Ib)-(XIIb), or any of Compounds 1 or 1.1 to 1.75), e.g., from 5 to 50 mg, or from 10 to 40 mg, or from 10 to 30 mg, or from 10 to 20 mg, or from 20 to 30 mg, or from 30 to 40 mg, or from 40 to 50 mg, or from 5 to 25 mg, or from 20 to 50 mg, or from 5 to 15 mg, or from 15 to 30 mg, or about 15 mg, or selected from 2, 5, 15, 25, 50, 100, or 150 mg;

2.48. Method 2, or any of 2.1-2.47, wherein the subject is a human adult patient, e.g., of an age from 18 to 80 years old, e.g., from 18 to 60 years old, or from 18 to years old, or from 18 to 30 years old, or from 18 to 25 years old;

2.49. Method 2, or any of 2.1-2.47, wherein the subject is a human pediatric patient, e.g., of an age from 0 to 18 years old, e.g., from 1 to 15 years old, or from 1 to 5 years old, or from 5 to 10 years old, or from 10 to 15 years old, or from 10 to 18 years old;

2.50. Method 2, or any of 2.1-2.49, wherein the method is effective to provide a reduction on the SARA ataxia scale of at least 0.5, e.g., a SARA score reduction of at least 1, or at least 2, or at least 3, or at least 5, or at least 10; or wherein the method is effective to reduce the SARA score to between 0.00 and 3.00, or between 0.00 and 2.00, or between 0.00 and 1.50, or between 0.00 and 1.00, or between 0.00 and 0.50.

2.51. Method 2, or any of 2.1-2.50, wherein the method is effective to improve cognitive ability or reduce cognitive deficits, e.g., as measured by a reduction in the time taken to complete the trail-making test (TMT), TMT-A, and/or TMT-B, a reduction in the difference between TMT-A time and TMT-B time (TMT-A−TMT-B), for example, a reduction of at least 10%, or at least 20%, or at least 30%, or at least 40%, or at least 50% (e.g., wherein TMT-A decreases by 5-20%, and/or TMT-B decreases by 25-30%, and/or [TMT-A−TMT-B] decreases by 25-30%);

2.52. Method 2, or any of 2.1-2.51, wherein the method results in reduction in glucosylceramide concentration in CSF and/or in plasma of at least 30% after 6 months of treatment, e.g., at least 40%, at least 50%, at least 60%, or at least 70%;

2.53. Method 2, or any of 2.1-2.52, wherein the method results in an increase in glucosylsphingosine concentration in CSF and/or in plasma of at least 30% after 6 months of treatment, e.g., at least 40%, at least 50%, at least 60%, or at least 70%;

2.54. Method 2, or any of 2.1-2.53, wherein the method results in a statistically or clinically unchanged Modified Severity Scoring Tool (mSST) value for neurological disease after 6 months of treatment;

2.55. Method 2, or any of 2.1-2.54, wherein the method results in increased blood flow in the brain (e.g., in one or more of the frontal, occipital, parietal, or temporal lobes), for example, as shown by fMRI imaging;

2.56. Method 2, or any of 2.1-2.54, wherein the method results in increased nodal connectivity in the brain (e.g., between posterior and anterior aspects of the brain, and/or between occipital-parietal structures and frontal, temporal, and/or limbic structures, for example, as shown by fMRI imaging);

2.57. Method 2, or any of 2.1-2.56, wherein the method results in enhanced connectivity in brain regions associated with executive function;

2.58. Method 2, or any of 2.1-2.57, wherein the method results in resting-state functional networks with improved connectivity between default mode and medial and frontal networks;

2.59. Method 2, or any of 2.1-2.58, wherein the method results in enhanced connectivity between RSNs 1, 2, and 3 (perception-vision, cognition-language-orthography, cognition space) and RSNs 6, 7 and 8 (sensorimotor, auditory, and executive control);

2.60. Method 2, or any of 2.1-2.59, wherein the compound according to Formula (I) (or any of (II)-(XII), (Ia)-(XIIa), or (Ib)-(XIIb), or any of Compounds 1 or 1.1 to 1.75), or pharmaceutically acceptable salt or prodrug thereof, is administered by systemic administration, e.g., via a parenteral route or a non-parenteral route;

2.61. Method 2.60, wherein the route of administration is oral (enteral);

2.62. Method 2.60, wherein the route of administration is parenteral, e.g., by injection, such as by intravenous injection;

2.63. Method 2, or any of 2.1-2.62, wherein the compound according to Formula (I) (or any of (II)-(XII), (Ia)-(XIIa), or (Ib)-(XIIb), or any of Compounds 1 or 1.1 to 1.75), or pharmaceutically acceptable salt or prodrug thereof, is administered by local administration, e.g., by topical administration;

2.64. Method 2, or any of 2.1-2.63, wherein the compound is (S)-quinuclidin-3-yl (2-(2-(4-fluorophenyl)thiazol-4-yl)propan-2-yl)carbamate or quinuclidin-3-yl (2-(4'-fluoro-[1,1'-biphenyl]-3-yl)propan-2-yl)carbamate;

2.65. Method 2.64, wherein the dosage of the compound is 15 mg/day orally administered;

2.66. Method 2.65, wherein the dosage of the compound is 15 mg/day in a single oral dose;

2.67. Method 2, or any of 2.1-2.66, wherein the subject is administered a single daily dose of 5 mg, 10 mg, 15 mg, or 20 mg of the compound, e.g., of (S)-quinuclidin-3-yl (2-(2-(4-fluorophenyl)thiazol-4-yl)propan-2-yl)carbamate, optionally in malate salt acid addition salt form.

The methods according to Method 2 et seq. may be beneficial for subjects who have been diagnosed with a lysosomal storage disease, such as Gaucher Type 3 or Niemann-Pick Type C, but who are not yet experiencing the cognitive and/or ataxic symptoms associated with the disease state. The methods according to Method 2 et seq. may also be beneficial for subjects who are at risk of developing a lysosomal storage disease, such as Gaucher Type 3 or Niemann-Pick Type C, due to, for example, a mutation in the subject or the subject's family lineage known to cause such disease. Therefore, in some embodiments of the methods described herein, the subject has been diagnosed as being at risk of developing said disease or disorder, and the method prevents or delays the onset and/or development of the cognitive and/or ataxic symptoms of the disease or disorder in the subject. In some embodiments, the subject has been diagnosed as being at risk of developing said disease or disorder by virtue of having a mutation in a gene as described herein.

In a third aspect, the present invention provides a method (Method 3) for increasing brain tissue volume, or preventing or delaying loss of brain tissue volume, in a subject, such as in a subject in need thereof, said method comprising administering to the subject an effective amount of a quinuclidine compound as described herein, e.g., a compound according to Formula (I) or any of (II)-(XII), (Ia)-(XIIa), or (Ib)-(XIIb), or any of Compounds 1 or 1.1 to 1.75. Also provided is a quinuclidine compound as described herein, e.g., a compound according to Formula (I) or any of (II)-(XII), (Ia)-(XIIa), or (Ib)-(XIIb), or any of Compounds 1 or 1.1 to 1.75, for use in increasing brain tissue volume, or preventing or delaying loss of brain tissue volume, in a subject in need thereof, e.g., for use in Method 3 or any of 3.1-3.65. Further provided is the use of a quinuclidine compound as described herein, e.g., a compound according to Formula (I) or any of (II)-(XII), (Ia)-(XIIa), or (Ib)-(XIIb), or any of Compounds 1 or 1.1 to 1.75, in the manufacture of a medicament for increasing brain tissue volume, or preventing or delaying loss of brain tissue volume, in a subject in need thereof, e.g., in the manufacture of a medicament for use in Method 3 or any of 3.1-3.65.

In particular further embodiments of Method 3, the present disclosure provides:

3.1. Method 3, wherein the method comprises administering to the subject an effective amount of a compound according to Formula (I) or any of (II)-(XII), (Ia)-(XIIa), or (Ib)-(XIIb), or any of Compounds 1 or any of 1.1 to 1.75;

3.2. Method 3, wherein the method comprises administering to the subject an effective amount of Compound 1 or any one or more of Compounds 1.1 to 1.75;

3.3. Method 3 or any of 3.1-3.2, wherein the method comprises administering to the subject an effective amount of a pharmaceutical composition comprising the compound according to Formula (I) or any of (II)-(XII), (Ia)-(XIIa), or (Ib)-(XIIb), or any of Compounds 1 or any of 1.1 to 1.75;

3.4. Method 3 or any of 3.1-3.3, wherein the method comprises administering to the subject an effective amount of a pharmaceutical composition comprising the Compound 1 or any one or more of Compounds 1.1 to 1.75;

3.5. Method 3.3 or 3.4, wherein the pharmaceutical composition further comprises at least one pharmaceutically acceptable excipient, as described herein;

3.6. Method 3 or any of 3.1-3.5, wherein the method comprises administering a pharmaceutical dosage form comprising an effective amount of the compound or an effective amount of the pharmaceutical composition;

3.7. Method 3.6, wherein the dosage form is an oral dosage form (e.g., a pill, capsule, caplet, tablet, dragee, powder, granule, film, lozenge, or liquid);

3.8. Method 3.7, wherein the dosage form is a chewable tablet;

3.9. Method 3.6, wherein the dosage form is a parenteral dosage form (e.g., wherein the pharmaceutical composition is formulated for injection);

3.10. Method 3.9, wherein the injection is intravenous, intramuscular, intrathecal, or subcutaneous injection, optionally a sterile injection;

3.11. Method 3.6, wherein the dosage form is a topical or rectal dosage form;

3.12. Method 3.6, wherein the dosage form is an intranasal dosage form (e.g., an aerosol);

3.13. Method 3 or any of 3.1 to 3.12, wherein the method further comprises concurrently administering a second active agent, e.g., a second compound capable of reducing levels of glycosylceramide in a patient in need thereof, as described herein;

3.14. Method 3.13, wherein the second active agent is administrated in the same pharmaceutical composition or dosage form as the quinuclidine compound;

3.15. Method 3.13 or 3.14, wherein the second active agent is a GCS inhibitor (e.g., miglustat, or eliglustat);

3.16. Method 3, or any of 3.1-3.15, wherein the subject is a mammalian animal;

3.17. Method 3.16, wherein the subject is a primate animal;

3.18. Method 3.17, wherein the subject is a human;

3.19. Method 3 or any of 3.1-3.18, wherein the subject has ataxia, for example, symptoms selected from gait instability, asthenia, asynergy, delayed reaction time, dyschronometria, dysarthria, dysphagia, hypotonia, dysmetria, hypometria, hypermetria, dysdiadochokinesia, speech slurring, voice tremor, ataxic respiration, postural instability, and combinations thereof, for example, wherein the primary ataxic deficit is a gait instability;

3.20. Method 3.19, wherein the subject has a baseline ataxia of at least 0.5 on the Scale for Assessment and Rating of Ataxia (SARA) scale at the initiation of therapy according to the method, e.g., a baseline SARA score of at least 1, or at least 2, or at least 3, or at least 4, or at least 5, or at least 10, or at least 20;

3.21. Method 3 or any of 3.1-3.20, wherein the subject has cognitive dysfunction (e.g., dementia);

3.22. Method 3.21, wherein the cognitive dysfunction is a dementia;

3.23. Method 3.22, wherein the dementia shows signs of defects in visual search speed, scanning speed of processing, mental flexibility, and/or executive functioning, e.g., as evidence by a TMT-A of greater than 30 seconds, or greater than 45 seconds, or greater than 60 seconds, and/or a TMT-B of greater than 70 seconds, or greater than 90 seconds, or greater than 120 seconds, or greater than 150 seconds, or greater than 180 seconds, and/or wherein TMT-B minus TMT-A is greater than 40 seconds, or greater than 60 seconds, or greater than 90 seconds, or greater than 120 seconds;

3.24. Method 3, or any of 3.1-3.23, wherein the subject has Gaucher disease Type 3;

3.25. Method 3, or any of 3.1-3.24, wherein the subject has Niemann-Pick disease Type C;

3.26. Method 3, or any of 3.1-3.24, wherein the subject has a GM2-gangliosidosis (e.g., Tay-Sachs disease, Sandhoff disease, or GM2 gangliosidosis AB variant);

3.27. Method 3, or any of 3.1-3.24, wherein the subject is diagnosed with a mutation in the gene GBA1;

3.28. Method 3, or any of 3.1-3.24, wherein the subject is diagnosed with a mutation in the genes NPC1 and/or NPC2;

3.29. Method 3, or any of 3.1-3.24, wherein the subject is diagnosed with a mutation in the gene HEXA (encoding hexosaminidase A) and/or a mutation in the gene HEXB (encoding hexosaminidase B) and/or a mutation in the gene GM2A (encoding the GM2 ganglioside activator protein);

3.30. Method 3, or any of 3.1-3.29, wherein the subject is diagnosed with Alzheimer's disease or Parkinson's disease;

3.31. Method 3, or any of 3.1-3.30, wherein the subject undergoes concurrent treatment with enzyme replacement therapy (ERT), e.g., using a glucocerebrosidase (e.g., imiglucerase, velaglucerase, or taliglucerase), optionally wherein each of such enzyme is a recombinant enzyme;

3.32. Method 3.31, wherein the subject undergoes concurrent treatment with one or more of imiglucerase, velaglucerase (e.g., velaglucerase alfa), and taliglucerase (e.g., taliglucerase alfa);

3.33. Method 3.32, wherein the subject undergoes concurrent treatment with imiglucerase;

3.34. Method 3.33, wherein the subject undergoes concurrent treatment with imiglucerase at a dosage of from 2.5 units/kg body weight to 80 units/kg body weight every 1 to 3 weeks, e.g., 40 to 60 units/kg body weight every 2 weeks (1 unit of imiglucerase is the amount of enzyme that catalyzes the hydrolysis of 1 micromole of the synthetic substrate p-nitrophenyl-β-D-glucopyranoside per minute at 37° C.);

3.35. Method 3.34, wherein the subject's dosage of imiglucerase at each administration (e.g., every 1 to 3 weeks, e.g., every 2 weeks) is administered as an intravenous (IV) infusion over a period of 1-3 hours (e.g., 1-2 hours);

3.36. Method 3 or any of 3.1-3.35, wherein the subject has been administered enzyme replacement therapy (e.g., imiglucerase, velaglucerase, and/or taliglucerase) prior to the initiation of treatment with the compound according to Formula (I) (or any of (II)-(XII), (Ia)-(XIIa), or (Ib)-(XIIb), or any of Compounds 1 or 1.1 to 1.75);

3.37. Method 3.36, wherein the subject has been administered imiglucerase therapy for at least 6 months prior to beginning therapy with the compound according to Formula (I) (or any of (II)-(XII), (Ia)-(XIIa), or (Ib)-(XIIb), or any of Compounds 1 or 1.1 to 1.75), for example, at least 12 months (1 year), or at least 18 months, or at least 2 years, or at least 3 years.

3.38. Method 3.36 or 3.37, wherein the subject has been administered imiglucerase therapy for at least 6 months at a stable dose prior to beginning therapy with the compound according to Formula (I) (or any of (II)-(XII), (Ia)-(XIIa), or (Ib)-(XIIb), or any of Compounds 1 or 1.1 to 1.75);

3.39. Method 3 or any of 3.1-3.38, wherein the method further comprises the step of transitioning the subject from ERT therapy (e.g., imiglucerase, velaglucerase, or taliglucerase) to treatment with the compound according to Formula (I) (or any of (II)-(XII), (Ia)-(XIIa), or (Ib)-(XIIb), or any of Compounds 1 or 1.1 to 1.75);

3.40. Method 3 or any of 3.1-3.39, wherein the subject has a hemoglobin level of at least 11 g/dL for females and at least 12 g/dL for males;

3.41. Method 3, or any of 3.1-3.40, wherein the subject has a platelet count of at least 100,000/cubic millimeter;

3.42. Method 3, or any of 3.1-3.41, wherein the subject has a splenic volume of less than 10 multiples of normal (MN) and/or a hepatic volume of less than 1.5 MN;

3.43. Method 3, or any of 3.1-3.42, wherein the subject is diagnosed with a concurrent dementia, e.g., Alzheimer's disease or Parkinson's disease;

3.44. Method 3, or any of 3.1-3.43, wherein the subject is at least 18 years of age (e.g., 18-30 years of age) at the start of treatment with the compound according to Formula (I) (or any of (II)-(XII), (Ia)-(XIIa), or (Ib)-(XIIb), or any of Compounds 1 or 1.1 to 1.75);

3.45. Method 3, or any of 3.1-3.44, wherein the subject has a glucosylceramide (GL1) concentration of 4.4-11.1 ng/mL in cerebrospinal fluid (CSF) and 4.9-8.3 g/mL in plasma;

3.46. Method 3, or any of 3.1-3.45, wherein the subject has a glucosylsphingosine (lyso-GL1) concentration of 20.1-67.6 pg/mL in CSF and 8.8-159.0 ng/mL in plasma;

3.47. Method 3, or any of 3.1-3.46, wherein the subject is administered a daily dose of about 1 mg to about 150 mg of the compound according to Formula (I) (or any of (II)-(XII), (Ia)-(XIIa), or (Ib)-(XIIb), or any of Compounds 1 or 1.1 to 1.75), e.g., from 5 to 50 mg, or from 10 to 40 mg, or from 10 to 30 mg, or from 10 to 20 mg, or from 20 to 30 mg, or from 30 to 40 mg, or from 40 to 50 mg, or from 5 to 25 mg, or from 20 to 50 mg, or from 5 to 15 mg, or from 15 to 30 mg, or about 15 mg, or selected from 2, 5, 15, 25, 50, 100, or 150 mg;

3.48. Method 3, or any of 3.1-3.47, wherein the subject is a human adult patient, e.g., of an age from 18 to 80 years old, e.g., from 18 to 60 years old, or from 18 to years old, or from 18 to 30 years old, or from 18 to 25 years old;

3.49. Method 3, or any of 3.1-3.47, wherein the subject is a human pediatric patient, e.g., of an age from 0 to 18 years old, e.g., from 1 to 15 years old, or from 1 to 5 years old, or from 5 to 10 years old, or from 10 to 15 years old, or from 10 to 18 years old;

3.50. Method 3, or any of 3.1-3.49, wherein the method results in an increase in brain tissue volume, or prevention or delay in loss of brain tissue volume, in one or more brain regions selected from: right accumbens, left putamen, left entorhinal cortex, right putamen, right postcentral lobe, left pericalcarine, right amygdala, left cuneus, and left lingual, e.g., as measured using volumetric magnetic resonance imaging (vMRI).

3.51. Method 3, or any of 3.1-3.50, wherein the method results in an increased brain tissue volume in one or more brain regions associated with executive function.

3.52. Method 3.50 or 3.51, wherein the increase in brain tissue volume in the one or more brain regions is accompanied by an enhancement in neuronal connectivity within the one or more brain regions, e.g., as shown using functional magnetic resonance imaging (fMRI).

3.53. Method 3, or any of 3.1-3.52, wherein the method results in an increase in the whole brain tissue volume.

3.54. Method 3, or any one of 3.1-3.53, wherein the increase in brain tissue volume is at least 5 mm$^3$, in any one or more brain regions, e.g., at least 10 mm$^3$, at least 15 mm$^3$, at least 20 mm$^3$, at least 30 mm$^3$, at least 50 mm$^3$, at least 70 mm$^3$, or at least 90 mm$^3$, in any one or more brain regions, and/or up to 100 mm$^3$, or up to 150 mm$^3$, in any one or more brain regions.

3.55. Method 3, or any of 3.1-3.54, wherein the increase in whole brain tissue volume is at least 5 mm$^3$, e.g., at least 30 mm$^3$, at least 60 mm$^3$, at least 90 mm$^3$, at least 120 mm³, at least 150 mm³, at least 200 mm³, or at least 250 mm³, and/or up to 400 mm³, or up to 500 mm³, whole brain volume.

3.56. Method 3, or any of 3.1-3.55, wherein the increase in brain tissue volume is at least 0.1%, e.g., from 0.1% to 10.0%, compared to initial brain tissue volume, in any one or more brain regions, e.g., at least 0.50%, 0.75%, 1.0%, 2.0% or 5.0%, in any one or more brain regions.

3.57. Method 3, or any of 3.1-3.56, wherein the increase in whole brain tissue volume is at least 0.05%, e.g., from 0.05% to 0.30%, compared to initial whole brain tissue volume, e.g., at least 0.10%, 0.15%, 0.20% or 0.25%.

3.58. Method 3, or any of 3.1-3.57, wherein the compound according to Formula (I) (or any of (II)-(XII), (Ia)-(XIIa), or (Ib)-(XIIb), or any of Compounds 1 or 1.1 to 1.75), or pharmaceutically acceptable salt or prodrug thereof, is administered by systemic administration, e.g., via a parenteral route or a non-parenteral route;

3.59. Method 3.58, wherein the route of administration is oral (enteral);

3.60. Method 3.58, wherein the route of administration is parenteral, e.g., by injection, such as by intravenous injection;

3.61. Method 3, or any of 3.1-3.57, wherein the compound according to Formula (I) (or any of (II)-(XII), (Ia)-(XIIa), or (Ib)-(XIIb), or any of Compounds 1 or 1.1 to 1.75), or pharmaceutically acceptable salt or prodrug thereof, is administered by local administration, e.g., by topical administration;

3.62. Method 3, or any of 3.1-3.61, wherein the compound is (S)-quinuclidin-3-yl (2-(2-(4-fluorophenyl)thiazol-4-yl)propan-2-yl)carbamate or quinuclidin-3-yl (2-(4'-fluoro-[1,1'-biphenyl]-3-yl)propan-2-yl)carbamate;

3.63. Method 3.62, wherein the dosage of the compound is 15 mg/day orally administered;

3.64. Method 3.63, wherein the dosage of the compound is 15 mg/day in a single oral dose;

3.65. Method 3, or any of 3.1-3.61, wherein the subject is administered a single daily dose of 5 mg, 10 mg, 15 mg, or 20 mg of the compound, e.g., of (S)-quinuclidin-3-yl (2-(2-(4-fluorophenyl)thiazol-4-yl)propan-2-yl)carbamate, optionally in malate salt acid addition salt form.

The methods according to Method 3 et seq. may be beneficial for subjects who have been diagnosed with a lysosomal storage disease, such as Gaucher Type 3 or Niemann-Pick Type C, but who are not yet experiencing the cognitive and/or ataxic symptoms associated with the disease state. The methods according to Method 3 et seq. may also be beneficial for subjects who are at risk of developing a lysosomal storage disease, such as Gaucher Type 3 or Niemann-Pick Type C, due to, for example, a mutation in the subject or the subject's family lineage known to cause such disease. Therefore, in some embodiments of the methods described herein, the subject has been diagnosed as being at risk of developing said disease or disorder, and the method prevents or delays the onset and/or development of the cognitive and/or ataxic symptoms of the disease or disorder in the subject. In some embodiments, the subject has been diagnosed as being at risk of developing said disease or disorder by virtue of having a mutation in a gene as described herein.

The methods according to Method 3 et seq. are directed to increasing brain tissue volume, and there is no particular limitation on the possible regions of the brain that may be beneficially increased in terms of tissue volume. Relevant regions of the brain may, for instance, include right putamen, right postcentral lobe, right amygdala, right lingual, left cuneus, left lingual, right superior temporal lobe, right lateral orbitofrontal lobe, left pericalcarine lobe, left transverse temporal lobe, right temporal pole, right accumbens, left putamen, left entorhinal cortex, right pallidum, left accumbens, left temporal pole, right entorhinal cortex, left caudate, right frontal pole, right pars opercularis lobe, right transverse temporal lobe, right hippocampus, left paracentral lobe, left superior parietal lobe, left fusiform lobe, left banksSTS, right paracentral lobe, right medial temporal lobe, left caudal middle frontal lobe, right rostral anterior cingulate lobe, left pars triangularis lobe, left precentral lobe, right pars orbitalis lobe, left middle temporal lobe, left isthmus cingulate lobe, right caudal middle frontal lobe, right whole temporal lobe, left inferior temporal lobe, right lateral partial lobe, right lateral occipital lobe, left supramarginal lobe, left whole temporal lobe, right rostral middle frontal lobe, left rostral middle frontal lobe, left medial temporal lobe, and left superior frontal lobe, or any combinations thereof. Particular regions of the brain which may in at least some embodiments exhibit the greatest relative volume gain as a result of the methods according to Method 3 et seq. include: right accumbens, left putamen, left entorhinal cortex, right putamen, right postcentral lobe, left pericalcarine, right amygdala, left cuneus, and left lingual.

Monitoring and Assessment Methods

In a fourth aspect, the present invention provides a method (Method 4) for monitoring the progression or regression of a neurological disorder associated with a lysosome storage disease in a subject, wherein the subject is undergoing a treatment which comprises administering to the subject an effective amount of a quinuclidine compound as described herein, e.g., a compound according to Formula (I) or any of (II)-(XII), (Ia)-(XIIa), or (Ib)-(XIIb), or any of Compounds 1 or 1.1 to 1.75; said method comprising measuring brain tissue volume of the subject over a time period during the course of the treatment, e.g. using volumetric magnetic resonance imaging (vMRI), and assessing the extent of any change in brain tissue volume over said time period, and optionally further comprising commencing or adjusting treatment of the subject by administering to the subject an effective amount of a quinuclidine compound as described herein, e.g., a compound according to Formula (I) or any of (II)-(XII), (Ia)-(XIIa), or (Ib)-(XIIb), or any of Compounds 1 or 1.1 to 1.75. As will be appreciated, in order to assess the extent of any change in brain tissue volume as a result of the treatment, measurement of brain tissue volume may, for example, be conducted on commencement of the above treatment, or shortly after commencing treatment (e.g. 1 to 14 days), and either at the end of a designated treatment time period or intermittently/routinely (e.g. weekly, monthly, every 2, 3, 4, 6, 9, 12 months, etc.) over the course of an ongoing treatment so as to assess, and reassess, the extent of any change in brain volume over the course of the treatment. Accumulating comparative results relating to the subject's condition over a time period over which the subject has been undergoing treatment allows for increased accuracy in determining the subject's condition and the progression/regression of disease symptoms.

In particular further embodiments of Method 4, the present disclosure provides:

4.1. Method 4, wherein the treatment comprises administering to the subject an effective amount of a compound according to Formula (I) or any of (II)-(XII), (Ia)-(XIIa), or (Ib)-(XIIb), or any of Compounds 1 or any of 1.1 to 1.75;

4.2. Method 4, wherein the treatment comprises administering to the subject an effective amount of Compound 1 or any one or more of Compounds 1.1 to 1.75;

4.3. Method 4 or any of 4.1-4.2, wherein the treatment comprises administering to the subject an effective amount of a pharmaceutical composition comprising the compound according to Formula (I) or any of (II)-(XII), (Ia)-(XIIa), or (Ib)-(XIIb), or any of Compounds 1 or any of 1.1 to 1.75;

4.4. Method 4 or any of 4.1-4.2, wherein the treatment comprises administering to the subject an effective amount of a pharmaceutical composition comprising the Compound 1 or any one or more of Compounds 1.1 to 1.75;

4.5. Method 4.3 or 4.4, wherein the pharmaceutical composition further comprises at least one pharmaceutically acceptable excipient, as described herein;

4.6. Method 4 or any of 4.1-4.5, wherein the treatment comprising administering a pharmaceutical dosage form comprising an effective amount of the compound or an effective amount of the pharmaceutical composition;

4.7. Method 4.6, wherein the dosage form is an oral dosage form (e.g., a pill, capsule, caplet, tablet, dragee, powder, granule, film, lozenge, or liquid);

4.8. Method 4.7, wherein the dosage form is a chewable tablet;

4.9. Method 4.6, wherein the dosage form is a parenteral dosage form (e.g., wherein the pharmaceutical composition is formulated for injection);

4.10. Method 4.9, wherein the injection is intravenous, intramuscular, intrathecal, or subcutaneous injection, optionally a sterile injection;

4.11. Method 4.6, wherein the dosage form is a topical or rectal dosage form;

4.12. Method 4.6, wherein the dosage form is an intranasal dosage form (e.g., an aerosol);

4.13. Method 4 or any of 4.1 to 4.12, wherein the treatment further comprises concurrently administering a second active agent, e.g., a second compound capable of reducing levels of glycosylceramide in a patient in need thereof, as described herein;

4.14. Method 4.13, wherein the second active agent is administrated in the same pharmaceutical composition or dosage form as the quinuclidine compound;

4.15. Method 4.13 or 4.14, wherein the second active agent is a GCS inhibitor (e.g., miglustat or eliglustat);

4.16. Method 4, or any of 4.1-4.15, wherein the subject is a mammalian animal;

4.17. Method 4.16, wherein the subject is a primate animal;

4.18. Method 4.17, wherein the subject is a human;

4.19. Method 4 or any of 4.1-4.18, wherein the subject has ataxia, for example, symptoms selected from gait instability, asthenia, asynergy, delayed reaction time, dyschronometria, dysarthria, dysphagia, hypotonia, dysmetria, hypometria, hypermetria, dysdiadochokinesia, speech slurring, voice tremor, ataxic respiration, postural instability, and combinations thereof, for example, wherein the primary ataxic deficit is a gait instability;

4.20. Method 4.19, wherein the subject has a baseline ataxia of at least 0.5 on the Scale for Assessment and Rating of Ataxia (SARA) scale at the initiation of therapy according to the method, e.g., a baseline SARA score of at least 1, or at least 2, or at least 3, or at least 4, or at least 5, or at least 10, or at least 20;

4.21. Method 4 or any of 4.1-4.20, wherein the subject has cognitive dysfunction (e.g., dementia);

4.22. Method 4.21, wherein the cognitive dysfunction is a dementia;

4.23. Method 4.22, wherein the dementia shows signs of defects in visual search speed, scanning speed of processing, mental flexibility, and/or executive functioning, e.g., as evidence by a TMT-A of greater than 30 seconds, or greater than 45 seconds, or greater than 60 seconds, and/or a TMT-B of greater than 70 seconds, or greater than 90 seconds, or greater than 120 seconds, or greater than 150 seconds, or greater than 180 seconds, and/or wherein TMT-B minus TMT-A is greater than 40 seconds, or greater than 60 seconds, or greater than 90 seconds, or greater than 120 seconds;

4.24. Method 4, or any of 4.1-4.23, wherein the subject has Gaucher disease Type 3;

4.25. Method 4, or any of 4.1-4.24, wherein the subject has Niemann-Pick disease Type C;

4.26. Method 4, or any of 4.1-4.24, wherein the subject has a GM2-gangliosidosis (e.g., Tay-Sachs disease, Sandhoff disease, or GM2 gangliosidosis AB variant);

4.27. Method 5, or any of 4.1-4.24, wherein the subject is diagnosed with a mutation in the gene GBA1;

4.28. Method 5, or any of 4.1-4.24, wherein the subject is diagnosed with a mutation in the genes NPC1 and/or NPC2;

4.29. Method 5, or any of 4.1-4.24, wherein the subject is diagnosed with a mutation in the gene HEXA (encoding hexosaminidase A) and/or a mutation in the gene HEXB (encoding hexosaminidase B) and/or a mutation in the gene GM2A (encoding the GM2 ganglioside activator protein);

4.30. Method 4, or any of 4.1-4.29, wherein the subject is diagnosed with Alzheimer's disease or Parkinson's disease;

4.31. Method 4, or any of 4.1-4.30, wherein the subject undergoes concurrent treatment with enzyme replacement therapy (ERT), e.g., using a glucocerebrosidase (e.g., imiglucerase, velaglucerase, or taliglucerase), optionally wherein each of such enzyme is a recombinant enzyme;

4.32. Method 4.31, wherein the subject undergoes concurrent treatment with one or more of imiglucerase, velaglucerase (e.g., velaglucerase alfa), and taliglucerase (e.g., taliglucerase alfa);

4.33. Method 4.32, wherein the subject undergoes concurrent treatment with imiglucerase;

4.34. Method 4.33, wherein the subject undergoes concurrent treatment with imiglucerase at a dosage of from 2.5 units/kg body weight to 80 units/kg body weight every 1 to 3 weeks, e.g., 40 to 60 units/kg body weight every 2 weeks (1 unit of imiglucerase is the amount of enzyme that catalyzes the hydrolysis of 1 micromole of the synthetic substrate p-nitrophenyl-β-D-glucopyranoside per minute at 37° C.);

4.35. Method 4.34, wherein the subject's dosage of imiglucerase at each administration (e.g., every 1 to 3 weeks, e.g., every 2 weeks) is administered as an intravenous (IV) infusion over a period of 1-3 hours (e.g., 1-2 hours);

4.36. Method 4 or any of 4.1-4.35, wherein the subject has been administered enzyme replacement therapy (e.g., imiglucerase, velaglucerase, and/or taliglucerase) prior to the initiation of treatment with the compound according to Formula (I) (or any of (II)-(XII), (Ia)-(XIIa), or (Ib)-(XIIb), or any of Compounds 1 or 1.1 to 1.75);

4.37. Method 4.36, wherein the subject has been administered imiglucerase therapy for at least 6 months prior to beginning therapy with the compound according to Formula (I) (or any of (II)-(XII), (Ia)-(XIIa), or (Ib)-(XIIb), or any of Compounds 1 or 1.1 to 1.75), for example, at least 12 months (1 year), or at least 18 months, or at least 2 years, or at least 3 years;

4.38. Method 4.36 or 4.37, wherein the subject has been administered imiglucerase therapy for at least 6 months at a stable dose prior to beginning therapy with the compound according to Formula (I) (or any of (II)-(XII), (Ia)-(XIIa), or (Ib)-(XIIb), or any of Compounds 1 or 1.1 to 1.75);

4.39. Method 4 or any of 4.1-4.38, wherein the method further comprises the step of transitioning the subject from ERT therapy (e.g., imiglucerase, velaglucerase, or taliglucerase) to treatment with the compound according to Formula (I) (or any of (II)-(XII), (Ia)-(XIIa), or (Ib)-(XIIb), or any of Compounds 1 or 1.1 to 1.75);

4.40. Method 4 or any of 4.1-4.39, wherein the subject has a hemoglobin level of at least 11 g/dL for females and at least 12 g/dL for males;

4.41. Method 4, or any of 4.1-4.40, wherein the subject has a platelet count of at least 100,000/cubic millimeter;

4.42. Method 4, or any of 4.1-4.41, wherein the subject has a splenic volume of less than 10 multiples of normal (MN) and/or a hepatic volume of less than 1.5 MN;

4.43. Method 4, or any of 4.1-4.42, wherein the subject is diagnosed with a concurrent dementia, e.g., Alzheimer's disease or Parkinson's disease;

4.44. Method 4, or any of 4.1-4.43, wherein the subject is at least 18 years of age (e.g., 18-30 years of age) at the start of treatment with the compound according to Formula (I) (or any of (II)-(XII), (Ia)-(XIIa), or (Ib)-(XIIb), or any of Compounds 1 or 1.1 to 1.75);

4.45. Method 4, or any of 4.1-4.44, wherein the subject has a glucosylceramide (GL1) concentration of 4.4-11.1 ng/mL in cerebrospinal fluid (CSF) and 4.9-8.3 pg/mL in plasma;

4.46. Method 4, or any of 4.1-4.45, wherein the subject has a glucosylsphingosine (lyso-GL1) concentration of 20.1-67.6 pg/mL in CSF and 8.8-159.0 ng/mL in plasma;

4.47. Method 4, or any of 4.1-4.46, wherein the subject is administered a daily dose of about 1 mg to about 150 mg of the compound according to Formula (I) (or any of (II)-(XII), (Ia)-(XIIa), or (Ib)-(XIIb), or any of Compounds 1 or 1.1 to 1.75), e.g., from 5 to 50 mg, or from 10 to 40 mg, or from 10 to 30 mg, or from 10 to 20 mg, or from 20 to 30 mg, or from 30 to 40 mg, or from 40 to 50 mg, or from 5 to 25 mg, or from 20 to 50 mg, or from 5 to 15 mg, or from 15 to 30 mg, or about 15 mg, or selected from 2, 5, 15, 25, 50, 100, or 150 mg;

4.48. Method 4, or any of 4.1-4.47, wherein the subject is a human adult patient, e.g., of an age from 18 to 80 years old, e.g., from 18 to 60 years old, or from 18 to years old, or from 18 to 30 years old, or from 18 to 25 years old;

4.49. Method 4, or any of 4.1-4.47, wherein the subject is a human pediatric patient, e.g., of an age from 0 to 18 years old, e.g., from 1 to 15 years old, or from 1 to 5 years old, or from 5 to 10 years old, or from 10 to 15 years old, or from 10 to 18 years old;

4.50. Method 4, or any of 4.1-4.49, wherein said time period over which the subject undergoes the course of treatment and over which brain volume is monitored is from 3 months to 24 months, e.g., 3 months to 12 months, 3 months to 6 months, 6 months to 24 months, 6 months to 18 months, 6 months to 12 months, 12 months to 24 months, or 12 to 18 months;

4.51. Method 4, or any of 4.1-4.50, wherein measuring brain tissue volume of the subject over said time period is by brain positron emission tomography (PET) or by volumetric magnetic resonance imaging (vMRI);

4.52. Method 4.51, wherein brain tissue volume of the subject is measured a plurality of times, intermittently or routinely, over the course of the treatment, e.g., weekly, monthly, every 2, 3, 4, 6, 9, 12 months, etc.;

4.53. Method 4, or any of 4.1-4.52, wherein, if there is a decrease or absence of an increase in whole brain volume observed over said time period, the method further comprises modifying the treatment by increasing the dosage of the compound of Formula (I) (or any of (II)-(XII), (Ia)-(XIIa), or (Ib)-(XIIb), or any of Compounds 1 or 1.1 to 1.75), administered to the subject during the treatment and reassessing the extent of any change in brain tissue volume after a further time period over the course of the modified treatment with the increased dosage;

4.54. Method 4, or any of 4.1-4.53, wherein, if there is a decrease or absence of an increase in volumes in three or more of the following brain regions: right accumbens area, left putamen, left entorhinal cortex, right putamen, right postcentral lobe, left pericalcarine, right amygdala, left cuneus, and left lingual, observed over said time period, the method further comprises modifying the treatment by increasing the dosage of the compound of Formula (I) (or any of (II)-(XII), (Ia)-(XIIa), or (Ib)-(XIIb), or any of Compounds 1 or 1.1 to 1.75), administered to the subject during the treatment, administered to the subject and reassessing the extent of any change in brain tissue volume after a further time period over the course of the modified treatment with the increased dosage;

4.55. Method 4, or any one of 4.1-4.54, wherein the treatment results in an increase in brain tissue volume, or prevention or delay in loss of brain tissue volume, over the time period in one or more brain regions selected from: right accumbens, left putamen, left entorhinal cortex, right putamen, right postcentral lobe, left pericalcarine, right amygdala, left cuneus, and left lingual;

4.56. Method 4, or any of 4.1-4.55, wherein the treatment results in an increased brain volume in one or more brain regions associated with executive function;

4.57. Method 4.55 or 4.56, wherein the increase in brain volume in the one or more brain regions is accompanied by an enhancement in neuronal connectivity within the one or more brain regions, e.g., as shown using functional magnetic resonance imaging (fMRI);

4.58. Method 4, or any of 4.1-4.57, wherein the treatment results in an increase in the whole brain tissue volume;

4.59. Method 4, or any one of 4.55-4.58, wherein the increase in brain tissue volume is at least 5 mm$^3$, in any one or more brain regions, e.g., at least 10 mm$^3$, at least 15 mm$^3$, at least 20 mm$^3$, at least 30 mm$^3$, at least 50 mm$^3$, at least 70 mm$^3$, or at least 90 mm$^3$, in any one or more brain regions, and/or up to 100 mm$^3$, or up to 150 mm$^3$, in any one or more brain regions.

4.60. Method 4, or any of 4.55-4.59, wherein the increase in whole brain tissue volume is at least 5 mm$^3$, e.g., at least 30 mm$^3$, at least 60 mm$^3$, at least 90 mm$^3$, at least 120 mm$^3$, at least 150 mm$^3$, at least 200 mm$^3$, or at least 250 mm$^3$, and/or up to 400 mm$^3$, or up to 500 mm$^3$, whole brain volume.

4.61. Method 4, or any of 4.55-4.60, wherein the increase in brain tissue volume is at least 0.1%, e.g., from 0.1% to 10.0%, compared to initial brain tissue volume, in any one or more brain regions, e.g., at least 0.50%, 0.75%, 1.0%, 2.0% or 5.0%, in any one or more brain regions.

4.62. Method 4, or any of 4.55-4.61, wherein the increase in whole brain tissue volume is at least 0.05%, e.g., from 0.05% to 0.30%, compared to initial whole brain tissue volume, e.g., at least 0.10%, 0.15%, 0.20% or 0.25%.

4.63. Method 4, or any of 4.1-4.62, wherein the compound according to Formula (I) (or any of (II)-(XII), (Ia)-(XIIa), or (Ib)-(XIIb), or any of Compounds 1 or 1.1 to 1.75), or pharmaceutically acceptable salt or prodrug thereof, is administered by systemic administration, e.g., via a parenteral route or a non-parenteral route;

4.64. Method 4.63, wherein the route of administration is oral (enteral);

4.65. Method 4.63, wherein the route of administration is parenteral, e.g., by injection, such as by intravenous injection;

4.66. Method 4, or any of 4.1-4.63, wherein the compound according to Formula (I) (or any of (II)-(XII), (Ia)-(XIIa), or (Ib)-(XIIb), or any of Compounds 1 or 1.1 to 1.75), or pharmaceutically acceptable salt or prodrug thereof, is administered by local administration, e.g., by topical administration;

4.67. Method 4, or any of 4.1-4.67, wherein the compound is (S)-quinuclidin-3-yl (2-(2-(4-fluorophenyl)thiazol-4-yl)propan-2-yl)carbamate or quinuclidin-3-yl (2-(4'-fluoro-[1,1'-biphenyl]-3-yl)propan-2-yl)carbamate;

4.68. Method 4.63, wherein the dosage of the compound is 15 mg/day orally administered;

4.69. Method 4.63, wherein the dosage of the compound is 15 mg/day in a single oral dose;

4.70. Method 4, or any of 4.1-4.67, wherein the subject is administered a single daily dose of 5 mg, 10 mg, 15 mg, or 20 mg of the compound, e.g., of (S)-quinuclidin-3-yl (2-(2-(4-fluorophenyl)thiazol-4-yl)propan-2-yl)carbamate, optionally in malate salt acid addition salt form.

The methods according to Method 4 et seq. may in particular embodiments be carried out using volumetric magnetic resonance imaging (vMRI) as described herein. Analytical tools may also be employed for assisting the assessment of vMRI data, including, for example, Tensor-Based Morphometry (TBM), as described herein.

It will be appreciated that in some embodiments, the Methods 4 et seq., may alternatively be viewed as methods of treating or preventing a neurological disorder associated with a lysosome storage disease, in a subject (e.g., patient) in need thereof, the method comprising monitoring the progression or regression of the neurological disorder associated with a lysosome storage disease, wherein the subject is undergoing a treatment which comprises administering to the subject an effective amount of a quinuclidine compound as described herein, e.g., a compound according to Formula (I) or any of (II)-(XII), (Ia)-(XIIa), or (Ib)-(XIIb), or any of Compounds 1 or 1.1 to 1.75, and wherein said method comprises the steps of measuring brain tissue volume of the subject over a time period during the course of the treatment, e.g. using vMRI, assessing the extent of any change in brain tissue volume over said time period, and adjusting the parameters of the treatment method accordingly.

In a fifth aspect, the present invention provides a method (Method 5) for assessing the onset of a neurological disorder associated with a lysosome storage disease in a subject at risk of developing said neurological disorder, said method comprising: a) measuring the brain tissue volume of the subject (e.g. using vMRI) and comparing against a reference standard to assess whether brain tissue volume is lower than the reference standard; and b) where the brain tissue volume identified in step (a) is lower than the reference standard, identifying the onset of said neurological disorder; the method optionally further comprising: c) commencing treatment of the subject by administering to the subject an effective amount of a quinuclidine compound as described herein, e.g., a compound according to Formula (I) or any of (II)-(XII), (Ia)-(XIIa), or (Ib)-(XIIb), or any of Compounds 1 or 1.1 to 1.75. As will be appreciated, by measuring a subject's brain tissue volume and comparing with a reference standard, it is possible to determine whether the subject having a lysosome storage disease, and at risk of developing a neurological disorder associated therewith, has reached a stage of disease progression at which treatment, for instance with a compound of Formula (I), may be particularly beneficial.

A reference standard brain tissue volume (whole brain tissue volume and/or individual brain tissue regional volumes) may be determined based on healthy (dementia-free) population data (acquired or available from published sources) thereby allowing for age- and gender-specific normative volumetric data to be used as the reference standard based on the age and gender of the subject. This allows a meaningful comparison upon which to assess the subject's disease progression based on the extent to which the subject's brain tissue volume is lower than the reference standard in regions of the brain tissue and/or based on whole brain tissue volume, from which an onset of a neurological disorder associated with the subject's lysosome storage disease may be determined.

In particular further embodiments of Method 5, the present disclosure provides:

5.1. Method 5, wherein the subject has Gaucher disease Type 3;

5.2. Method 5, wherein the subject has Niemann-Pick disease Type C;

5.3. Method 5, wherein the subject has a GM2-gangliosidosis (e.g., Tay-Sachs disease, Sandhoff disease, or GM2 gangliosidosis AB variant);

5.4. Method 5, or any of 5.1-5.3, wherein the subject is diagnosed with a mutation in the gene GBA1;

5.5. Method 5, or any of 5.1-5.3, wherein the subject is diagnosed with a mutation in the genes NPC1 and/or NPC2;

5.6. Method 5, or any of 5.1-5.3, wherein the subject is diagnosed with a mutation in the gene HEXA (encoding hexosaminidase A) and/or a mutation in the gene HEXB (encoding hexosaminidase B) and/or a mutation in the gene GM2A (encoding the GM2 ganglioside activator protein);

5.7. Method 5, or any of 5.1-5.6, wherein the subject is diagnosed with Alzheimer's disease or Parkinson's disease;

5.8. Method 5, or any of 5.1-5.7, wherein the subject undergoes treatment with enzyme replacement therapy (ERT), e.g., using a glucocerebrosidase (e.g., imiglucerase, velaglucerase, or taliglucerase), optionally wherein each of such enzyme is a recombinant enzyme;

5.9. Method 5.8, wherein the subject undergoes treatment with one or more of imiglucerase, velaglucerase (e.g., velaglucerase alfa), and taliglucerase (e.g., taliglucerase alfa);

5.10. Method 5.9, wherein the subject undergoes concurrent treatment with imiglucerase;

5.11. Method 5.10, wherein the subject undergoes treatment with imiglucerase at a dosage of from 2.5 units/kg body weight to 80 units/kg body weight every 1 to 3 weeks, e.g., 40 to 60 units/kg body weight every 2 weeks (1 unit of imiglucerase is the amount of enzyme that catalyzes the hydrolysis of 1 micromole of the synthetic substrate p-nitrophenyl-β-D-glucopyranoside per minute at 37° C.);

5.12. Method 5.11, wherein the subject's dosage of imiglucerase at each administration (e.g., every 1 to 3 weeks, e.g., every 2 weeks) is administered as an intravenous (IV) infusion over a period of 1-3 hours (e.g., 1-2 hours);

5.13. Method 5 or any of 5.1-5.12, wherein the subject has been administered enzyme replacement therapy (e.g., imiglucerase, velaglucerase, and/or taliglucerase) prior to the initiation of any optional treatment with the compound according to Formula (I) (or any of (II)-(XII), (Ia)-(XIIa), or (Ib)-(XIIb), or any of Compounds 1 or 1.1 to 1.75);

5.14. Method 5.13, wherein the subject has been administered imiglucerase therapy for at least 6 months prior to beginning optional therapy with the compound according to Formula (I) (or any of (II)-(XII), (Ia)-(XIIa), or (Ib)-(XIIb), or any of Compounds 1 or 1.1 to 1.75), for example, at least 12 months (1 year), or at least 18 months, or at least 2 years, or at least 3 years.

5.15. Method 5.13 or 5.14, wherein the subject has been administered imiglucerase therapy for at least 6 months at a stable dose prior to beginning optional therapy with the compound according to Formula (I) (or any of (II)-(XII), (Ia)-(XIIa), or (Ib)-(XIIb), or any of Compounds 1 or 1.1 to 1.75);

5.16. Method 5 or any of 5.1-5.15, wherein the method further comprises the step of transitioning the subject from ERT therapy (e.g., imiglucerase, velaglucerase, or taliglucerase) to the optional treatment with the compound according to Formula (I) (or any of (II)-(XII), (Ia)-(XIIa), or (Ib)-(XIIb), or any of Compounds 1 or 1.1 to 1.75);

5.17. Method 5 or any of 5.1-5.16, wherein the subject has a hemoglobin level of at least 11 g/dL for females and at least 12 g/dL for males;

5.18. Method 5, or any of 5.1-5.17, wherein the subject has a platelet count of at least 100,000/cubic millimeter;

5.19. Method 5, or any of 5.1-5.18, wherein the subject has a splenic volume of less than 10 multiples of normal (MN) and/or a hepatic volume of less than 1.5 MN;

5.20. Method 5, or any of 5.1-5.19, wherein the subject is diagnosed with a concurrent dementia, e.g., Alzheimer's disease or Parkinson's disease;

5.21. Method 5, or any of 5.1-5.20, wherein the subject is at least 18 years of age (e.g., 18-30 years of age) at the start of treatment with the compound according to Formula (I) (or any of (II)-(XII), (Ia)-(XIIa), or (Ib)-(XIIb), or any of Compounds 1 or 1.1 to 1.75);

5.22. Method 5, or any of 5.1-5.21, wherein the subject has a glucosylceramide (GL1) concentration of 4.4-11.1 ng/mL in cerebrospinal fluid (CSF) and 4.9-8.3 pg/mL in plasma;

5.23. Method 5, or any of 5.1-5.22, wherein the subject has a glucosylsphingosine (lyso-GL1) concentration of 20.1-67.6 pg/mL in CSF and 8.8-159.0 ng/mL in plasma;

5.24. Method 5, or any of 5.1-5.23, wherein the subject is a human adult patient, e.g., of an age from 18 to 80 years old, e.g., from 18 to 60 years old, or from 18 to years old, or from 18 to 30 years old, or from 18 to 25 years old;

5.25. Method 5, or any of 5.1-5.23, wherein the subject is a human pediatric patient, e.g., of an age from 0 to 18 years old, e.g., from 1 to 15 years old, or from 1 to 5 years old, or from 5 to 10 years old, or from 10 to 15 years old, or from 10 to 18 years old;

5.26. Method 5, or any of 5.1-5.25, wherein measuring of brain tissue volume of the subject is by brain positron emission tomography (PET) or by volumetric magnetic resonance imaging (vMRI);

5.27. Method 5, or any of 5.1-5.26, wherein the subject is found to have brain tissue volume lower than the reference standard;

5.28. Method 5.28, wherein comparison against the reference standard indicates that the subject has a lower brain tissue volume in one or more brain regions selected from: right accumbens, left putamen, left entorhinal cortex, right putamen, right postcentral lobe, left pericalcarine, right amygdala, left cuneus, and left lingual;

5.29. Method 5.27 or 5.28, wherein comparison against the reference standard indicates that the subject has a lower brain tissue volume in one or more brain regions associated with executive function;

5.30. Method of any of 5.27 to 5.29, wherein comparison against the reference standard indicates that the subject has a lower brain tissue volume in one or more brain regions where loss of neuronal connectivity is assessed to be present, e.g., as shown using functional magnetic resonance imaging (fMRI);

5.31. Method of any of 5.27 to 5.30, wherein comparison against the reference standard indicates that the subject has a lower whole brain tissue volume;

5.32. Method of any of 5.27 to 5.31, wherein the method further comprises commencing treatment of the subject by administering to the subject an effective amount of a quinuclidine compound as described herein, e.g., a compound according to Formula (I) or any of (II)-(XII), (Ia)-(XIIa), or (Ib)-(XIIb), or any of Compounds 1 or 1.1 to 1.75;

5.33. Method 5.32, wherein the method further comprises commencing treatment of the subject by administering TAM to the subject an effective amount of a compound according to Formula (I) or any of (II)-(XII), (Ia)-(XIIa), or (Ib)-(XIIb), or any of Compounds 1 or any of 1.1 to 1.75;

5.34. Method 5.32 or 5.33, wherein the method further comprises commencing treatment of the subject by administering to the subject an effective amount Compound 1 or any one or more of Compounds 1.1 to 1.75;

5.35. Method 5.32-5.34, wherein the treatment comprises administering to the subject an effective amount of a pharmaceutical composition comprising the compound according to Formula (I) or any of (II)-(XII), (Ia)-(XIIa), or (Ib)-(XIIb), or any of Compounds 1 or any of 1.1 to 1.75;

5.36. Method 5.32-5.35, wherein the treatment comprises administering to the subject an effective amount of a pharmaceutical composition comprising the Compound 1 or any one or more of Compounds 1.1 to 1.75;

5.37. Method 5.35 or 5.36, wherein the pharmaceutical composition further comprises at least one pharmaceutically acceptable excipient, as described herein;

5.38. Method 5.32-5.37, wherein the method further comprises commencing treatment of the subject by administering a pharmaceutical dosage form comprising an effective amount of the compound or an effective amount of the pharmaceutical composition;

5.39. Method 5.38, wherein the dosage form is an oral dosage form (e.g., a pill, capsule, caplet, tablet, dragee, powder, granule, film, lozenge, or liquid);

5.40. Method 5.39, wherein the dosage form is a chewable tablet;

5.41. Method 5.38, wherein the dosage form is a parenteral dosage form (e.g., wherein the pharmaceutical composition is formulated for injection);

5.42. Method 5.41, wherein the injection is intravenous, intramuscular, intrathecal or subcutaneous injection, optionally a sterile injection;

5.43. Method 5.38, wherein the dosage form is a topical or rectal dosage form;

5.44. Method 5.38, wherein the dosage form is an intranasal dosage form (e.g., an aerosol);

5.45. Method 5.32-5.44, wherein the treatment further comprises concurrently administering a second active agent, e.g., a second compound capable of reducing levels of glycosylceramide in a patient in need thereof, as described herein;

5.46. Method 5.45, wherein the second active agent is administrated in the same pharmaceutical composition or dosage form as the quinuclidine compound;

5.47. Method 5.45 or 5.46, wherein the second active agent is a GCS inhibitor (e.g., miglustat or eliglustat);

5.48. Method of any of 5.32-5.47, wherein the compound is (S)-quinuclidin-3-yl (2-(2-(4-fluorophenyl)thiazol-4-yl)propan-2-yl)carbamate or quinuclidin-3-yl (2-(4'-fluoro-[1,1'-biphenyl]-3-yl)propan-2-yl)carbamate;

5.49. Method 5.48, wherein the dosage of the compound is 15 mg/day orally administered;

5.50. Method 5.49, wherein the dosage of the compound is 15 mg/day in a single oral dose;

5.51. Method of any of 5.32-5.48, wherein the subject is administered a single daily dose of 5 mg, 10 mg, 15 mg, or 20 mg of the compound, e.g., of (S)-quinuclidin-3-yl (2-(2-(4-fluorophenyl)thiazol-4-yl)propan-2-yl)carbamate, optionally in malate salt acid addition salt form;

5.52. Method of any of 5.32-5.51, wherein brain tissue volume of the subject is measured a plurality of times, intermittently or routinely, e.g., weekly, monthly, every 2, 3, 4, 6, 9, 12 months, etc., after the treatment with the compound according to Formula (I) is commenced to assess a change in brain tissue volume;

5.53. Method 5, or any of 5.1-5.52, wherein the subject is a mammalian animal;

5.54. Method 5.53, wherein the subject is a primate animal;

5.55. Method 5.54, wherein the subject is a human.

It will be appreciated that in some embodiments, the Methods 5 et seq., may alternatively be viewed as methods of treating or preventing a neurological disorder associated with a lysosome storage disease, in a subject (e.g., patient) in need thereof and at risk of developing said neurological disorder, the method comprising assessing the onset of the neurological disorder associated with the lysosome storage disease, and wherein said method comprises the steps of: a) measuring the brain tissue volume of the subject (e.g. using vMRI) and comparing against a reference standard to assess whether brain tissue volume is lower than the reference standard; b) where the brain tissue volume identified in step (a) is lower than the reference standard, identifying the onset of said neurological disorder; and c) commencing treatment of the subject by administering to the subject an effective amount of a quinuclidine compound as described herein, e.g., a compound according to Formula (I) or any of (II)-(XII), (Ia)-(XIIa), or (Ib)-(XIIb), or any of Compounds 1 or 1.1 to 1.75. In embodiments, the treatment in c) may be effected with any one of Method 1, Method 2, and Method 3 described herein.

All of the methods described herein (e.g., Method 1, Method 2, Method 3, Method 4, Method 5, as well as any of the embodiments of those methods described above) may be useful in subjects who meet one or more or all of the following criteria:

a) being 18 years of age or older;

b) having a clinical diagnosis of Gaucher disease, e.g., having been diagnosed with or determined to be at risk of developing Gaucher disease (e.g., Gaucher disease type 3). The diagnosis may be made by any assessment described herein, e.g., by virtue of having a mutation in a gene as described herein;

c) having a documented deficiency of acid beta-glucosidase activity;

d) having received, prior to commencement of treatment, at least 3 years of treatment with ERT, such as treatment with imiglucerase (Cerezyme), at a stable monthly dose for at least 6 months;

e) having a hemoglobin level of ≥11.0 g/dL for females and >12.0 g/dL for males;

f) having a platelet count ≥100 000/mm3;

g) having a spleen volume <10 multiples of normal (MN), or total splenectomy (provided the splenectomy occurred >3 years prior to randomization);

h) having a liver volume <1.5 MN;

i) having no bone crisis and being free of symptomatic bone disease (such as bone pain attributable to osteonecrosis and/or pathological fractures) within three months or one year prior to commencement of treatment;

j) having a history of seizures except for myoclonic seizures;

k) having Gaucher disease type 3 which features oculomotor apraxia (supranuclear gaze palsy) characterized by a horizontal saccade abnormality; and l) having mild neurological involvement or moderate neurological involvement, as measured using the Modified Severity Scoring Tool (mSST; Davies, et al., 2011), at the time of commencement of treatment.

In an embodiment of Method 1 described herein, or in a specific sub-embodiment of Method 1 described herein, the subject meets all of the criteria (a) to (1). In an embodiment of Method 2 described herein, or in a specific sub-embodiment of Method 2 described herein, the subject meets all of the criteria (a) to (1). In an embodiment of Method 3 described herein, or in a specific sub-embodiment of Method 3 described herein, the subject meets all of the criteria (a) to (1). In an embodiment of Method 4 described herein, or in a specific sub-embodiment of Method 4 described herein, the subject meets all of the criteria (a) to (1). In an embodiment of Method 5 described herein, or in a specific sub-embodiment of Method 5 described herein, the subject meets all of the criteria (a) to (1).

In further embodiments, the subject is an adult or pediatric patient ≥12 years of age. In embodiments, the subject is an adult or pediatric patient ≥12 years of age with Gaucher disease Type 3 (as confirmed, for instance, by satisfying criteria b) and/or k) above) and who is stabilized with ERT, e.g., imiglucerase (Cerezyme) for systemic conditions. Systemic conditions may, for instance, be characterized by the presence of markers for systemic disease, such as those associated with: i) spleen and liver volume (e.g., as measured by magnetic resonance imaging (MRI)); ii) platelet count; and iii) hemoglobin levels. In some embodiments, the subject with Gaucher disease Type 3 has been receiving treatment with ERT (for instance, using imiglucerase (Cerezyme)) for at least 3 years and/or has reached the following GD therapeutic goals: one or more, or all, of criteria e) to i) above are satisfied.

In a specific embodiment, the invention provides (S)-quinuclidin-3-yl (2-(2-(4-fluorophenyl)thiazol-4-yl)propan-2-yl)carbamate in a single oral dose of 15 mg/day, optionally in malate salt acid addition salt form, for use in the methods defined herein (e.g. Method 1, Method 2, Method 3, Method 4, Method 5, as well as any of the embodiments of the said methods described above) in a subject with Gaucher disease Type 3 (as confirmed, for instance, by satisfying criteria b) and/or k) above) who is stabilized with ERT, e.g. imiglucerase (Cerezyme) for systemic conditions (such as defined above), wherein the subject is an adult or pediatric patient ≥12 years of age.

A positive effect on cognitive dysfunction and/or neuronal connectivity and/or brain tissue volume and/or regression of neurological disorder as described in Method 1, Method 2, Method 3, and Method 4, respectively, may be understood as a treatment of CNS manifestations. Thus, in a specific embodiment, the invention provides (S)-quinuclidin-3-yl (2-(2-(4-fluorophenyl)thiazol-4-yl)propan-2-yl)carbamate in a single oral dose of 15 mg/day, optionally in malate salt acid addition salt form, for use in the treatment of CNS manifestations in a subject with Gaucher Disease Type 3 (as confirmed, for instance, by satisfying criteria b) and/or k) above) who is stabilized with ERT, e.g. imiglucerase (Cerezyme) for systemic conditions (such as defined above), wherein the subject is an adult or pediatric patient ≥12 years of age.

In embodiments of each of the methods described herein (e.g., Method 1, Method 2, Method 3, Method 4, Method 5, as well as any of the embodiments of the said methods described above), the subject to be treated does not undergo concurrent treatment with a CYP3A inducer, e.g., a strong CYP3A inducer such as rifampin, or a moderate CYP3A inducer such as phenobarbital or efavirenz. In embodiments, the subject is not taking a dietary supplement identified as being a strong or moderate inducer of CYP3A.

In one embodiment, the invention provides (S)-quinuclidin-3-yl (2-(2-(4-fluorophenyl)thiazol-4-yl)propan-2-yl)carbamate in a single oral dose of 15 mg/day, optionally in malate salt acid addition salt form, for use in the treatment of CNS manifestations in a subject with Gaucher Disease Type 3 (as confirmed, for instance, by satisfying criteria b) and/or k) above) who is stabilized with ERT, e.g. imiglucerase (Cerezyme) for systemic conditions (such as defined above), wherein the subject is an adult or pediatric patient ≥12 years of age and wherein the subject to be treated does not undergo concurrent treatment with a CYP3A inducer, e.g., a strong CYP3A inducer such as rifampin, or a moderate CYP3A inducer such as phenobarbital or efavirenz. In embodiments, the subject is not taking a dietary supplement identified as being a strong or moderate inducer of CYP3A.

All of the methods described herein (e.g., Method 1, Method 2, Method 3, Method 4, Method 5, as well as any of the embodiments of those methods described above) may be deemed unsuitable for certain patient groups, for example, those having certain pre-existing conditions, those with current or past treatment with some medications and those with history of treatments, such as surgical treatments, as assessed and described herein. A prescribing physician will be qualified to decide whether a subject's particular condition(s), and/or current or past medication(s) affect their suitability for undergoing methods of treatment according to the methods disclosed herein.

In embodiments, the subjects to be treated by the methods described herein (e.g., Method 1, Method 2, Method 3, Method 4, Method 5, as well as any of the embodiments of those methods described above) do not include those who meet one or more or all of the following criteria:

1) has had substrate reduction therapy or chaperone therapy for Gaucher Disease within 6 months prior to the commencement of treatment;
2) has had a partial or total splenectomy within 3 years prior to the commencement of treatment;
3) is blood transfusion-dependent;
4) has had prior esophageal varices or liver infarction or current liver enzymes (alanine aminotransferase [ALT]/aspartate aminotransferase [AST]) or total bilirubin >2 times the upper limit of normal, unless the patient has a diagnosis of Gilbert Syndrome;
5) has clinically significant disease, other than Gaucher Disease, including cardiovascular (congenital cardiac defect, coronary artery disease, valve disease or left sided heart failure; clinically significant arrhythmias or conduction defect), hepatic, gastrointestinal, pulmonary, neurologic, endocrine, metabolic (e.g., hypokalemia, hypomagnesemia) or psychiatric disease, other medical conditions, or serious intercurrent illnesses that may preclude participation;
6) has renal insufficiency, as defined by an estimated glomerular filtration rate <30 mL/min/1.73 m2;
7) has a history of cancer, with the exception of basal cell carcinoma;
8) has myoclonic seizures;
9) is pregnant or lactating;
10) has a cortical cataract greater than one quarter of the lens circumference (Grade cortical cataract-2) or a posterior subcapsular cataract greater than 2 mm (Grade posterior subcapsular cataract-2), according to World Health Organization (WHO) Grading.

11) requires use of invasive ventilatory support;
12) requires use of noninvasive ventilator support while awake for longer than 12 hours daily;
13) currently receiving potentially cataractogenic medications (corticosteroids, psoralens used in dermatology with ultraviolet light therapy [PUVA], typical antipsychotics, and glaucoma medications) or any medication that may worsen the vision of a patient with cataract (e.g., alpha-adrenergic glaucoma medications);
14) administered strong or moderate inducers or inhibitors of CYP3A within 15 days or 5 half-lives from screening, whichever is longer, prior to commencement of treatment, or consumption of grapefruit, grapefruit juice, or grapefruit containing products within 72 hours of commencement of treatment;
15) is scheduled for in-patient hospitalization including elective surgery, during treatment; and
16) has had a major organ transplant (e.g., bone marrow or liver).

Pharmaceutical Compositions

The present disclosure also provides pharmaceutical compositions comprising at least one quinuclidine compound as described herein and at least one pharmaceutically acceptable excipient, e.g., for use according to the methods disclosed herein. The pharmaceutically acceptable excipient can be any such excipient known in the art including those described in, for example, Remington's Pharmaceutical Sciences, Mack Publishing Co. (A. R. Gennaro edit. 1985). Pharmaceutical compositions of the compounds presently disclosed may be prepared by conventional means known in the art including, for example, mixing at least one presently disclosed compound with a pharmaceutically acceptable excipient.

Thus, in one aspect the present disclosure provides a pharmaceutical dosage form comprising a quinuclidine compound as described herein and a pharmaceutically acceptable excipient, wherein the dosage form is formulated to provide, when administered (e.g., when administered orally), an amount of said compound sufficient to treat a disease or disorder as provided in any of the Methods described herein (e.g., Method 1 et seq., Method 2 et seq., Method 3 et seq., Method 4 et seq., or Method 5 et seq.).

A pharmaceutical composition or dosage form of the invention can include an agent and another carrier, e.g., compound or composition, inert or active, such as a detectable agent, label, adjuvant, diluent, binder, stabilizer, buffers, salts, lipophilic solvents, preservative, adjuvant, or the like. Carriers also include pharmaceutical excipients and additives, for example, proteins, peptides, amino acids, lipids, and carbohydrates (e.g., sugars, including monosaccharides, di-, tri-, tetra-, and oligosaccharides; derivatized sugars such as alditols, aldonic acids, esterified sugars, and the like; and polysaccharides or sugar polymers), which can be present singly or in combination, comprising alone or in combination 1 to 99.99% by weight or volume. Exemplary protein excipients include serum albumin such as human serum albumin (HSA), recombinant human albumin (rHA), gelatin, casein, and the like.

Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), and myoinositol.

Carriers which may be used include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

The present disclosure also provides pharmaceutical compositions, and kits comprising said compositions, which contain at least one quinuclidine compound as described herein and at least one further pharmaceutically-active agent. These pharmaceutical compositions and kits may be adapted to allow simultaneous, subsequent, and/or separate administration of the quinuclidine compound and the further active agent. For example, the quinuclidine compound and the further active agent may be formulated in separate dosage forms, e.g., in separate tablets, capsules, lyophilizates, or liquids, or they may be formulated in the same dosage form, e.g., in the same tablet, capsule, lyophilizate, or liquid. Where the quinuclidine compound and the further active agent are formulated in the same dosage form, the quinuclidine compound and the further active agent may be present substantially in admixture, e.g., within the core of a tablet, or they may be present substantially in discrete regions of the dosage form, e.g., in separate layers of the same tablet. In one embodiment, the pharmaceutical dosage form comprises a further agent which is capable of treating or preventing cognitive dysfunction and/or gait abnormalities, e.g., in a patient having, diagnosed with or predisposed to a lysosomal storage disease, such as Gaucher Type 3 or Niemann-Pick Type C, as described herein.

In a further aspect the present disclosure provides a pharmaceutical composition comprising: (i) a quinuclidine compound as described herein; (ii) a further active agent; and (iii) a pharmaceutically acceptable excipient. In one embodiment, the further active agent is an agent which is capable of treating or preventing cognitive dysfunction and/or gait abnormalities, e.g., in a patient having, diagnosed with or predisposed to a lysosomal storage disease, such as Gaucher Type 3 or Niemann-Pick Type C, as described herein. In one embodiment, the further active agent is capable of treating or preventing a gait disorder (e.g., ataxia) or dementia, e.g., in a patient having, diagnosed with or predisposed to a lysosomal storage disease, such as Gaucher Type 3 or Niemann-Pick Type C, as described herein, when administered orally to a subject.

The presently disclosed quinuclidine compounds and pharmaceutical compositions can be used in an animal or human. Thus, a presently disclosed compound can be formulated as a pharmaceutical composition for oral, buccal, parenteral (e.g., intravenous, intramuscular, or subcutaneous), topical, rectal, or intranasal administration or in a form suitable for administration by inhalation or insufflation. In particular embodiments, the quinuclidine compound or pharmaceutical composition is formulated for systemic administration, e.g., via a non-parenteral route. In one embodiment, the quinuclidine compound or pharmaceutical composition is formulated for oral administration, e.g., in solid form. Such modes of administration and the methods for preparing appropriate pharmaceutical compositions are described, for example, in Gibaldi's Drug Delivery Systems in Pharmaceutical Care (1st ed., American Society of Health-System Pharmacists 2007).

The pharmaceutical compositions can be formulated so as to provide slow, extended, or controlled release of the active ingredient therein using, for example, hydroxypropyl methyl cellulose in varying proportions to provide the desired release profile, other polymer matrices, liposomes, and/or microspheres. The pharmaceutical compositions can also optionally contain opacifying agents and may be of a composition that releases the active ingredient(s) only, or preferentially, in a certain portion of the gastrointestinal tract, optionally, in a delayed manner, e.g., by using an enteric coating. Examples of embedding compositions include polymeric substances and waxes. The active ingredient can also be in micro-encapsulated form, if appropriate, with one or more pharmaceutically acceptable carriers, excipients, or diluents well known in the art (see, e.g., Remington's). The compounds presently disclosed may be formulated for sustained delivery according to methods well known to those of ordinary skill in the art. Examples of such formulations can be found in U.S. Pat. Nos. 3,119,742; 3,492,397; 3,538,214; 4,060,598; and 4,173,626.

In solid dosage forms for oral administration (e.g., capsules, tablets, pills, dragees, powders, granules, and the like), the active ingredient is mixed with one or more pharmaceutically acceptable carriers, excipients, or diluents, such as sodium citrate or dicalcium phosphate, and/or any of the following: (1) fillers or extenders, such as starches, lactose, sucrose, glucose, mannitol, microcrystalline cellulose, calcium phosphate, and/or silicic acid; (2) binders, such as, for example, carboxymethylcellulose, alginates, gelatin, pregelatinized maize starch, polyvinyl pyrrolidone, hydroxypropyl methylcellulose, sucrose, and/or acacia; (3) humectants, such as glycerol; (4) disintegrating agents, such as agar-agar, calcium carbonate, sodium starch glycolate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, sodium lauryl sulphate, acetyl alcohol, and glycerol monostearate; (8) absorbents, such as kaolin and bentonite clay; (9) lubricants, such as talc, silica, calcium stearate, magnesium stearate, solid polyethylene glycols, sodium lauryl sulfate, and mixtures thereof; and (10) coloring agents. In the case of capsules, tablets, and pills, the pharmaceutical compositions can also comprise buffering agents. Solid compositions of a similar type can also be prepared using fillers in soft and hard-filled gelatin capsules, and excipients such as lactose or milk sugars, as well as high molecular weight polyethylene glycols and the like.

A tablet can be made by compression or molding, optionally with one or more accessory ingredients. Compressed tablets can be prepared using binders (for example, gelatin or hydroxypropyl methyl cellulose), lubricants, inert diluents, preservatives, disintegrants (for example, sodium starch glycolate or cross-linked sodium carboxymethyl cellulose), surface-actives, and/or dispersing agents. Molded tablets can be made by molding in a suitable machine a mixture of the powdered active ingredient moistened with an inert liquid diluent.

The tablets and other solid dosage forms, such as dragees, capsules, pills, and granules, can optionally be scored or prepared with coatings and shells, such as enteric coatings and other coatings well known in the art.

In embodiments, the pharmaceutical compositions are administered orally in a liquid form.

Liquid dosage forms for oral administration of an active ingredient include pharmaceutically acceptable emulsions, microemulsions, solutions, suspensions, syrups, and elixirs. Liquid preparations for oral administration may be presented as a dry product for constitution with water or other suitable vehicle before use. In addition to the active ingredient, the liquid dosage forms can contain inert diluents commonly used in the art, such as, for example, water or other solvents, solubilizing agents, and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor, and sesame oils), glycerol, tetrahydrofuryl alcohol, polyethylene glycols, and fatty acid esters of sorbitan, and mixtures thereof. In addition to inert diluents, the liquid pharmaceutical compositions can include adjuvants such as wetting agents, emulsifying and suspending agents, sweetening, flavoring, coloring, perfuming and preservative agents, and the like.

Suspensions, in addition to the active ingredient(s) can contain suspending agents such as, but not limited to, ethoxylated isostearyl alcohols, polyoxyethylene sorbitol and sorbitan esters, microcrystalline cellulose, aluminum metahydroxide, bentonite, agar-agar, and tragacanth, and mixtures thereof. Suitable liquid preparations may be prepared by conventional means with a pharmaceutically acceptable additive(s) such as a suspending agent (e.g., sorbitol syrup, methyl cellulose, or hydrogenated edible fats); emulsifying agent (e.g., lecithin or acacia); non-aqueous vehicle (e.g., almond oil, oily esters, or ethyl alcohol); and/or preservative (e.g., methyl or propyl p-hydroxybenzoates or sorbic acid). The active ingredient(s) can also be administered as a bolus, electuary, or paste.

For buccal administration, the composition may take the form of tablets or lozenges formulated in a conventional manner.

In embodiments, the pharmaceutical compositions are administered by non-oral means such as by topical application, transdermal application, injection, and the like. In related embodiments, the pharmaceutical compositions are administered parenterally by injection, infusion, or implantation (e.g., intravenous, intramuscular, intra-arterial, subcutaneous, and the like).

Presently disclosed compounds may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions, or emulsions in oily or aqueous vehicles, and may contain a formulating agent such as a suspending, stabilizing, and/or dispersing agent recognized by those of skill in the art.

Alternatively, the active ingredient may be in powder form for reconstitution with a suitable vehicle, e.g., sterile pyrogen-free water, before use.

The pharmaceutical compositions may be administered directly to the central nervous system. Accordingly, in certain embodiments the compositions are administered directly to the central nervous system so as to avoid the blood brain barrier. In some embodiments, the composition can be administered via direct spinal cord injection. In embodiments, the composition is administered by intrathecal injection. In some embodiments, the composition is administered via intracerebroventricular injection. In embodiments, the composition is administered into a cerebral lateral ventricle. In embodiments, the composition is administered into both cerebral lateral ventricles. In additional embodiments, the composition is administered via intrahippocampal injection. The compositions may be administered in one injection or in multiple injections. In other embodiments, the composition is administered to more than one location (e.g., to two sites in the central nervous system).

The pharmaceutical compositions can be in the form of sterile injections. The pharmaceutical compositions can be sterilized by, for example, filtration through a bacteria-retaining filter, or by incorporating sterilizing agents in the form of sterile solid compositions which can be dissolved in sterile water, or some other sterile injectable medium immediately before use. To prepare such a composition, the active ingredient is dissolved or suspended in a parenterally acceptable liquid vehicle. Exemplary vehicles and solvents include, but are not limited to, water, water adjusted to a suitable pH by addition of an appropriate amount of hydrochloric acid, sodium hydroxide or a suitable buffer, 1,3-butanediol, Ringer's solution, and isotonic sodium chloride solution. The pharmaceutical composition can also contain one or more preservatives, for example, methyl, ethyl, or n-propyl p-hydroxybenzoate. To improve solubility, a dissolution enhancing or solubilizing agent can be added or the solvent can contain 10-60% w/w of propylene glycol or the like.

The pharmaceutical compositions can contain one or more pharmaceutically acceptable sterile isotonic aqueous or nonaqueous solutions, dispersions, suspensions or emulsions, or sterile powders, which can be reconstituted into sterile injectable solutions or dispersions just prior to use. Such pharmaceutical compositions can contain antioxidants; buffers; bacteriostats; solutes, which render the formulation isotonic with the blood of the intended recipient; suspending agents; thickening agents; preservatives; and the like.

Examples of suitable aqueous and nonaqueous carriers, which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In some embodiments, in order to prolong the effect of an active ingredient, it is desirable to slow the absorption of the compound from subcutaneous or intramuscular injection. This can be accomplished by the use of a liquid suspension of crystalline or amorphous material having poor water solubility. The rate of absorption of the active ingredient then depends upon its rate of dissolution which, in turn, can depend upon crystal size and crystalline form. Alternatively, delayed absorption of a parenterally-administered active ingredient is accomplished by dissolving or suspending the compound in an oil vehicle. In addition, prolonged absorption of the injectable pharmaceutical form can be brought about by the inclusion of agents that delay absorption such as aluminum monostearate and gelatin.

Controlled release parenteral compositions can be in form of aqueous suspensions, microspheres, microcapsules, magnetic microspheres, oil solutions, oil suspensions, emulsions, or the active ingredient can be incorporated in biocompatible carrier(s), liposomes, nanoparticles, implants, or infusion devices. Materials for use in the preparation of microspheres and/or microcapsules include, but are not limited to, biodegradable/bioerodible polymers such as polyglactin, poly-(isobutyl cyanoacrylate), poly(2-hydroxyethyl-L-glutamine), and poly(lactic acid). Biocompatible carriers which can be used when formulating a controlled release parenteral formulation include carbohydrates such as dextrans, proteins such as albumin, lipoproteins, or antibodies. Materials for use in implants can be non-biodegradable, e.g., polydimethylsiloxane, or biodegradable such as, e.g., poly(caprolactone), poly(lactic acid), poly(glycolic acid), or poly(ortho esters). For topical administration, a presently disclosed compound may be formulated as an ointment or cream. Presently disclosed compounds may also be formulated in rectal compositions such as suppositories or retention enemas, e.g., containing conventional suppository bases such as cocoa butter or other glycerides.

For intranasal administration or administration by inhalation, presently disclosed compounds may be conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. The pressurized container or nebulizer may contain a solution or suspension of the presently disclosed compound. Capsules and cartridges (made, for example, from gelatin) for use in an inhaler or insufflator may be formulated containing a powder mix of a presently disclosed compound and a suitable powder base such as lactose or starch.

Generally, the agents and compositions described herein are administered in an effective amount or quantity sufficient to treat or prevent cognitive dysfunction and/or gait abnormalities in a subject in need thereof. Typically, the dose can be adjusted within this range based on, e.g., age, physical condition, body weight, sex, diet, time of administration, and other clinical factors. Determination of an effective amount is well within the capability of those skilled in the art.

Having been generally described herein, the follow non-limiting examples and appended FIGURE are provided to further illustrate this invention, wherein:

FIG. 1 is a graph showing change in mean whole brain volume (WBV) after 52 weeks of a treatment with a compound of Formula (I) for Group A patients and change in WBV for Patient 5, determined from vMRI measurements and TBM analysis according to Example 5 herein.

EXAMPLES

General Procedures for Chemical Synthesis
General Procedure A: Carbamate Formation with Triphosgene To a suspension of amine hydrochloride (1 equivalent) and triethylamine (3-4 equivalents) in a THF (concentration~0.2M) at room temperature was added triphosgene (0.35 equivalents). The reaction mixture was stirred for 10 min and small amount of ether (1-2 mL) was added. The triethylammonium salt was filtered off to afford a clear solution of isocyanate in THF/ether.

To a solution of alcohol (1.5 equivalents) in THF (concentration~0.2M) at room temperature was added NaH [60%, oil] (1.5 equivalents). The reaction mixture was stirred for 15 min and the above solution (isocyanate in THF/ether) was added dropwise. In a standard workup, the reaction was quenched with brine. The solution was extracted with EtOAc and the organic layer was dried over $Na_2SO_4$, filtered, and concentrated. The crude material was purified on combiflash ($SiO_2$ cartridge, $CHCl_3$ and 2N $NH_3$ in MeOH) to afford the corresponding carbamate.

General Procedure B: Alkylation with Organocerium

A suspension of $CeCl_3$ (4 equivalents) in THF (concentration—0.2M) was stirred at room temperature for 1 h. The suspension was cooled to −78° C. and MeLi/Ether [1.6M] (4 equivalents) was added dropwise. The organocerium complex was allowed to form for a period of 1 h and a solution of nitrile (1 equivalent) in THF (concentration 2.OM) was added dropwise. The reaction mixture was warmed up to room temperature and stirred for 18 h. The solution was cooled to 0° C. and quenched with water (~1 mL) followed by addition of 50% aqueous solution of ammonium hydroxide (~3 mL) until precipitated formed and settled to the bottom of the flask. The mixture was filtered through a pad of celite and concentrated. The crude material was treated with a solution of HCl/dioxane [4.OM]. The intermediate arylpropan-2-amine hydrochloride was triturated in ether and used as is for the next step. Alternatively, the crude free base amine was purified on combiflash ($SiO_2$ cartridge, $CHCl_3$ and 2N $NH_3$ in MeOH) to afford the corresponding arylpropylamine.

General Procedure C: Suzuki Coupling

To a solution of aryl halide (1 equivalent) in a mixture of DME/water [4:1] (concentration ~0.2M) was added boronic acid (2 equivalents), palladium catalyst (0.1-0.25 equivalent), and sodium carbonate (2 equivalents). The reaction mixture was microwaved 25 min at 150° C. After filtering through a celite plug and concentrating, the crude product was purified on combiflash ($SiO_2$ cartridge, $CHCl_3$ and 2N $NH_3$ in MeOH) to afford the corresponding coupling adduct.

Alternatively: To a solution of aryl halide (1 equivalent) in a mixture of toluene/water [20:1](concentration~0.2 M) was added boronic acid (1.3-2.5 equivalents), palladium catalyst (0.05-0.15 equivalent), tricyclohexylphosphine (0.15-0.45 equivalent), and potassium phosphate (5 equivalents). The reaction mixture was microwaved 25 min at 150° C. After filtering through a celite plug and concentrating, the crude product was purified on combiflash ($SiO_2$ cartridge, $CHCl_3$ and 2N $NH_3$ in MeOH) to afford the corresponding coupling adduct.

General Procedure D: Cyclopropanation

To a mixture of aryl nitrile (1 equivalent) and $Ti(Oi-Pr)_4$ (1.7 equivalents) stirring at −70° C., was added dropwise EtMgBr [3.0 M in ether] (1.1 equivalents). The reaction mixture was allowed to warm to 25° C. and stirred for 1 h. To the above mixture was added $BF_3 \cdot Et_2O$ (3 equivalents) dropwise at 25° C. After the addition, the mixture was stirred for another 2 h, and then quenched with aqueous HCl [2M]. The resulting solution was then basified by adding aqueous NaOH [2M]. The organic material was extracted with ethyl ether. The organic layers were combined, dried over $Na_2SO_4$, filtered, and concentrated. The crude material was purified by silica gel column chromatography (eluting with petroleum ether/EtOAc: 10/1 to 1/1) to give the corresponding 1-aryl-cyclopropanamine.

General Procedure E: Biaryl coupling using Suzuki conditions

To a stirred solution of the aryl halide component (1 equivalent) in 5:1 (v/v) dioxane/water (~0.15 M) or 5:1 (v/v) N,N-dimethylformamide (~0.15 M) was added the arylboronate or arylboronic acid component (1-1.5 equivalents), sodium carbonate (2-3 equivalents), and [1,1'-bis(diphenylphosphino)ferrocene]dichloropalladium(II) (0.05 equivalents). The mixture was heated (90° C.) overnight and then filtered through a plug of Celite. The Celite was rinsed with ethyl acetate and the combined filtrate was washed with brine, dried ($Na_2SO_4$), and concentrated. The residue was purified by flash chromatography over silica.

General Procedure F: Carbamate Formation Using an Isocyanate Generated Via a Mixed Anhydride/Curtius Rearrangement Route To a stirred solution of the carboxylic acid component (1 equivalent) in tetrahydrofuran (~0.1 M) was added triethylamine (2 equivalents). The reaction was cooled (0° C.) and treated with isobutyl chloroformate (1.5 equivalents). After 1 hour at 0° C., a solution of sodium azide (2 equivalents) in water (~1 M) was added and the reaction was allowed to warm to room temperature. After overnight stirring, the reaction was diluted with water and extracted with ethyl acetate. The combined extracts were washed with aqueous sodium bicarbonate solution and brine, dried ($Na_2SO_4$), and concentrated. The crude acyl azide was further dried via coevaporation with toluene and then taken up in toluene (~0.1 M). The stirred solution was refluxed for 2-2.5 hours, cooled, and treated with an alcohol component (1.25-2 equivalents). The reaction was heated at reflux overnight and then concentrated. The residue was taken up in either ethyl acetate or chloroform and washed with aqueous sodium carbonate ($Na_2SO_4$) and concentrated. The crude product was purified by flash chromatography over silica using chloroform/methanol (less polar carbamates) or chloroform/methanol/ammonia (more polar carbamates) solvent gradients.

Example 1: Synthesis of Quinuclidine Compounds 1-azabicyclo[2.2.2]oct-3-yl [2-(4'-fluorobiphenyl-3-yl)propan-2-yl]carbamate (Compound Using General Procedure C, 1-azabicyclo[2.2.2]oct-3-yl [2-(3-bromophenyl)propan-2-yl]carbamate (600 mg, 1.63 mmol), 4-fluorophenyl boronic acid (457 mg, 3.27 mmol), and palladium (II) acetate gave the title compound as a white solid (373 mg; 60%). $^1$H NMR (400 MHz, $CDCl_3$) δ 7.56 (s, 1H), 7.52 (dd, J=5.4, 8.4 Hz, 2H), 7.42-7.38 (m, 3H), 7.12 (m, 2H), 5.18 (5, 1H), 4.62 (s, 1H), 2.66 (m, 6H), 1.72 (s, 6H), 2.01-0.83 (m, 5H) ppm. $^{13}$C NMR (100 MHz, $CDCl_3$) δ 125.0, 124.0, 123.8, 116.0, 116.0, 71.3, 55.9, 55.5, 47.6, 46.7, 29.6, 25.6, 24.8, 19.8 ppm. Purity: 98.0% UPLCMS (210 nm); retention time 0.95 min; (M+1) 382.9. Anal. Calcd. for $C_{23}H_{27}FN_2O_2 \cdot 0.37$ ($CHCl_3$): C, 65.86; H, 6.47; N, 6.57. Found: C, 65.85; H, 6.69; N, 6.49.

(S)-quinuclidin-3-yl 2-(2-(4-fluorophenyl)thiazol-4-yl)propan-2-ylcarbamate (Compound 2)

To a stirred solution of 4-fluorothiobenzamide (8.94 g, 57.6 mmol) in ethanol (70 mL) was added ethyl 4-chloroacetoacetate (7.8 mL, 58 mmol). The reaction was heated at reflux for 4 hours, treated with an addition aliquot of ethyl 4-chloroacetoacetate (1.0 mL, 7.4 mmol), and refluxed for an additional 3.5 hours. The reaction was then concentrated and the residue was partitioned between ethyl acetate (200 mL) and aqueous NaHCO$_3$ (200 mL). The organic layer was combined with a back-extract of the aqueous layer (ethyl acetate, 1×75 mL), dried (Na$_2$SO$_4$), and concentrated. The resulting amber oil was purified by flash chromatography using a hexane/ethyl acetate gradient to afford ethyl 2-(2-(4-fluorophenyl)thiazol-4-yl)acetate as a low melting, nearly colourless solid (13.58 g, 89%).

To a stirred solution of ethyl 2-(2-(4-fluorophenyl)thiazol-4-yl)acetate (6.28 g, 23.7 mmol) in DMF (50 mL) was added sodium hydride [60% dispersion in mineral oil] (2.84 g, 71.0 mmol). The frothy mixture was stirred for 15 minutes before cooling in an ice bath and adding iodomethane (4.4 mL, 71 mmol). The reaction was stirred overnight, allowing the cooling bath to slowly warm to room temperature. The mixture was then concentrated and the residue partitioned between ethyl acetate (80 mL) and water (200 mL). The organic layer was washed with a second portion of water (1×200 mL), dried (Na$_2$SO$_4$) and concentrated.

The resulting amber oil was purified by flash chromatography using a hexane/ethyl acetate gradient to afford ethyl 2-(2-(4-fluorophenyl)thiazol-4-yl)-2-methylpropanoate as a colourless oil (4.57 g, 66%).

To a stirred solution of ethyl 2-(2-(4-fluorophenyl)thiazol-4-yl)-2-methylpropanoate (4.56 g, 15.5 mmol) in 1:1:1 THF/ethanol/water (45 mL) was added lithium hydroxide monohydrate (2.93 g, 69.8 mmol). The reaction was stirred overnight, concentrated, and redissolved in water (175 mL). The solution was washed with ether (1×100 mL), acidified by the addition of 1.0 N HCl (80 mL), and extracted with ethyl acetate (2×70 mL). The combined extracts were dried (Na$_2$SO$_4$) and concentrated to afford 2-(2-(4-fluorophenyl)thiazol-4-yl)-2-methylpropanoic acid as a white solid (4.04 g, 98%). This material was used in the next step without purification.

To a stirred and cooled (0° c.) solution of 2-(2-(4-fluorophenyl)thiazol-4-yl)-2-methylpropanoic acid (4.02 g, 15.2 mmol) in THF (100 mL) was added trimethylamine (4.2 mL, 30 mmol) followed by isobutyl chloroformate (3.0 mL, 23 mmol). The reaction was stirred cold for another 1 hour before adding a solution of sodium azide (1.98 g, 30.5 mmol) in water (20 mL). The reaction was stirred overnight, allowing the cooling bath to slowly warm to room temperature. The mixture was then diluted with water (100 mL) and extracted with ethyl acetate (2×60 mL). The combined extracts were washed with aqueous NaHCO$_3$ (1×150 mL) and brine (1×100 mL), dried (Na$_2$SO$_4$) and concentrated. After coevaporating with toluene (2×50 mL), the resulting white solid was taken up in toluene (100 mL) and refluxed for 4 hours. (S)-3-quinuclidinol (3.87 g, 30.4 mmol) was then added and reflux was continued overnight. The reaction was concentrated and the residue partitioned between ethyl acetate (100 mL) and aqueous NaHCO$_3$ (150 mL). The organic layer was washed with water (1×150 mL), dried (Na$_2$SO$_4$), and concentrated. The resulting off-white solid was purified by flash chromatography using a chloroform/methanol/ammonia gradient to afford the title compound as a white solid (4.34 g, 73%). $^1$H NMR (400 MHz, CDCl$_3$) δ 7.96-7.88 (m, 2H), 7.16-7.04 (m, 3H), 5.55 (br s, 1H), 4.69-4.62 (m, 1H), 3.24-3.11 (m, 1H), 3.00-2.50 (m, 5H), 2.01-1.26 (m, 11H) ppm. $^{13}$C NMR (400 MHz, CDCl$_3$) δ 166.4, 165.1, 163.8 (d, J=250.3 Hz), 162.9, 155.0, 130.1 (d, J=3.3 Hz), 128.4 (d, J=8.5 Hz), 115.9 (d, J=22.3 Hz), 112.5, 71.2, 55.7, 54.2, 47.5, 46.5, 28.0, 25.5, 24.7, 19.6 ppm. Purity: 100% UPLCMS (210 nm & 254 nm); retention time 0.83 min; (M+1) 390.

(S)-quinuclidin-3-yl (2-(4'-(2-methoxyethoxy)-[1,1'-biphenyl]-4-yl)propan-2-yl)carbamate (Compound 3)

Using General Procedure E and the reaction inputs ethyl 2-(4-bromophenyl)-2-methylpropanoate and 4-(2-methoxyethoxy)phenylboronic acid, ethyl 2-(4'-(2-methoxyethoxy)-[1,1'-biphenyl]-4-yl)-2-methylpropanoate was prepared as an off-white solid. To a stirred solution of this compound (3.01 g, 8.78 mmol) in 1:1:1 (v/v/v) tetrahydrofuran/ethanol/water (45 mL) was added lithium hydroxide monohydrate (1.47 g, 61.4 mmol). The mixture was heated at reflux overnight and then concentrated. The residue was dissolved in water, treated with 1N hydrochloric acid (65 mL), and extracted with ethyl acetate. The combined organic layers were washed with brine, dried (Na$_2$SO$_4$), and concentrated to afford 2-(4'-(2-methoxyethoxy)-[1,1'-biphenyl]-4-yl)-2-methylpropanoic acid as a white solid (2.75 g, 100%). This intermediate and (S)-quinuclidin-3-ol were reacted according to General Procedure F to generate the title compound as a colourless, glassy solid. $^1$H NMR (400 MHz, DMSO-d6) δ 7.62-7.29 (m, 7H), 7.01 (d, J=8.9 Hz, 2H), 4.47-4.37 (m, 1H), 4.17-4.08 (m, 2H), 3.72-3.62 (m, 2H), 3.32 (s, 3H), 3.09-2.25 (m, 6H), 2.05-1.18 (m, 11H) ppm. $^{13}$C NMR (100 MHz, DMSO-d6) δ 157.9, 154.5, 146.7, 137.4, 132.5, 127.5, 125.7, 125.2, 114.8, 70.4, 70.0, 66.9, 58.2, 55.4, 54.2, 46.9, 45.9, 29.4, 25.3, 24.2, 19.2 ppm. Purity: 100%, 100% (210 & 254 nm) UPLCMS; retention time: 0.87 min; (M+H+) 439.5.

1-azabicyclo[2.2.2]oct-3-yl [2-(biphenyl-3-yl)propan-2-yl]carbamate (Compound 4)

Using General Procedure C, 1-azabicyclo[2.2.2]oct-3-yl [2-(3-bromophenyl)propan-2-yl]carbamate (600 mg, 1.63 mmol), phenylboronic acid (398 mg, 3.27 mmol), and palladium (II) acetate gave the title compound as a white solid (379 mg, 64%). $^1$H NMR (400 MHz, CDCl$_3$) δ 7.61 (s, 1H), 7.56 (d, J=7.4 Hz, 2H), 7.50-7.38 (m, 4H), 7.34 (m, 2H), 5.16 (s, 1H), 4.63 (s, 1H), 3.39-2.09 (m, 6H), 1.72 (s, 6H), 2.02-0.73 (m, 5H) ppm. $^{13}$C NMR (100 MHz, CDCl$_3$) δ 154.8, 147.8, 141.6, 129.0, 129.0, 128.6, 127.5, 125.8, 125.0, 124.0, 71.6, 71.3, 55.9, 55.5, 47.6, 46.8, 31.5, 30.2, 30.0, 29.5, 25.6, 24.8, 19.8 ppm. Purity: 99% UPLCMS (210 nm); retention time 0.84 min; (M+1) 365.0. Anal. Calcd. for C$_{23}$H$_{28}$N$_2$O$_2$-0.29 (CHCl$_3$): C, 70.02; H, 7.14; N, 7.01. Found: C, 70.02; H, 7.37; N, 6.84.

(S)-quinuclidin-3-yl 2-(biphenyl-4-yl)propan-2-yl-carbamate (Compound 5)

Using General Procedure B, bromobenzonitrile (2.00 g, 11.0 mmol) was converted to the corresponding 2-(4-bromophenyl)propan-2-amine (1.20 g, 51%) as a brown oil.

Using General Procedure A, 2-(4-bromophenyl)propan-2-amine (1.0 g, 4.7 mmol) and (S)-quinuclidin-3-ol gave (S)-quinuclidin-3-yl 2-(4-bromophenyl)propan-2-ylcarbamate (1.0 g, 58%) as a brown oil.

Using General Procedure C, the above bromide (200 mg, 0.540 mmol), phenylboronic acid (133 mg, 1.10 mmol), and [PdCl$_2$(pddf)]CH$_2$Cl$_2$ gave the title compound as a white solid (70 mg, 35%). $^1$H NMR (500 MHz, CDCl$_3$) δ 7.60-7.53 (m, 4H), 7.47 (d, J=8.5 Hz, 2H), 7.42 (t, J=7.5 Hz, 2H), 7.33 (t, J=7.5 Hz, 1H), 5.26 (br s, 1H), 4.64 (m, 1H), 3.33-3.15 (m, 1H), 3.10-2.45 (m, 5H), 2.40-1.80 (m, 2H), 1.78-1.58 (m, 7H), 1.55-1.33 (m, 2H) ppm. $^{13}$C NMR (125 MHz, CDCl$_3$) δ 154.5, 146.1, 140.8, 139.5, 128.7, 127.2, 127.1, 127.1, 125.2, 70.9, 55.5, 55.1, 47.4, 46.4, 31.1, 29.5, 25.3, 24.5, 19.5 ppm. Purity: 100% LCMS (214 nm & 254 nm); retention time 1.56 min; (M+1) 365.

Quinuclidin-3-yl 1-(biphenyl-4-yl)cyclopropylcarbamate (Compound 6)

Using General Procedure D, bromobenzonitrile (3.00 g, 16.5 mmol) was converted to the corresponding 1-(4-bromophenyl)cyclopropanamine (1.80 g, 51%) as a yellow solid.

Using General Procedure A, 1-(4-bromophenyl)cyclopropanamine (1.0 g, 4.7 mmol) and quinuclidin-3-ol gave quinuclidin-3-yl 1-(4-bromophenyl)cyclopropyl-carbamate (1.3 g, 75%) as a white semi-solid.

Using General Procedure C, the above carbamate (400 mg, 1.12 mmol), phenylboronic acid (267 mg, 2.22 mmol), and [PdCl$_2$ (pddf)]CH$_2$Cl$_2$ the title compound as a viscous oil (100 mg, 25%). $^1$H NMR (500 MHz, CDCl$_3$) δ 7.47 (d, J=7.5 Hz, 2H), 7.43 (d, J=8.0 Hz, 2H), 7.33 (t, J=7.5 Hz, 2H), 7.26-7.15 (m, 3H), 5.93 (br s, 0.6H), 5.89 (br s, 0.4H), 4.67 (m, 1H), 3.20-3.06 (m, 1H), 2.88-2.42 (m, 5H), 1.98-1.08 (m, 9H) ppm. $^{13}$C NMR (125 MHz, CDCl$_3$) δ 155.0, 141.0, 139.7, 138.2, 127.7, 126.1, 126.0, 124.8, 124.1, 70.0, 54.5, 46.3, 45.4, 34.1, 24.3, 23.2, 18.3, 17.0 ppm. Purity: 100% LCMC (214 nm & 254 nm); retention time 1.52 min; (M+1) 363.

(S)-quinuclidin-3-yl 1-(4'-fluorobiphenyl-4-yl)cyclopropylcarbamate (Compound 7)

Using General Procedure C, (S)-quinuclidin-3-yl 1-(4-bromophenyl)cyclopropyl carbamate, 4-F-phenylboronic acid, and [PdCl$_2$ (pddf)]CH$_2$Cl$_2$ gave the title compound as a white solid (45%). $^1$H NMR (500 MHz, DMSO-d6) δ 8.06-7.83 (d, 1H), 7.69-7.66 (m, 2H), 7.59-7.55 (m, 2H), 7.29-7.22 (m, 4H), 4.56-4.54 (m, 1H), 3.13-2.32 (m, 6H), 1.91-1.19 (m, 9H) ppm. 13C NMR (125 MHz, DMSO-d6) δ 163.2, 161.2, 156.4, 143.7, 136.9, 128.9, 128.8, 126.8, 125.6, 116.2, 116.0, 70.7, 55.8, 47.4, 46.4, 34.8, 25.7, 24.6, 19.6, 18.7, 18.6 ppm. Purity: >97% LCMS (214 nm & 254 nm); retention time 1.96 min; (M+1) 381.2.

(S)-1-azabicyclo[2.2.2]oct-3-yl [1-(2',4'-difluorobiphenyl-4-yl)cyclopropyl]carbamate (Compound 8)

Using General Procedure C, (S)-quinuclidin-3-yl 1-(4-bromophenyl)cyclopropylcarbamate (0.446 g, 1.22 mmol), 2,4-difluorophenyl boronic acid (0.386 g, 2.44 mmol) and Pd(OAc)$_2$ (0.015 g, 0.067 mmol) gave the title compound as a tan solid (0.111 g, 23%). $^1$H NMR (CDCl$_3$) δ 7.43 (dd, J=8.4, 1.6 Hz, 2H), 7.40-7.33 (m, 1H), 7.31 (d, J=7.7 Hz, 2H), 6.99-6.81 (m, 2H), 5.54 (d, J=48.0 Hz, 1H), 4.82-4.65 (m, 1H), 3.30-3.07 (m, 1H), 2.98-2.44 (m, 5H), 1.97 (d, J=32.7 Hz, 1H), 1.83 (d, J=10.3 Hz, 1H), 1.64 (s, 1H), 1.52 (s, 1H), 1.39 (s, 1H), 1.31 (d, J=6.8 Hz, 4H) ppm. $^{13}$C NMR major rotomer (CDCl$_3$) δ 162.2 (dd, J=12.8, 249.1 Hz), 159.8 (dd, J=11.8, 251.0 Hz), 156.9, 156.0, 142.6, 133.1, 131.3 (m), 128.9, 125.6, 124.9, 111.5 (dd, J=3.9, 21.2 Hz) 104.4 (dd, J=25.2, 29.4 Hz), 72.1, 71.6, 55.7, 47.4, 46.5, 35.7, 35.3, 25.5, 24.6, 24.4, 19.5, 18.1 ppm. Purity: LCMS >99.3% (214 nm & 254 nm); retention time 0.90 min; (M+1) 399.0.

1-azabicyclo[2.2.2]oct-3-yl [1-(4'-methoxybiphenyl-4-yl)cyclopropyl]carbamate (Compound 9)

Using General Procedure C, quinuclidin-3-yl 1-(4-bromophenyl)cyclopropylcarbamate (0.485 g, 1.33 mmol), 4-methoxyphenyl boronic acid (0.404 g, 2.66 mmol), and Pd(OAc)$_2$ (0.016 g, 0.071 mmol) gave the title compound as a grey solid (0.337 mg, 65%). $^1$H NMR (CDCl$_3$) δ 7.48 (dd, J=8.6, 5.5 Hz, 4H), 7.29 (d, J=7.6 Hz, 2H), 6.96 (d, J=8.8 Hz, 2H), 5.58 (d, J=48.7 Hz, 1H), 4.83-4.63 (m, 1H), 3.84 (s, 3H), 3.20 (dd, J=24.0, 15.5 Hz, 1H), 2.97-2.42 (m, 5H), 1.97 (d, J=30.9 Hz, 1H), 1.81 (s, 1H), 1.75-1.33 (m, 3H), 1.28 (d, J=6.8 Hz, 4H) ppm. $^{13}$C NMR major rotomer (CDCl$_3$) δ 159.1, 156.0, 141.4, 139.0, 133.4, 128.0, 126.7, 125.9, 114.2, 71.5, 55.7, 55.3, 47.4, 46.5, 35.3, 25.5, 24.6, 19.6, 17.8 ppm. Purity: LCMS >97.1% (214 nm & 254 nm); retention time 0.88 min; (M+1) 393.4.

Quinuclidin-3-yl 2-(5-(4-fluorophenyl)thiophen-3-yl)propan-2-ylcarbamate (Compound 10)

To a stirred and cooled (0° C.) solution of ethyl 5-bromothiophene-3-carboxylate (13.30 g, 56.57 mmol) in THF (100 mL) was added a solution of methylmagnesium bromide in diethyl ether [3.0 M] (55.0 mL, 165 mmol), dropwise over 20 minutes. After 2 hours, the reaction solution was concentrated. The residue was taken up in aqueous NH$_4$C$_1$ (200 mL) and extracted with ethyl acetate (2×100 mL). The combined extracts were dried (Na$_2$SO$_4$) and concentrated. The resulting amber oil was purified by flash chromatography using a hexane/ethyl acetate gradient to afford 2-(5-bromothiophen-3-yl)propan-2-ol as a pale amber oil (8.05 g, 64%).

To a stirred solution of 2-(5-bromothiophen-3-yl)propan-2-ol (8.03 g, 36.3 mmol) in methylene chloride (80 mL) was added sodium azide (7.08 g, 109 mmol) followed by trifluoroacetic acid (8.0 mL; dropwise over 5-6 minutes). The thickening suspension was stirred for 1.5 hour before diluting with water (350 mL) and extracting with ethyl acetate (1×200 mL). The organic layer was washed with aqueous NaHCO$_3$ (1×250 mL), dried (Na$_2$SO$_4$), and concentrated to afford the crude azide product. To a stirred solution of this material in THF (160 mL) was added water (11 mL) followed by triphenylphosphine (23.8 g, 90.7 mmol). The reaction was stirred for 2 days before concentrating. The resulting residue was dissolved in ethyl acetate (250 mL) and extracted with 1 N aqueous HCl (4×75 mL). The combined extracts were basified with concentrated NH$_{40}$H and extracted with ethyl acetate (2×100 mL). These extracts were, in turn, dried (Na$_2$SO$_4$), and concentrated. The resulting amber oil was purified by flash chromatography using a methylene chloride/methanol/ammonia gradient to afford a mixture of 2-(5-bromothiophen-3-yl)propan-2-amine and triphenylphosphine oxide (~70/30 ratio) as a viscous amber oil (1.32 g, 17%).

To a stirred solution of 3-quinuclidinol (3.00 g, 23.6 mmol) in THF (100 mL) was added 4-nitrophenyl chloroformate (5.94 g, 29.5). After stirring for 4 hours, the precipitate was filtered off, rinsed with THF, and air dried on the frit under house vacuum. The filter cake was dissolved in ethyl acetate (150 mL) and washed with aqueous NaHCO$_3$ (1×150 mL) and water (2×150 mL). The organic layer was dried (Na$_2$SO$_4$) and concentrated to afford crude 4-nitrophenyl quinuclidin-3-yl carbonate product, which was used in the next step without purification.

To a stirred solution of 2-(5-bromothiophen-3-yl)propan-2-amine (0.366 g, 1.66 mmol) in THF (10 mL) was added 4-nitrophenyl quinuclidin-3-yl carbonate (0.571 g, 1.95 mmol) and a few granules of 4-(dimethylamino)pyridine. The mixture was refluxed overnight, concentrated, and partitioned between ethyl acetate (50 mL) and aqueous NaHCO$_3$ (50 mL). The organic layer was washed again with aqueous NaHCO₃ (1×50 mL), dried (Na₂SO₄), and concentrated. The resulting dirty yellow gum was purified by flash chromatography using a chloroform/methanol/ammonia gradient to afford quinuclidin-3-yl (1-(5-bromothiophen-3-yl)cyclopropyl)carbamate as an off-white solid (0.305 g, 49%).

Using General Procedure C, quinuclidin-3-yl (1-(5-bromothiophen-3-yl)cyclopropyl)carbamate (0.227 g, 0.742 mmol), 4-fluorophenyl boronic acid (0.208 g, 1.49 mmol), tricyclohexylphosphine (0.021 g, 0.075 mmol), potassium phosphate (0.866, 4.08 mmol), and palladium acetate (8.0 mg, 36 μmol) gave the title compound as a grey solid (0.142 g, 49%). $^1$H NMR (400 MHz, CDCl₃) δ 7.60-7.45 (m, 2H), 7.24-7.19 (m, 1H), 7.10-6.97 (m, 3H), 5.23 (br s, 1H), 4.72-4.61 (m, 1H), 3.30-3.04 (m, 1H), 3.03-2.25 (m, 5H), 2.09-1.02 (m, 11H) ppm. $^{13}$C NMR (400 MHz, CDCl₃) δ 162.3 (d, J=247.1 Hz), 154.5, 149.8, 143.6, 130.7, 127.4 (d, J=8.1 Hz), 121.8, 118.9, 115.8 (d, J=21.6 Hz), 70.8, 55.5, 53.4, 47.3, 46.4, 29.0, 25.4, 24.4, 19.4 ppm. Purity: 95.8% UPLCMS (210 nm & 254 nm); retention time 0.90 min; (M+1) 389.

(S)-quinuclidin-3-yl 2-(3-(4-fluorophenyl)isothiazol-5-yl)propan-2-ylcarbamate (Compound 11)

To stirred solution of 2-(3-(4-fluorophenyl)isothiazol-5-yl)propan-2-amine (1.21 g, 5.12 mmol) in toluene was added a solution of phosgene in toluene [~1.9 M] (10.8 mL, 20.5 mmol). The reaction was heated at reflux for two hours and then concentrated. The residue was co-evaporated with toluene (2×15 mL) to afford the crude isocyanate intermediate as golden oil. This material was taken up in toluene (10 mL) and treated with (S)-3-quinuclidinol (0.749 g, 5.89 mmol). The reaction was heated at reflux overnight and concentrated. The residue was purified by flash chromatography using a chloroform/methanol/ammonia gradient to afford the title compound as a white solid (0.971 g, 49%). $^1$H NMR (400 MHz, DMSO-d6) δ 8.09-8.00 (m, 2H), 7.87 (br s, 1H), 7.75 (s, 1H), 7.35-7.25 (m, 2H), 4.54-4.45 (m, 1H), 3.14-2.92 (m, 1H), 2.87-2.17 (m, 5H), 1.98-0.98 (m, 11H) ppm. $^{13}$C NMR (400 MHz, DMSO-d6) δ 180.1, 165.6, 162.6 (d, J=246.4 Hz), 154.7, 131.2 (d, J=3.0 Hz), 128.7 (d, J=8.4 Hz), 118.2, 115.7 (d, J=21.8 Hz), 70.6, 55.3, 52.8, 46.9, 45.9, 29.9, 25.2, 24.2, 19.2 ppm. Purity: 100% UPLCMS (210 nm & 254 nm); retention time 0.82 min; (M+1) 390.

(S)-quinuclidin-3-yl 2-(4-(4-fluorophenyl)thiazol-2-yl)propan-2-ylcarbamate (Compound To a stirred solution of ethyl 3-amino-3-thioxopropanoate (20.00 g, 135.9 mmol) in ethanol (120 mL) was added 2-bromo-4'-fluoroacetophenone (29.49 g, 135.9 mmol). The mixture was refluxed for 1 hour, concentrated, and partitioned between ethyl acetate (300 mL) and aqueous NaHCO₃ (400 mL). The organic layer was combined with a back-extract of the aqueous layer (ethyl acetate, 1×100 mL), dried (Na₂SO₄), and concentrated. The resulting light brown solid was purified by flash chromatography using a hexane/ethyl acetate gradient to afford ethyl 2-(4-(4-fluorophenyl)thiazol-2-yl)acetate as an off-white solid (29.92 g, 83%).

To a stirred and cooled (−78° C.) solution of ethyl 2-(4-(4-fluorophenyl)thiazol-2-yl)acetate (10.00 g, 37.69 mmol) in THF (250 mL) was added a solution of potassium t-butoxide in THF [1.0 M] (136 mL, 136 mmol), dropwise over 15 minutes, followed by 18-crown-6 (1.6 mL, 7.5 mmol). After an additional 30 minutes at −78° C., iodomethane (8.5 mL) was added, dropwise over 5 minutes. The reaction was stirred cold for another 2 hours before pouring into water (450 mL) and extracting with ethyl acetate (2×150 mL). The combined extracts were washed with brine (1×200 mL), dried (Na₂SO₄), and concentrated. The resulting brown oil was purified by flash chromatography using a hexane/ethyl acetate gradient to afford ethyl 2-(4-(4-fluorophenyl)thiazol-2-yl)-2-methylpropanoate as a pale amber oil (8.64 g, 78%).

To a stirred solution of ethyl 2-(4-(4-fluorophenyl)thiazol-2-yl)-2-methylpropanoate (0.900 g, 3.07 mmol) in 1:1:1 THF/ethanol/water (15 mL) was added lithium hydroxide monohydrate (0.451 g, 10.7 mmol). After overnight stirring, the reaction was concentrated and redissolved in water (80 mL). The solution was washed with ether (1×50 mL), acidified with the addition of 1N HCl (15 mL), and extracted with ethyl acetate (2×50 mL). The combined extracts were dried (Na₂SO₄) and concentrated to afford 2-(4-(4-fluorophenyl)thiazol-2-yl)-2-methylpropanoic acid as a pale golden solid (0.808 g, 99%).

To stirred and cooled (0° C.) solution of 2-(4-(4-fluorophenyl)thiazol-2-yl)-2-methylpropanoic acid (0.784 g, 2.96 mmol) in THF (25 mL) was added triethylamine (0.82 mL, 5.9 mmol) followed by isobutyl chloroformate (0.58 mL, 4.4 mmol). The reaction was stirred cold for another 1 hour before adding a solution of sodium azide (0.385 g, 5.92 mmol) in water (7 mL). The reaction was stirred overnight, allowing the cooling bath to slowly warm to room temperature. The mixture was then diluted with water (100 mL) and extracted with ethyl acetate (2×60 mL). The combined extracts were washed with aqueous NaHCO₃ (1×150 mL) and brine (1×100 mL), dried (Na₂SO₄), and concentrated. After coevaporating with toluene (2×30 mL), the resulting off-white solid was taken up in toluene (25 mL) and refluxed for 4 hours. (S)-3-quinuclidinol (0.753 g, 5.92 mmol) was then added and reflux was continued for 3 hours. The reaction was concentrated and the residue was purified by flash chromatography using a chloroform/methanol/ammonia gradient to afford the title compound as a white solid (0.793 g, 69%). $^1$H NMR (400 MHz, CDCl₃) δ 7.90-7.81 (m, 2H), 7.32 (s, 1H), 7.14-7.05 (m, 2H), 5.76 (br s, 1H), 4.72-4.65 (m, 1H), 3.26-3.10 (m, 1H), 3.03-2.37 (m, 5H), 2.05-1.23 (m, 11H) ppm. $^{13}$C NMR (400 MHz, CDCl₃) δ 177.6, 162.6 (d, J=248.4 Hz), 154.8, 153.6, 130.8 (d, J=3.2 Hz), 128.1 (d, J=8.1 Hz), 115.9 (d, J=21.7 Hz), 112.2, 71.6, 55.7, 47.4, 46.5, 29.1, 25.4, 24.7, 19.6 ppm. Purity: 100% UPLCMS (210 nm & 254 nm); retention time 0.82 min; (M+1) 390.

Quinuclidin-3-yl (2-(4'-(2-methoxyethoxy)-[1,1'-biphenyl]-4-yl)propan-2-yl)carbamate (Compound 13)

Using General Procedure F and the reaction inputs 2-(4'-(2-methoxyethoxy)-[1,1'-biphenyl]-4-yl)-2-methylpropanoic acid (prepared as described in Example 3) and quinuclidin-3-ol, the title compound was generated as a colourless, glassy solid (23%). NMR data matched that of Example 3. Purity: 100%, 99.1% (210 & 254 nm) UPLCMS; retention time: 0.87 min; (M+H⁺) 439.0.

(S)-quinuclidin-3-yl (2-(3'-(2-methoxyethoxy)-[1,1'-biphenyl]-4-yl)propan-2-yl)carbamate (Compound 14)

Exchanging 4-(2-methoxyethoxy)phenylboronic acid for 3-(2-methoxyethoxy)phenylboronic acid, the reaction sequence outlined in Example 3 was used to prepare 2-(3'-

(2-methoxyethoxy)-[1,1'-biphenyl]-4-yl)-2-methylpropanoic acid. This intermediate and quinuclidin-3-ol were reacted according to General Procedure F to generate the title compound as a glassy, colourless solid. $^1$H NMR (400 MHz, DMSO-d6) δ 7.63-7.31 (m, 6H), 7.24-7.10 (m, 2H), 6.92 (dd, J=8.2, 1.9 Hz, 1H), 4.51-4.34 (m, 1H), 4.21-4.08 (m, 2H), 3.72-3.64 (m, 2H), 3.32 (s, 3H), 3.09-2.26 (m, 5H), 2.04-1.22 (m, 9H) ppm. $^{13}$C NMR (100 MHz, DMSO-d6) δ 158.6, 154.6, 147.6, 141.5, 137.6, 129.9, 126.3, 125.2, 118.9, 113.2, 112.5, 70.4, 70.0, 66.9, 58.2, 55.4, 54.2, 46.9, 45.9, 29.4, 25.3, 24.2, 19.2 ppm. Purity: 100%, 100% (210 & 254 nm) UPLCMS; retention time: 0.91 min; 15 (M+H+) 439.4.

Quinuclidin-3-yl (2-(4'-(2-methoxyethoxy)-[1,1'-biphenyl]-3-yl)propan-2-yl)carbamate (Compound 15)

Exchanging ethyl 2-(4-bromophenyl)-2-methylpropanoate for ethyl 2-(3-bromophenyl)-2-methylpropanoate, the reaction sequence outlined in Example 3 was used to prepare 2-(4'-(2-methoxyethoxy)-[1,1'-biphenyl]-3-yl)-2-methylpropanoic acid. This intermediate and quinuclidin-3-ol were reacted according to General Procedure F to generate the title compound as a yellow solid. $^1$H NMR (400 MHz, DMSO-d6) δ 7.62-7.20 (m, 7H), 7.03 (d, J=8.7 Hz, 2H), 4.48-4.35 (m, 2H), 4.18-4.08 (m, 2H), 3.72-3.62 (m, 2H), 3.32 (s, 3H), 3.10-2.19 (m, 6H), 2.10-1.10 (m, 11H) ppm. $^{13}$C NMR (100 MHz, DMSO-d6) δ 158.0, 154.6, 148.8, 139.5, 133.1, 128.5, 127.7, 123.8, 123.2, 122.7, 114.8, 70.4, 69.9, 67.0, 58.2, 55.3, 54.5, 47.0, 45.9, 29.4, 25.3, 24.2, 19.2 ppm. Purity: 97.4%, 94.6% (210 & 254 nm) UPLCMS; retention time: 0.88 min; (M+H+) 439.3.

Quinuclidin-3-yl (2-(4'-(3-methoxypropoxy)-[1,1'-biphenyl]-4-yl)propan-2-yl)carbamate (Compound 16)

To a stirred solution of 4-iodophenol (10.05 g, 45.68 mmol) in acetonitrile (100 mL) was added potassium carbonate (6.95 g, 50.2 mmol) and 1-chloro-3-methoxypropane (6.4 mL, 57.1 mmol). The mixture was heated at reflux overnight and then concentrated. The residue was taken up in water and extracted with ethyl acetate. The combined extracts were washed with aqueous sodium bicarbonate solution, dried (Na$_2$SO$_4$). and concentrated. The crude material was purified by flash chromatography over silica using a hexane/ethyl acetate eluent to afford 1-iodo-4-(3-methoxypropoxy)benzene as a colourless oil (4.39 g, 33%). This intermediate and ethyl 2-methyl-2-(4-(4,4,5,5-tetramethyl-1,3,2-dioxaborolan-2-yl)phenyl)propanoate were reacted according to General Procedure E to generate ethyl 2-(4'-(3-methoxypropoxy)-[1,1'-biphenyl]-4-yl)-2-methylpropanoate. To a stirred solution of this compound (0.693 g, 1.94 mmol) in 1:1:1 (v/v/v) tetrahydrofuran/ethanol/water (10 mL) was added lithium hydroxide monohydrate (0.326 g, 7.77 mmol). The mixture was heated at reflux overnight and then concentrated. The residue was dissolved in water, treated with 1N hydrochloric acid (10 mL), and extracted with ethyl acetate. The combined organic layers were washed with brine, dried (Na$_2$SO$_4$), and concentrated to afford 2-(4'-(3-methoxypropoxy)-[1,1'-biphenyl]-4-yl)-2-methylpropanoic acid as a waxy, off-white solid (0.630 g, 99%). This intermediate and quinuclidin-3-ol were reacted according to General Procedure F to generate the title compound as a glassy, colourless solid (62%). $^1$H NMR (400 MHz, DMSO-d6) δ 7.61-7.29 (m, 7H), 7.00 (d, J=8.8 Hz, 2H), 4.47-4.36 (m, 1H), 4.05 (t, J=6.4 Hz, 2H), 3.48 (t, J=6.3 Hz, 2H), 3.26 (s, 3H), 3.10-2.25 (m, 6H), 2.04-1.74 (m, 4H), 1.65-1.23 (m, 9H) ppm. $^{13}$C NMR (100 MHz, DMSO-d6) δ 158.0, 154.5, 146.7, 137.4, 132.4, 127.5, 125.7, 125.2, 114.8, 69.9, 68.5, 64.6, 57.9, 55.4, 54.2, 46.9, 46.0, 29.4, 29.0, 25.2, 24.1, 19.2 ppm. Purity: 97.7%, 98.2% (210 & 254 nm) UPLCMS; retention time: 0.96 min; (M+H+) 453.5.

Quinuclidin-3-yl (2-(4'-(hydroxymethyl)-[1,1'-biphenyl]-4-yl)propan-2-yl)carbamate (Compound 17)

Using General Procedure E and the reaction inputs ethyl 2-(4-bromophenyl)-2-methylpropanoate and 4-formylphenylboronic acid, ethyl 2-(4'-formyl-[1,1'-biphenyl]-4-yl)-2-methylpropanoate was prepared as a pale amber solid. This intermediate and quinuclidin-3-ol were reacted according to General Procedure F to generate quinuclidin-3-yl (2-(4'-formyl-[1,1'-biphenyl]-4-yl)propan-2-yl)carbamate as foamy, yellow solid. To a stirred solution of this material (0.755 g, 1.92 mmol) in 2:1 (v/v) tetrahydrofuran/ethanol (15 mL) was added sodium borohydride (0.073 g, 1.93 mmol). After 45 minutes, the reaction was diluted with water and extracted with chloroform. The combined extracts were dried (Na$_2$SO$_4$) and concentrated onto silica. Flash chromatography over silica using a chloroform/methanol/ammonia eluent provided the title compound as a white solid (0.323 g, 43%). $^1$H NMR (400 MHz, DMSO-d6) δ 7.66-7.29 (m, 9H), 5.18 (t, J=5.7 Hz, 1H), 4.53 (d, J=5.7 Hz, 2H), 4.46-4.37 (m, 1H), 3.11-2.19 (m, 6H), 2.11-1.10 (m, 11H) ppm. $^{13}$C NMR (100 MHz, DMSO-d6) δ 154.7, 147.3, 141.5, 138.4, 137.7, 127.0, 126.2, 126.1, 125.3, 70.0, 62.6, 55.4, 54.2, 46.9, 45.9, 29.4, 25.3, 24.2, 19.2 ppm. Purity: 97.5%, 99.1% (210 & 254 nm) UPLCMS; retention time: 0.73 min; (M+H+) 395.

Quinuclidin-3-yl (2-(4'-(2-hydroxyethyl)-[1,1'-biphenyl]-4-yl)propan-2-yl)carbamate (Compound 18)

Using General Procedure E and the reaction inputs 1-(2-(benzyloxy)ethyl)-4-bromobenzene and ethyl 2-methyl-2-(4-(4,4,5,5-tetramethyl-1,3,2-dioxaborolan-2-yl)phenyl) propanoate, ethyl 2-(4'-(2-(benzyloxy)ethyl)-[1,1'-biphenyl]-4-yl)-2-methylpropanoate was prepared as a colourless gum. To a stirred solution of this compound (1.34 g, 3.33 mmol) in 1:1:1 (v/v/v) tetrahydrofuran/ethanol/water (18 mL) was added lithium hydroxide monohydrate (0.698 g, 16.6 mmol). After heating at reflux overnight, the reaction was concentrated and partitioned between water and diethyl ether. The resulting emulsion was extracted repeatedly with 0.2 N aqueous sodium hydroxide solution (5×50 mL). The clear portion of the aqueous layer was removed each time. The combined aqueous layers were then treated with 1.0 N hydrochloric acid (80 mL) and the resulting suspension of white solid was extracted with ethyl acetate. The combined organic layers were dried (Na$_2$SO$_4$) and concentrated to afford 2-(4'-(2-(benzyloxy)ethyl)-[1,1'-biphenyl]-4-yl)-2-methylpropanoic acid as a white solid (1.20 g, 96%). This compound and quinuclidin-3-ol were reacted according to General Procedure F to generate quinuclidin-3-yl (2-(4'-(2-benzyloxyethyl)-[1,1'-biphenyl]-4-yl)propan-2-yl)carbamate. To a stirred solution of this material (0.435 g, 0.806 mmol) in methanol was added 1.0 N hydrochloric acid (1 mL) and 10% palladium on carbon (50% water; 0.087 g). The mixture was cycled between vacuum and a nitrogen purge several times, refilling with hydrogen after the last evacuation. After 1.25 hours the reaction was filtered through Celite and concentrated. The residue was taken up in aqueous sodium carbonate solution and extracted with 4:1 (v/v) chloroform/isopropanol. The combined extracts were dried (Na$_2$SO$_4$) and concentrated onto silica. Flash chromatography over silica using a chloroform/methanol/ammonia gradient provided the purified title compound as a colourless solid. $^1$H NMR (400 MHz, DMSO-d6) δ 7.85-7.63 (m, 1H), 7.63-7.19 (m, 8H), 4.78-4.62 (m, 2H), 3.71-2.78 (m, 8H), 2.76 (t, J=6.8 Hz, 2H), 2.26-1.96 (m, 2H), 1.96-1.40 (m, 9H) ppm. $^{13}$C NMR (100 MHz, DMSO-d6) δ 153.8, 146.8, 138.7, 137.9, 137.6, 129.4, 126.3, 126.1, 125.3, 66.2, 62.1, 54.4, 52.8, 45.4, 44.5, 38.6, 29.5, 29.2, 24.0, 19.9, 16.6 ppm. Purity: 100%, 100% (210 & 254 nm) UPLCMS; retention time: 0.75 min; (M+H+) 409.

Quinuclidin-3-yl (2-(2-(4-(3-methoxypropoxy)phenyl)thiazol-4-yl)propan-2-yl)carbamate (Compound 19)

To a stirred suspension of 4-methoxythiobenzamide (9.99 g, 59.7 mmol) in ethanol (75 mL) was added ethyl 4-chloroacetoacetate (8.1 mL, 60 mmol). The mixture was heated at reflux for 4 hours before cooling, adding additional ethyl 4-chloroacetoacetate (0.81 mL, 6.0 mmol), and returning to reflux. After 4 more hours of heating the reaction was concentrated and partitioned between ethyl acetate and aqueous sodium bicarbonate solution. The organic layer was combined with additional ethyl acetate extracts, dried (Na$_2$SO$_4$), and concentrated. The crude product was purified by flash chromatography over silica using a hexane/ethyl acetate gradient to afford ethyl 2-(2-(4-methoxyphenyl)thiazol-4-yl)acetate as a pale amber oil (14.51 g, 87%). To a stirred solution of this compound (14.48 g, 52.2 mmol) in N,N-dimethylformamide (125 mL) was added sodium hydride (60% dispersion in mineral oil; 6.27 g, 157 mmol), portion wise over 15 minutes. The resulting red suspension was cooled (0° C.) and treated, dropwise over 10 minutes, with iodomethane (9.80 mL, 157 mmol). The cooling bath was removed and the reaction was allowed to stir 4 hours before concentrating and partitioning the residue between ethyl acetate and water. The organic layer was washed twice more with water, dried (Na$_2$SO$_4$), and concentrated. The residue was purified by flash chromatography over silica using a hexane/ethyl acetate gradient to afford ethyl 2-(2-(4-methoxyphenyl)thiazol-4-yl)-2-methylpropanoate as a pale amber oil (14.12 g, 89%). To a stirred solution of this intermediate (14.12 g, 46.24 mmol) in methylene chloride (250 mL) was added boron tribromide (11.0 mL, 116 mmol), dropwise over 5 minutes. After stirring overnight, the reaction was quenched by the slow addition of methanol (~20 mL) and then concentrated. The residue was taken up in methanol (250 mL) and concentrated sulfuric acid (7.0 mL). The stirred solution was heated at reflux for 2 hours, concentrated, and partitioned between ethyl acetate and aqueous sodium bicarbonate solution. The organic layer was combined with a second ethyl acetate extract of the aqueous layer, dried (Na$_2$SO$_4$), and concentrated to afford methyl 2-(2-(4-hydroxyphenyl)thiazol-4-yl)-2-methylpropanoate as a white solid (12.56 g, 98%). To a stirred solution of 1-bromo-3-methoxypropane (1.66 g, 10.8 mmol) in acetone (30 mL) was added the phenol intermediate (2.00 g, 7.21 mmol) and potassium carbonate (1.25 g, 9.04 mmol). The mixture was heated overnight at reflux, filtered, and concentrated. The residue was purified by flash chromatography over silica using a hexane/ethyl acetate gradient to afford methyl 2-(2-(4-(3-methoxypropoxy)phenyl)thiazol-4-yl)-2-methylpropanoate as a faint amber gum (2.47 g, 98%). To a stirred solution of this compound (2.45 g, 7.01 mmol) in 1:1:1 (v/v/v) tetrahydrofuran/ethanol/water (45 mL) was added lithium hydroxide monohydrate (1.47 g, 35.0 mmol). After overnight stirring, the reaction was concentrated and partitioned between water and diethyl ether. The aqueous layer was treated with 1.0 N hydrochloric acid (40 mL) and extracted with ethyl acetate. The combined extracts were dried (Na$_2$SO$_4$) and concentrated to afford 2-(2-(4-(3-methoxypropoxy)phenyl)thiazol-4-yl)-2-methylpropanoic acid as a white solid (2.19 g, 40 93%). This compound and quinuclidin-3-ol were reacted according to General Procedure F to generate the title compound as a soft, faint amber solid. $^1$H NMR (400 MHz, DMSO-d6) δ 7.82 (d, J=8.9 Hz, 2H), 7.36 (br s, 1H), 7.24 (br s, 1H), 7.03 (d, J=8.9 Hz, 2H), 4.49-4.41 (m, 1H), 4.07 (t, J=6.4 Hz, 2H), 3.48 (t, J=6.4 Hz, 2H), 3.26 (s, 3H), 3.09-2.26 (m, 6H), 2.02-1.91 (m, 2H), 1.91-1.03 (m, 11H) ppm. $^{13}$C NMR (100 MHz, DMSO-d6) δ 165.8, 162.4, 160.0, 154.6, 127.5, 126.1, 114.9, 112.1, 70.1, 68.4, 64.8, 57.9, 55.4, 53.5, 46.9, 45.9, 28.9, 28.3, 25.2, 24.2, 19.2 ppm. Purity: 100%, 100% (210 & 254 nm) UPLCMS; retention time: 0.87 min; (M+H+) 460.

Quinuclidin-3-yl (2-(2-(4-(2-methoxyethoxy)phenyl)thiazol-4-yl)propan-2-yl)carbamate (Compound 20)

To a stirred solution of 2-bromoethyl methyl ether (1.88 g, 13.5 mmol) in acetone was added methyl 2-(2-(4-hydroxyphenyl)thiazol-4-yl)-2-methylpropanoate (prepared as described in Example 19, 2.00 g, 7.21 mmol) and potassium carbonate (1.56 g, 11.3 mmol). After heating at reflux overnight, the mixture was treated with additional 2-bromo ethyl methyl ether (1.88 g, 13.5 mmol) and potassium carbonate (1.56 g, 11.3 mmol). The reaction was heated at reflux for a second night, filtered, and concentrated. The residue was purified by flash chromatography over silica using a hexane/ethyl acetate gradient to afford methyl 2-(2-(4-(2-methoxyethoxy)phenyl)thiazol-4-yl)-2-methylpropanoate as a white solid (2.71 g, 90%). To a stirred solution of this compound (2.71 g, 8.08 mmol) in 1:1:1 (v/v/v) tetrahydrofuran/ethanol/water (50 mL) was added lithium hydroxide monohydrate (1.70 g, 40.5 mmol). After overnight stirring, the reaction was concentrated and partitioned between water and diethyl ether. The aqueous layer was treated with 1.0 N hydrochloric acid (41 mL) and extracted with ethyl acetate. The combined extracts were dried (Na$_2$SO$_4$) and concentrated to afford 2-(2-(4-(2-methoxyethoxy)phenyl)thiazol-4-yl)-2-methylpropanoic acid as a white solid (2.57 g, 99%). This compound and quinuclidin-3-ol were reacted according to General Procedure F to generate the title compound as a pale amber solid. $^1$H NMR (400 MHz, DMSO-d6) δ 7.82 (d, J=8.8 Hz, 2H), 7.36 (br s, 1H), 7.24 (br s, 1H), 7.04 (d, J=8.8 Hz, 2H), 4.49-4.41 (m, 1H), 4.19-4.12 (m, 2H), 3.71-3.65 (m, 2H), 3.32 (s, 3H), 3.11-2.87 (m, 1H), 2.86-2.19 (m, 5H), 1.92-1.16 (m, 11H) ppm. $^{13}$C NMR (100 MHz, DMSO-d6) δ 165.7, 162.9, 159.9, 154.6, 127.5, 126.2, 114.9, 112.2, 70.3, 70.1, 67.1, 58.2, 55.4, 53.5, 46.9, 45.9, 28.3, 25.2, 24.3, 19.2 ppm. Purity: 100%, 100% (210 & 254 nm) UPLCMS; retention time: 0.85 min; (M+H+) 446.

Quinuclidin-3-yl 2-(5-(4-(2-methoxyethoxy)phenyl)pyridin-2-yl)propan-2-ylcarbamate (Compound 21)

Using General Procedure E and the reaction inputs 5-bromopicolinonitrile and 2-(4-(2-methoxyethoxy)phenyl)-4,4,5,5-tetramethyl-1,3,2-dioxaborolane, 5-(4-(2-methoxyethoxy)phenyl)picolinonitrile was prepared. Cerium trichloride (8.05 g, 21.6 mmol) was loaded into a flask and dried by heating (170° C.) under vacuum for 3 hours. The solid was taken up in tetrahydrofuran (20 mL) and stirred vigorously for 30 minutes. The suspension was cooled to −78° C. and treated, dropwise, with a 3.0 M solution of methyllithium in diethyl ether (7.2 mL, 21.6 mmol). Following addition, the reaction was stirred at −78° C. for 1 hour before adding a solution of the above aryl borate (1.83 g, 7.20 mmol) in tetrahydrofuran (20 mL). The mixture was maintained at −78° C. for 2 hours and then allowed to warm to room temperature. At this time, the reaction was quenched by the addition of aqueous ammonium hydroxide (10 mL) and filtered through a plug of Celite. The filtrate was extracted with ethyl acetate and the combined extracts were washed with brine, dried ($Na_2SO_4$), and concentrated. The residue was purified by flash chromatography over silica using ethyl acetate eluent to afford 2-(5-(4-(2-methoxyethoxy)phenyl)pyridin-2-yl)propan-2-amine as a yellow solid (0.800 g, 39%). To a stirred suspension of this intermediate (0.500 g, 1.75 mmol) in water (10 mL) and concentrated hydrochloric acid (0.44 mL) was added toluene (10 mL). The mixture was cooled (0° C.) and treated with, simultaneously over 1 hour, solutions of triphosgene (0.776 g, 2.62 mmol) in toluene (10 mL) and sodium bicarbonate (2.2 g, 26 mmol) in water (20 mL). Following the additions, the reaction was stirred for an additional 30 minutes before the upper toluene layer was removed and dried ($Na_2SO_4$). At the same time, a stirred solution of quinuclidin-3-ol (0.445 g, 3.64 mmol) in tetrahydrofuran (10 mL) was treated with sodium hydride (60% dispersion in mineral oil; 0.154 g, 3.85 mmol). This mixture was stirred for 5 minutes and then added to the solution of crude isocyanate in toluene. The reaction was stirred for 10 minutes, quenched with the addition of brine (5 mL), and extracted with ethyl acetate. The combined extracts were dried ($Na_2SO_4$) and concentrated. The residue was purified by flash chromatography over reversed phase silica to afford the title compound as a light yellow solid (0.100 g, 13%). $^1$H NMR (500 MHz, $CDCl_3$) δ 8.70-8.70 (d, J=2.0 Hz, 1H), 7.83-7.81 (m, 1H), 7.49-7.47 (d, J=9.0 Hz, 2H), 7.45-7.43 (d, J=8.0 Hz, 1H), 7.03-7.01 (d, J=8.5 Hz, 2H), 6.63 (br s, 1H), 4.68-4.66 (m, 1H), 4.16 (t, J=5.0 Hz, 2H), 3.77 (t, J=5.0 Hz, 2H), 3.45 (s, 3H), 3.19-2.70 (m, 6H), 2.15-1.89 (m, 2H), 1.76 (s, 6H), 1.73-1.36 (m, 3H) ppm. $^{13}$C NMR (125 MHz, $CDCl_3$) δ 162.7, 158.9, 154.9, 145.9, 134.8, 134.3, 130.1, 128.1, 119.2, 115.2, 71.0, 70.8, 67.4, 59.2, 55.9, 55.7, 47.4, 46.5, 46.4, 27.9, 25.4, 24.6, 19.5 ppm. Purity: >99% (214 & 254 nm) LCMS; retention time: 1.32 min; (M+H+) 440.2.

Quinuclidin-3-yl (2-(4'-(3-cyanopropoxy)-[1,1'-biphenyl]-4-yl)propan-2-yl)carbamate (Compound 22)

To a stirred solution of 4-bromophenol (17.1 g, 98.8 mmol) in acetonitrile (150 mL) was added 1-bromobutylnitrile (12.3 mL, 124 mmol) and potassium carbonate (15.0 g, 109 mmol). The mixture was heated to reflux overnight, cooled, and concentrated. The residue was taken up in water and extracted with ethyl acetate. The combined extracts were dried ($Na_2SO_4$) and concentrated and the crude material was purified by flash chromatography over silica using a hexane/ethyl acetate eluent to afford 4-(4-bromophenoxy)butanenitrile as a white solid (20.8 g, 88%). To a stirred solution of this product in N,N-dimethylformamide (100 mL), was added bis(pinacolato)diboron (4.60 g, 18.1 mmol), potassium acetate (7.41 g, 75.5 mmol), and [1,1'-bis(diphenylphosphino)ferrocene]-dichloropalladium(II) complex with dichloromethane (0.616 g, 1.04 mmol). The mixture was heated to reflux overnight and then concentrated. The residue was taken up in ethyl acetate and washed with water and brine. The organic layer was dried ($Na_2SO_4$) and concentrated and the crude product was purified by flash chromatography over silica using a hexane/ethyl acetate eluent to afford 4-(4-(4,4,5,5-tetramethyl-1,3,2-dioxaborolan-2-yl)phenoxy)butanenitrile as a white solid (3.43 g, 79%). This product and quinuclidin-3-yl (2-(4-bromophenyl)propan-2-yl)carbamate (prepared by reacting quinuclidin-3-ol and 2-(4-bromophenyl)propan-2-amine using General Procedure F) were reacted according to General Procedure E to generate the title compound as a white solid. $^1$H NMR (400 MHz, DMSO-d6) δ 7.67-7.26 (m, 7H), 7.02 (d, J=8.8 Hz, 2H), 4.50-4.33 (m, 1H), 4.08 (t, J=6.0 Hz, 2H), 3.14-2.18 (m, 8H), 2.04 (quin, J=6.7 Hz, 2H), 1.94-1.70 (m, 11H) ppm. $^{13}$C NMR (100 MHz, DMSO-d6) δ 157.7, 154.5, 146.8, 137.4, 132.7, 127.6, 125.7, 125.2, 120.2, 114.9, 70.0, 65.8, 55.4, 54.2, 46.9, 45.9, 29.4, 25.3, 24.7, 24.2, 19.2, 13.4 ppm. Purity: 100%, 98.9% (210 & 254 nm) UPLCMS; retention time: 0.88 min; (M+H+) 448.6.

Quinuclidin-3-yl (2-(4'-(cyanomethoxy)-[1,1'-biphenyl]-4-yl)propan-2-yl)carbamate (Compound 23)

Using General Procedure E and the reaction inputs quinuclidin-3-yl (2-(4-bromophenyl)propan-2-yl)carbamate (prepared by reacting quinuclidin-3-ol and 2-(4-bromophenyl)propan-2-amine using General Procedure F) and 4-(cyanomethoxy)phenylboronic acid, the title compound was prepared as a pale amber solid. $^1$H NMR (400 MHz, DMSO-d6) δ 7.65 (d, J=8.2 Hz, 2H), 7.60-7.31 (m, 5H), 7.15 (d, J=8.9 Hz, 2H), 5.21 (s, 2H), 4.53-4.30 (m, 1H), 3.18-2.19 (m, 6H), 2.05-1.18 (m, 11H) ppm. $^{13}$C NMR (100 MHz, DMSO-d6) δ 155.8, 154.6, 147.2, 137.2, 134.4, 127.8, 126.0, 125.3, 116.7, 115.3, 70.0, 55.4, 54.2, 53.5, 46.9, 45.9, 29.4, 25.2, 24.2, 19.2 ppm. Purity: 100%, 100% (210 & 254 nm) UPLCMS; retention time: 0.85 min; (M+H+) 420.3.

Example 2: Preparation of (S)-Quinuclidin-3-yl (2-(2-(4-fluorophenyl)thiazol-4-yl)propan-2-yl)carbamate free base Step 1: Dimethylation with Methyl Iodide

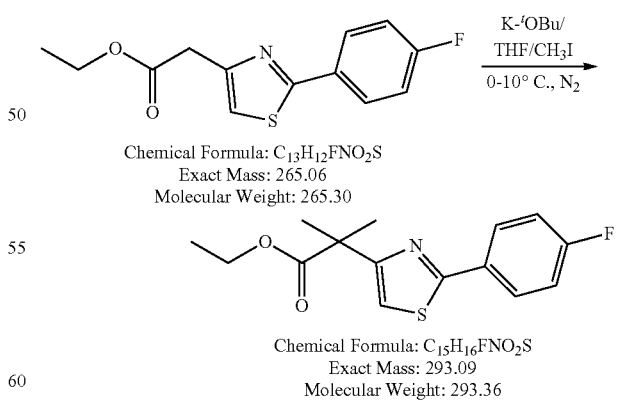

Chemical Formula: $C_{13}H_{12}FNO_2S$
Exact Mass: 265.06
Molecular Weight: 265.30

Chemical Formula: $C_{15}H_{16}FNO_2S$
Exact Mass: 293.09
Molecular Weight: 293.36

A 3N round-bottom (RB) flask was equipped with a thermometer, an addition funnel, and a nitrogen inlet. The flask was flushed with nitrogen and potassium tert-butoxide (MW 112.21, 75.4 mmol, 8.46 g, 4.0 equiv., white powder) was weighed out and added to the flask via a powder funnel followed by the addition of THF (60 mL). Most of the potassium tert-butoxide dissolved to give a cloudy solution. This mixture was cooled in an ice-water bath to 0-2° C. (internal temperature). In a separate flask, the starting ester (MW 265.3, 18.85 mmol, 5.0 g, 1.0 equiv.) was dissolved in THF (18 mL+2 mL as rinse) and transferred to the addition funnel. This solution was added dropwise to the cooled mixture over a period of 25-30 min, keeping the internal temperature below 5° C. during the addition. The reaction mixture was cooled back to 0-2° C. In a separate flask, a solution of methyl iodide (MW 141.94, 47.13 mmol, 6.7 g, 2.5 equiv.) in THF (6 mL) was prepared and transferred to the addition funnel.

The flask containing the methyl iodide solution was then rinsed with THF (1.5 mL) which was then transferred to the addition funnel already containing the clear colorless solution of methyl iodide in THF. This solution was added carefully dropwise to the dark brown reaction mixture over a period of 30-40 min, keeping the internal temperature below 10° C. at all times during the addition. After the addition was complete, the slightly turbid mixture was stirred for an additional 1 h during which time the internal temperature dropped to 0-5° C. After stirring for an hour at 0-5° C., the reaction mixture was quenched with the slow dropwise addition of 5.OM aqueous HCl (8 mL) over a period of 5-7 min. The internal temperature was maintained below 20° C. during this addition. After the addition, water (14 mL) was added and the mixture was stirred for 2-3 min. The stirring was stopped and the two layers were allowed to separate. The two layers were then transferred to a 250 mL 1N RB flask and the THF was evaporated in vacuo as much as possible to obtain a biphasic layer of THF/product and water. The two layers were allowed to separate. A THF solution of the Step 1 product was used in the next reaction.

Step 2: Hydrolysis of the Ethyl Ester with LiOH Monohydrate

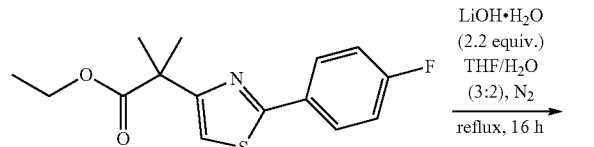

Chemical Formula: $C_{15}H_{16}FNO_2S$
Exact Mass: 293.09
Molecular Weight: 293.36

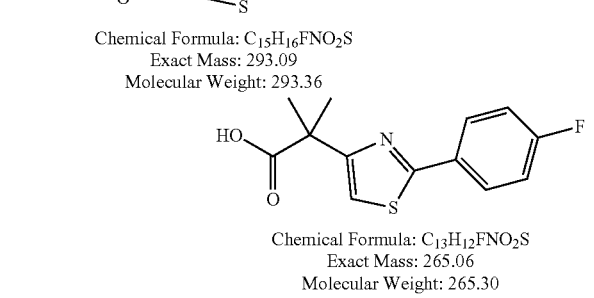

Chemical Formula: $C_{13}H_{12}FNO_2S$
Exact Mass: 265.06
Molecular Weight: 265.30

The crude ester in THF was added to the reaction flask. Separately, LiOH·H$_2$O (MW 41.96, 75.0 mmol, 3.15 grams, 2.2 equiv.) was weighed out in a 100 mL beaker to which a stir bar was added. Water (40 mL) was added and the mixture was stirred till all the solid dissolved to give a clear colorless solution. This aqueous solution was then added to the 250 mL RB flask containing the solution of the ester in tetrahydrofuran (THF). A condenser was attached to the neck of the flask and a nitrogen inlet was attached at the top of the condenser. The mixture was heated at reflux for 16 hours. After 16 hours, the heating was stopped and the mixture was cooled to room temperature. The THF was evaporated in vacuo to obtain a brown solution. An aliquot of the brown aqueous solution was analyzed by HPLC and LC/MS for complete hydrolysis of the ethyl ester. Water (15 mL) was added and this aqueous basic solution was extracted with TBME (2×40 mL) to remove the t-butyl ester. The aqueous basic layer was cooled in an ice-water bath to 0-10° C. and acidified with dropwise addition of concentrated HCl to pH ~ 1 with stirring. To this gummy solid in the aqueous acidic solution was added TBME (60 mL) and the mixture was shaken and then stirred vigorously to dissolve all the acid into the TBME layer. The two layers were transferred to a separatory funnel and the TBME layer was separated out. The pale yellow aqueous acidic solution was re-extracted with TBME (40 mL) and the TBME layer was separated and combined with the previous TBME layer. The aqueous acidic layer was discarded. The combined TBME layers are dried over anhydrous Na$_2$SO$_4$, filtered, and evaporated in vacuo to remove TBME and obtain the crude acid as an orange/dark yellow oil that solidified under high vacuum to a dirty yellow colored solid. The crude acid was weighed out and crystallized by heating it in heptane/TBME (3:1, 5 mL/g of crude) to give the acid as a yellow solid.

Step 3: Formation of Hydroxamic Acid with NH$_2$OH·HCl

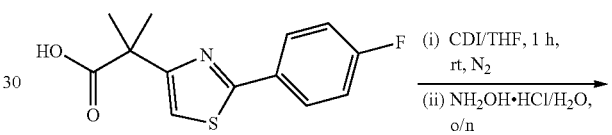

Chemical Formula: $C_{13}H_{12}FNO_2S$
Exact Mass: 265.06
Molecular Weight: 265.30

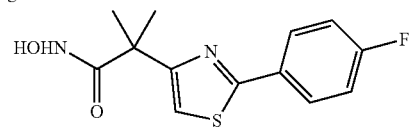

Chemical Formula: $C_{13}H_{13}FN_2O_2S$
Exact Mass: 280.07
Molecular Weight: 280.32

The carboxylic acid (MW 265.3, 18.85 mmol, 5.0 g, 1.0 equiv.) was weighed and transferred to a 25 mL 1N RB flask under nitrogen. THF (5.0 mL) was added and the acid readily dissolved to give a clear dark yellow to brown solution. The solution was cooled to 0-2° C. (bath temperature) in an ice-bath and N, N'-carbonyldiimidazole (CDI; MW 162.15, 20.74 mmol, 3.36 g, 1.1 equiv.) was added slowly in small portions over a period of 10-15 minutes. The ice-bath was removed and the solution was stirred at room temperature for 1 h. After 1 h of stirring, the solution was again cooled in an ice-water bath to 0-2° C. (bath temperature). Hydroxylamine hydrochloride (NH$_2$OH·HCl; MW 69.49, 37.7 mmol, 2.62 g, 2.0 equiv.) was added slowly in small portions as a solid over a period of 3-5 minutes as this addition was exothermic. After the addition was complete, water (1.0 mL) was added to the heterogeneous mixture dropwise over a period of 2 minutes and the reaction mixture was stirred at 0-10° C. in the ice-water bath for 5 minutes. The cooling bath was removed and the reaction mixture was stirred under nitrogen at room temperature overnight for 20-22 h. The solution became clear as all of the NH$_2$OH·HCl dissolved. After 20-22 h, an aliquot of the reaction mixture was analyzed by High Pressure Liquid Chromatography (HPLC). The THF was then evaporated in vacuo and the residue was taken up in dichloromethane (120 mL) and water (60 mL). The mixture was transferred to a separatory funnel where it was shaken and the two layers were allowed to separate. The water layer was discarded and the dichloromethane layer was washed with 1N hydrochloride (HCl; 60 mL). The acid layer was discarded. The dichloromethane layer was dried over anhydrous $Na_2SO_4$, filtered, and the solvent evaporated in vacuo to obtain the crude hydroxamic acid as a pale yellow solid that was dried under high vacuum overnight.

Step 3 Continued: Conversion of Hydroxamic Acid to Cyclic Intermediate (not Isolated)

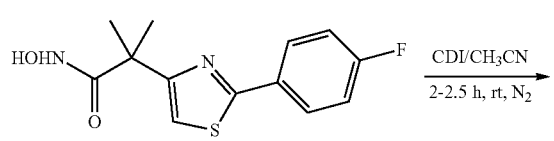

Chemical Formula: $C_{13}H_{13}FN_2O_2S$
Exact Mass: 280.07
Molecular Weight: 280.32

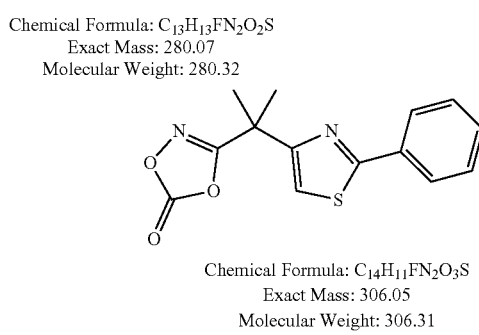

Chemical Formula: $C_{14}H_{11}FN_2O_3S$
Exact Mass: 306.05
Molecular Weight: 306.31

The crude hydroxamic acid (MW 280.32, 5.1 g) was transferred to a 250 mL 1N RB flask with a nitrogen inlet. A stir bar was added followed by the addition of acetonitrile (50 mL). The solid was insoluble in acetonitrile. The yellow heterogeneous mixture was stirred for 2-3 minutes under nitrogen and CDI (MW 162.15, 20.74 mmol, 3.36 g, 1.1 equiv.) was added in a single portion at room temperature. No exotherm was observed. The solid immediately dissolved and the clear yellow solution was stirred at room temperature for 2-2.5 h. After 2-2.5 h, an aliquot was analyzed by HPLC and LC/MS which showed conversion of the hydroxamic acid to the desired cyclic intermediate.

The acetonitrile was then evaporated in vacuo to give the crude cyclic intermediate as reddish thick oil. The oil was taken up in toluene (60 mL) and the reddish mixture was heated to reflux for 2 hours during which time, the cyclic intermediate released $C_{o2}$ and rearranged to the isocyanate (see below).

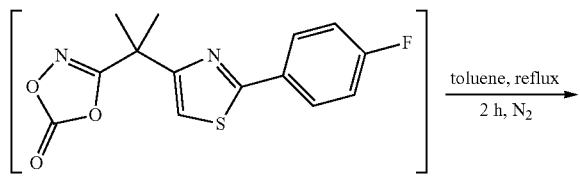

Chemical Formula: $C_{14}H_{11}FN_2O_3S$
Exact Mass: 306.05
Molecular Weight: 306.31

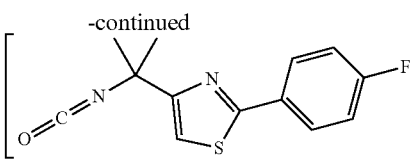

Chemical Formula: $C_{13}H_{11}FN_2OS$
Exact Mass: 262.06
Molecular Weight: 262.30

Step 3 Continued: Conversion of the Isocyanate to the Free Base

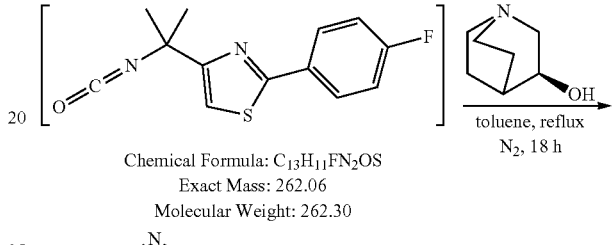

Chemical Formula: $C_{13}H_{11}FN_2OS$
Exact Mass: 262.06
Molecular Weight: 262.30

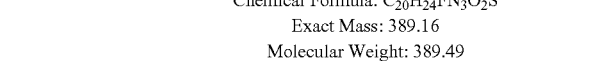

Chemical Formula: $C_{20}H_{24}FN_3O_2S$
Exact Mass: 389.16
Molecular Weight: 389.49

The reaction mixture was cooled to 50-60° C. and (S)-(+)-quinuclidinol (MW 127.18, 28.28 mmol, 3.6 g, 1.5 equiv.) was added to the mixture as a solid in a single portion. The mixture was re-heated to reflux for 18 h. After 18 h, an aliquot was analyzed by HPLC and LC/MS which showed complete conversion of the isocyanate to the desired product. The reaction mixture was transferred to a separatory funnel and toluene (25 mL) was added. The mixture was washed with water (2×40 mL) and the water layers were separated. The combined water layers were re-extracted with toluene (30 mL) and the water layer was discarded. The combined toluene layers were extracted with 1N HCl (2×60 mL) and the toluene layer (containing the O-acyl impurity) was discarded. The combined HCl layers were transferred to a 500 mL Erlenmeyer flask equipped with a stir bar. This stirring clear yellow/reddish orange solution was basified to pH 10-12 by the dropwise addition of 50% w/w aqueous NaOH. The desired free base precipitated out of solution as a dirty yellow gummy solid which could trap the stir bar. To this mixture was added isopropyl acetate (100 mL) and the mixture was stirred vigorously for 5 minutes when the gummy solid went into isopropyl acetate. The stirring was stopped and the two layers were allowed to separate. The yellow isopropyl acetate layer was separated and the basic aqueous layer was re-extracted with isopropyl acetate (30 mL). The basic aqueous layer was discarded and the combined isopropyl acetate layers were dried over anhydrous $Na_2SO_4$, filtered into a pre-weighed RB flask, and the solvent evaporated in vacuo to obtain the crude free base as beige to tan solid that was dried under high vacuum overnight.

Step 3 Continued: Recrystallization of the Crude Free Base

The beige to tan colored crude free base was weighed and re-crystallized from heptane/isopropyl acetate (3:1, 9.0 mL of solvent/g of crude free base). The appropriate amount of heptane/isopropyl acetate was added to the crude free base along with a stir bar and the mixture was heated to reflux for 10 min (free base was initially partially soluble but dissolved to give a clear reddish orange solution when heated to reflux). The heat source was removed and the mixture was allowed to cool to room temperature with stirring when a white precipitate formed. After stirring at room temperature for 3-4 h, the precipitate was filtered off under hose vacuum using a Buchner funnel, washed with heptane (20 mL) and dried under hose vacuum on the Buchner funnel overnight. The precipitate was the transferred to a crystallizing dish and dried at 55° C. overnight in a vacuum oven. $^1$H NMR (400 MHz, CDCl$_3$) δ 8.04-7.83 (m, 2H), 7.20-6.99 (m, 3H), 5.53 (s, 1H), 4.73-4.55 (m, 1H), 3.18 (dd, J=14.5, 8.4 Hz, 1H), 3.05-2.19 (m, 5H), 2.0-1.76 (m, 11H) ppm. $^{13}$C NMR (100 MHz, CDCl$_3$) δ 166.38, 165.02, 162.54, 162.8-155.0 (d, C-F), 130.06, 128.43, 128.34, 116.01, 115.79, 112.46, 71.18, 55.70, 54.13, 47.42, 46.52, 27.94, 25.41, 24.67, 19.58 ppm.

Example 3: Preparation of Crystalline Forms of (S)-Quinuclidin-3-yl (2-(2-(4-fluorophenyl)thiazol-4-yl)propan-2-yl)carbamate salts Crystalline salts of (S)-Quinuclidin-3-yl (2-(2-(4-fluorophenyl)thiazol-4-yl)propan-2-yl)carbamate may be formed from the free base prepared as described in Example 23.

For example, the free base of (S)-Quinuclidin-3-yl (2-(2-(4-fluorophenyl)thiazol-4-yl)propan-2-yl)carbamate (about 50 mmol) is dissolved IPA (140 ml) at room temperature and filtered. The filtrate is added into a 1 L RB flask which is equipped with an overhead stirrer and nitrogen in/outlet. L-malic acid (about 50 mmol) is dissolved in IPA (100+30 ml) at room temperature and filtered. The filtrate is added into the above 1 Liter flask. The resulting solution is stirred at room temperature (with or without seeding) under nitrogen for 4 to 24 hours. During this period of time, crystals form. The product is collected by filtration and washed with a small amount of IPA (30 ml). The crystalline solid is dried in a vacuum oven at 55° C. for 72 hours to yield the desired malate salt.

Crystal forms of other salts, e.g., acid addition salts with succinic acid or HCl, may be prepared in an analogous manner.

Example 4: In-Vitro GCS Inhibition (Compound 2 and Analogs)

Inhibition of glucosylceramide synthase activity can be measured with one or more assays. A first assay is a microsomal assay that directly measures the conversion of ceramide to glucosylceramide by HPLC. Microsomes are a source of glucosylceramide synthase activity in the microsomal assay. A second assay is a cell based, phenotypic assay that monitors cell surface expression of the downstream lipid GM3 by antibody mediated immunofluorescence. Specific protocols are provided below.

Glucosylceramide Synthase Activity Microsomal Assay:

An enzyme assay using microsomes as a source of glucosylceramide synthase activity. Fluorescent ceramide substrate is delivered to membrane-bound enzyme as a complex with albumin. After reaction, ceramide and glucosylceramide are separated and quantitated by reverse-phase HPLC with fluorescence detection. Enzymatic activity is assessed using a fluorescent labeled substrate and microsomes as a source of glucosylceramide synthase. $C_6$-NBD-Ceramide is complexed with albumin for delivery to microsomes that are isolated according to the procedure described below. The final concentration of $C_6$-NBD-Ceramide in the stock solution is 0.5 mM; the final concentration of BSA is 0.5 mM. Separation and quantitation of substrate and product (glucosylceramide) are achieved by reverse-phase HPLC with fluorescence detection.

Preparation of Microsomes from A375 Human Melanoma Cells;

Microsomes are isolated from A375 human melanoma cells. Eight to ten million cells are harvested by trypsinization and washed with ice cold PBS. Cells are resuspended in ice-cold lysis buffer containing protease inhibitors. Cell lysate is sonicated on ice using a probe sonicator. After sonication, the cell lysate is separated from debris by centrifugation at 10,000 g for 10 minutes at 4° C. The supernatant is removed and cleared by additional centrifugation at 100,000 g for 1 hour at 4° C. The pellet is then resuspended in the lysis buffer, aliquoted, and stored at −80° C. prior to use.

Glucosylceramide Synthase Assay

To determine glucosylceramide synthase inhibition, substrates at 2× of their Km (fluorescent ceramide and UDP-glucose, 3 µM and 4 µM respectively) and microsomes (1:50 dilution) are combined 1:1 and incubated at room temperature for 1 hour in the dark on a plate shaker. The reaction is stopped by the addition of 150 µL of 100 µM $C_8$-ceramide in 50% aq. isopropanol; 10 µL of the final mix is analyzed on HPLC (with fluorescence detector). The mobile phase is 1% formic acid added to 81% methanol/19% water with flow rate 0.5 mL/min. Fluorescence is detected with $\lambda_{ex}$=470 nm and $\lambda_{em}$=530 nm. Under these conditions, NBD-$C_6$-GluCer had a retention time of about 1.7 min and NBD-$C_6$-Cer elutes from the column after about 2.1 min. Both peaks are separated from each other and the baseline and were integrated automatically by the HPLC software. The percent conversion of substrate to product is used as the readout for inhibitor testing.

GM3 Fluorescent-Linked ImmunosorbentAssay (FLISA):

This is a phenotypic assay that measures GM3 expression in B16 mouse melanoma or C32 human melanoma cells following treatment with test compounds. Cell surface GM3 expression is determined by antibody mediated fluorescence.

Compounds are diluted in media and plated in 384 well plates in DMSO. B16 and C32 cells are assayed at densities of 20,000 cells/ml and 62,500 cells/ml, respectively, per well. Each titration curve contains 10 points that are assayed in duplicate on each test run. The plates are incubated for 48 hours at 37° C., 5% CO2, and are then washed once with TBS. Anti-GM3 antibody is added to each well and the plates are then incubated for an additional one hour at room temperature. Plates are subsequently washed twice and incubated for an additional hour with the labeled secondary antibody. Following the final incubation, the plates are washed twice and the fluorescence at $\lambda_{ex}$=D640/20 nm and $\lambda_{em}$=657 nm is detected on a fluorescent reader.

Assay Results

Individual assay results of certain exemplified compounds in these assays are presented in the Table below. The results of the microsomal assays are expressed as "GCS IC$_{50}$," which represents the concentration of the compound causing 50% inhibition of glucosylceramide synthase activity. The results of the cell-based assays are expressed as "GM3 B16 IC$_{50}$" or "GM3 C32 IC$_{50}$" for the B16 assay and the C32 assay, respectively. These values represent the concentration of the compound causing 50% inhibition of GM3 expression on the cell surface.

| Compound No. | GCS $IC_{50}$ (mM) | GM3 B16 $IC_{50}$ (mM) | GM3 C32 $IC_{50}$ (mM) |
|---|---|---|---|
| 1 | 0.0019 | 0.0156 | 0.0021 |
| 2 | 0.0601 | 0.1068 | 0.0096 |
| 3 | 0.00414 | 0.0437 | 0.00131 |
| 4 | 0.0015 | 0.0116 | 0.0008 |
| 5 | 0.0012 | 0.0193 | 0.0003 |
| 6 | 0.0028 | 0.0181 | 0.0006 |
| 7 | 0.0014 | 0.0081 | 0.0004 |
| 8 | 0.0010 | 0.0075 | 0.0004 |
| 9 | 0.0014 | 0.0168 | 0.0004 |
| 10 | 0.0064 | 0.0213 | 0.0022 |
| 11 | 0.0149 | 0.0819 | 0.0018 |
| 12 | 0.0203 | 0.0878 | 0.0037 |
| 13 | 0.0035 | 0.0386 | 0.0007 |
| 14 | 0.0104 | 0.1096 | 0.0053 |
| 15 | 0.0267 | 0.0295 | 0.0049 |
| 16 | 0.0024 | 0.0666 | 0.0016 |
| 17 | 0.4544 | 0.8786 | 0.0216 |
| 18 | 0.1480 | 0.6555 | 0.0223 |
| 19 | 0.1701 | 0.1972 | 0.0426 |
| 20 | 0.3601 | 0.1065 | 0.0198 |
| 21 | 0.0506 | 0.2658 | 0.0111 |
| 22 | 0.0096 | 0.0865 | 0.0032 |
| 23 | 0.0026 | 0.0477 | 0.0008 |

These comparative results demonstrate that compounds according to the present disclosure have comparable in-vitro activity as inhibitors of GCS, and as a result, are expected to demonstrate similar in-vivo benefits.

Example 5: Clinical Study of Compound 2 in GD-3 Patients

A 156-week, multi-part, open-label, multinational study of the safety, tolerability, pharmacokinetics, pharmacodynamics, and exploratory efficacy of Compound 2 in combination with imiglucerase in adult patients with Gaucher disease Type 3 stabilized with imiglucerase was initiated (called LEAP or LEAP2IT trial). Compound 2 is administered orally in the malate salt form (L-malic acid) at a dose of 15 mg/day (measured as the quantity of free base) in a single daily dose. The endpoint assessments are related to safety, CSF biomarkers, pharmacokinetics/pharmacodynamics, systemic disease, and neuroimaging and neurological function (CNS/neurological manifestations).

Patients 18 years of age or older with a clinical diagnosis of GD3 and documented deficiency of acid beta-glucosidase activity having received treatment with ERT for at least 3 years and with imiglucerase (Cerezyme) at a stable monthly dose for at least 6 months prior to enrollment were included in the study. Patients must have reached the following GD therapeutic goals: hemoglobin level of ≥11.0 g/dL for females and ≥12.0 g/dL for males; platelet count 100 000/mm$^3$; spleen volume <10 multiples of normal (MN), or total splenectomy (provided the splenectomy occurred ≥3 years prior to randomization); liver volume <1.5 MN; and no bone crisis and free of symptomatic bone disease such as bone pain attributable to osteonecrosis and/or pathological fractures within the last year. Patients must have GD3 featuring oculomotor apraxia (supranuclear gaze palsy) characterized by a horizontal saccade abnormality.

(A) 52-Week Interim Analysis (N=6)

An interim analysis was performed when 6 patients had completed 52 weeks of concurrent treatment with (1) imiglucerase (Cerezyme from Sanofi Genzyme) under each patient's established regimen, and (2) Compound 2 administered orally at 15 mg/day in a single dose. During the study patients were evaluated for safety and tolerability, CSF and plasma biomarkers (glucosylceramide, GL-1; glucosylsphingosine, lyso-GL1), pharmacokinetics, markers for systemic disease (spleen and liver volume measured by magnetic resonance imaging (MRI), platelet count, hemoglobin levels), indicia of interstitial lung disease (high resolution pulmonary computed tomography (CT)), and horizontal saccadic eye movement. In addition, exploratory biomarkers were quantified in CSF of GD3 patients: ceramide (the precursor of GL-1), chitotriosidase (CHITO), GM3, and GPNMB. Symptoms of ataxia were measured using the SARA scale, neurological symptoms were measured using the trail making test, and functional MRI was used to assess neural connectivity in the brain.

At baseline, five patients had mild neurological involvement and one had moderate neurological involvement, as measured using the Modified Severity Scoring Tool (mSST; see e.g., Davies, et al., J Inherit Metab Dis. (2011) 34 (5), pp 1053-1059).

Analysis of plasma and CSF concentrations of Compound 2 shows that Compound 2 effectively cross the blood-brain barrier in all patients. Patient 5, however, is found to have about 50% lower concentrations of Compound 2 in plasma and CSF at Week 26, and undetectable concentrations at Week 52. It is believed that this is due to either compliance or dosing errors, and therefore, analysis is repeated without Patient 5's Week 26 and 52 data included. The data supports the conclusion that a steady state concentration of Compound 2 is reached in plasma and CSF at or prior to Week 4:

| Compound 2 in plasma | Day 1 (N = 6) |
|---|---|
| $AUC_{0-24}$, ng · h/mL (mean ± SD) | 729 ± 205 |
| $C_{max}$, ng/ml (mean ± SD) | 49.1 ± 17.3 |
| $t_{max}$, h (median) | 2.00 |

| | Day 1 (N = 6) | Week 4 (N = 6) | Week 26 (N = 6) | Week 52 (N = 6) |
|---|---|---|---|---|
| Compound 2 in Plasma | | | | |
| Concentration 2-4 hours post dose, ng/ml (mean ± SD) | 39.7 ± 12.6 | 92.3 ± 36.4 | 102.0 ± 49.5 | 69.8 ± 58.3 |
| Excluding Patient 5 | | | 112 | 84 |
| Compound 2 in CSF | | | | |
| Concentration 2-4 hours post dose, ng/ml (mean ± SD) | <LLOQ | 4.56 ± 1.20 | 5.26 ± 2.49 | 4.43 ± 3.23 |
| Excluding Patient 5 | | | 6.13 | 5.32 |

At 52 weeks, the data further shows sustained significant improvements in plasma and CSF biomarkers for GD-3. Over all six GD3 patients, plasma and CSF GL-1 and lyso-GL-1 concentrations were as follows:

|  | Lyso-GL-1 | | GL-1 | |
| --- | --- | --- | --- | --- |
|  | Baseline | 52-weeks | Baseline | 52-weeks |
| Plasma | 29.3 ng/ml (6.3-159.0) | 15.2 ng/ml (2.5-46.8) | 6.21 µg/mL (4.2-8.3) | 1.59 µg/mL (0.9-2.7) |
| CSF | 34.0 pg/mL (20.1-67.6) | 17.3 pg/mL (5.8-37.4) | 6.36 ng/ml (4.4-11.1) | 2.48 ng/ml (1.0-6.1) |

Thus, at 52-weeks compared to baseline, plasma and CSF concentrations had changed as follows:

|  | Lyso-GL-1 (% change) | GL-1 (% change) |
| --- | --- | --- |
| Plasma Concentration | −56.7% | −71.6% |
| CSF Concentration | −55.9% | −55.4% |

In addition, exploratory biomarkers were quantified in CSF of GD3 patients: ceramide (the precursor of GL-1), chitotriosidase (CHITO; an enzyme known to be elevated in GD patients), GM3 (a glycosphingolipid marker known to be elevated in GD patients), and GPNMB (glycoprotein nonmetastatic melanoma protein B, reportedly a biomarker of neuropathic GD3). After 52 weeks of treatment, no significant changes were observed in CSF concentrations of ceramide, CHITO, or GPNMB. Four of the six patients had measurable concentrations of GM3 in CSF at baseline, and each of these patients was found to have undetectable GM3 in CSF at 4 weeks, 26 weeks, and 52 weeks.

In addition, at 52 weeks, 5 of 6 patients showed improvements in ataxia. The degree of ataxia at baseline and throughout the study was evaluated by the Scale for Assessment and Rating of Ataxia (SARA; Schmitz-Hubsch et al. [2006]), which assesses eight distinct attributes of cerebellar ataxia on a scale of 0-40. The eight attributes are gait, stance, sitting, speech disturbance, finger chase, nose-finger test, fast alternate hand movement, and heel-shin slide. SARA ataxia scoring results for all six patients is presented in the chart below:

| SARA Cumulative Score | At Screening | Week 26 | Week 52 |
| --- | --- | --- | --- |
| Patient 1 | 3.0 | 1.0 | 0.0 |
| Patient 2 | 3.0 | 2.0 | 1.5 |
| Patient 3 | 3.5 | 0.0 | 0.0 |
| Patient 4 | 3.0 | 5.0 | 4.5 |
| Patient 5 | 0.5 | 0.0 | 0.0 |
| Patient 6 | 4.0 | 2.0 | 3.0 |
| Average Score | 2.83 | 1.67 | 2.00 |
| Average Score excluding Patient 4 | 2.80 | 1.00 | 0.90 |

As shown in the table, five of the six patients were mildly ataxic at baseline, with the mean cumulative SARA score being 2.8 (SD=1.2). The most common deficits at baseline were gait disorders. Excluding Patient 5 due to the low level of Compound 2 exposure in this patient and the patient's substantially normal baseline ataxia score (only 0.5), then 4 out of 5 patients exhibited an improvement in ataxia at Week 52 (mean improvement=−0.9; SD=3.2). Patient 4 exhibited an increase in ataxia scoring, with the score at baseline being 3 and at Week 52, 7.5. It should be noted that this apparent deterioration was driven almost entirely by a change in the 'stance' scoring parameter (stance score at baseline and Week 26=1; score at Week 52=5) and that the patient was complaining of left knee pain at the time of the exam. Additionally, the subject had injured his left great toe prior to the exam; this injury was considered resolved 11 days after the exam. Excluding these outlier effect of Patient 4, treatment with Compound 2 resulted in a significantly decreased mean SARA Score by Week 26 which was further slightly improved upon by Week 52.

The trail making test (TMT) was used to evaluate cognitive function in the patients. The TMT is one of the most widely used neuropsychological tests and is included in most test batteries. The TMT is a diagnostic tool to assess general intelligence and cognitive dysfunctions (Tombaugh et al. [2004]; Cavaco et al. [2013]). In part A of the TMT (TMT-A), subjects are asked to connect a cluster of numbers in ascending order (Trail A). This task is a combination of visual search and general visual and motor processing speed. Part B (TMT-B) presents a sequence which alternates between numbers and letters (Trail B). Subjects must actively switch between both categories when connecting them in ascending, but alternating order. Hence, this task is considered to include an executive function component since the subject must actively switch between categories while connecting the symbols (MacPherson et al. [2017]).

TMT-A evaluates mainly perceptual and psychomotor speed. TMT-B assesses more specifically mental flexibility and shifting abilities. TMT-B minus TMT-A score is used to remove the variance attributable to the graphomotor and visual scanning components of TMT-A. This derived score reflects the unique task requirements of TMT-B.

In a study of normative data for TMT-A and TMT-B in community-dwelling individuals aged 18-89 years (n=911), mean (SD) values in the 18-24 years age group (n=155) were 22.9 s (6.9) for TMT-A and 49 s (12.7) for TMT-B (Tombaugh et al. [2004]). In contrast, the mean times taken to complete Trail A and Trail B for patients in the study were 67.8 s (SD=60.3 s) and 193.8 s (SD=197.0), respectively. At baseline, the mean difference in time taken to complete Trail B minus Trail A was 126.0 s (SD=142.9 s). This shows that the GD-3 patients in this study demonstrated some degree of cognitive dysfunction at baseline.

At Week 52, the mean period of time taken to complete Trail A was 56.5 s (SD=55.2 s) and Trail B was 122.7 s (SD=91.8 s). Four of six patients exhibited reduction in time taken to complete Trail A and six of six exhibited reduction in time taken to complete Trail B. Excluding Patient 5 due to the low level of Compound 2 exposure in this patient, four of five patients exhibited a TMT-A reduction and five of five patients exhibited a TMT-B reduction.

At Week 52, 5 of 6 patients exhibited a reduction in the (TMT-B−TMT-A) time. Individual results are shown in the table below.

| TMT-A (s)-TMT-B (s) | At Screening | Week 26 | Week 52 | Change (%) from Baseline to Week 52 |
| --- | --- | --- | --- | --- |
| Patient 1 | 13 | 21 | 16 | +23% |
| Patient 2 | 71 | 37 | 57 | −20% |
| Patient 3 | 72 | 56 | 20 | −72% |

| TMT-A (s)-<br>TMT-B (s) | At<br>Screening | Week<br>26 | Week<br>52 | Change (%)<br>from Baseline<br>to Week 52 |
|---|---|---|---|---|
| Patient 4 | 116 | (no data) | 66 | −43% |
| Patient 5 | 74 | 60 | 72 | −3% |
| Patient 6 | 410 | 440 | 166 | −60% |
| Average | 126 (n = 6) | 123 (n = 5) | 66 (n = 6) | −29% |

At 52 weeks, the mean difference in time taken to complete Trail B minus Trail A was 66.2 s (SD=54.3). Excluding Patient 5, four of five patients exhibited an improvement in Trail B minus Trial A at Week 52, with a mean improvement of −71.4 s (−31.6%) (SD 99.3 s (37.6%)).

Neurological function was further evaluated using functional magnetic resonance imaging (fMRI). Patient 2 was excluded because no fMRI data was collected at the Week 52 session. Resting-state fMRI screening sessions were performed at baseline screening, Week 26, and Week 52 visits. Connectivity estimates from four subjects (Patients 1, 3, 4, and 5) were entered into second-level analyses as a "compliant" group. Patient 5 was isolated due to likely non-compliance with study medication, as described above. Analyses were performed as described elsewhere (Smith et al. [2009]).

It was found that the compliant subjects demonstrate an enhanced connectivity between a more broadly distributed set of brain regions than the non-compliant subject, with increasing strength between posterior and anterior aspects as the most prominent feature. At the anatomic level, compliant subjects demonstrate a widespread and robust strengthening of connections between occipital-parietal structures and frontal, temporal, and limbic targets. Connectivity changes in Patient 5 were more modest and restricted within spatially proximal structures. At the functional level, enhanced connectivity between default mode and medial frontal networks is seen in every subject except Patient 5. This suggests signal within these disparate networks becomes more coherent, such that brain activity can be more efficiently transferred between cognitive reserve (posterior) and higher-order executive functions (anterior). A consistent reciprocal mapping of resting state networks (RSNs) 2 and 3 ("cognition-language-orthography" and "cognition-space") to RSNs 8 and 9 (executive and left frontoparietal) is also evident. The spatial distribution of connectivity changes is much more focal for Patient 5, primarily reflecting overlap between medial-frontal and frontoparietal networks. Both perspectives suggest that patients who fully complied with the treatment protocol developed greater coherence between posterior and anterior aspects of the brain, such that the entire brain becomes amenable to efficient information transfer. Where apparent, altered connectivity for Patient 5 appears within a narrower set of anterior brain regions and represents less holistic evidence of therapeutic benefit.

The results are summarized in the table below. Spatial analysis of the connectivity between different anatomic regions of the brain is performed to define a correlation coefficient for regressed voxelwise mean intensity. The results show that connectivity between the default mode (resting) network and the executive function network increased in Patients 1, 3, 4, and 6, but decreased in Patient 5.

|  | Patient 1 | Patient 3 | Patient 4 | Patient 5 | Patient 6 |
|---|---|---|---|---|---|
| Change in Correlation Coefficient | +0.20 | +0.20 | +0.20 | −0.13 | +0.70 |

(B) 52-Week Interim Analysis (N=11)

An additional interim analysis was performed when 11 patients had reached the 52-week milestone. The results of this analysis confirm the observation made at the previous interim analysis.

The 11 patients at the second interim analysis included 7 men and 4 women. 8 patients were homozygous for the p.Leu483Pro (a.k.a. L444P) mutation in the beta-galactosidase gene, 2 were compound heterozygous for p.Phe523Ile/p.Leu483Pro variants, and one was compound heterozygous for p.Asp448His/p.Arg502Cys variants. Nine of the 11 patients were mildly ataxic at baseline, mostly with gait disorder. Two were considered not ataxic or very mildly ataxic. All 11 patients are continuing the study. No major adverse events are reported, the most frequent events being mild headache and back pain, and these were determined to be likely related to the lumbar puncture intervention for CSF sampling.

Plasma and CSF concentrations of the Compound 2 were measured as described above. As was previously observed, one patient (Patient 5) is an outlier demonstrating very low plasma and CSF levels of Compound 2. The data continues to support the conclusion that a steady state concentration of Compound 2 is reached in plasma and CSF at or prior to Week 4:

| Compound 2 in plasma | Day 1 (N = 11) |
|---|---|
| $AUC_{0-24}$, ng · h/mL (mean ± SD) | 851 ± 282 |
| $C_{max}$, ng/ml (mean ± SD) | 58.1 ± 26.4 |
| $t_{max}$, h (median) | 2.00 |

In the following chart, Patient 5 is excluded from the mean (N=10) values.

| Compound 2 in Plasma | Week 4 (N = 10) | Week 26 (N = 10) | Week 52 (N = 10) |
|---|---|---|---|
| Concentration 2-4 hours post dose, ng/ml (mean ± SD) | 116 ± 48.1 | 120 ± 40.1 | 114 ± 65.8 |
| Patient 5 Only, ng/ml | 102 | 53.3 | <LLOQ |

| Compound 2 in CSF | Week 4 (N = 10) | Week 26 (N = 8) | Week 52 (N = 10) |
|---|---|---|---|
| Concentration 2-4 hours post dose, ng/ml (mean ± SD) | 6.63 ± 2.42 | 6.77 ± 1.96 | 6.14 ± 3.44 |
| Patient 5 Only, ng/ml | 3.05 | 1.77 | <LLOQ |

One patient (Patient 1) also experienced a significant drop in plasma and CSF concentrations of the compound beginning at the 52-week measurement, and this was traced to being likely a result of co-treatment with the CYP3A4 inducer rifampicin from Week 39 to Week 51 of the study. Because Compound 2 is suspected to be a CYP3A substrate, concomitant administration with CYP3A inducers is anticipated to result in a reduced systemic exposure.

At 52 weeks, the data further shows sustained significant improvements in plasma and CSF biomarkers for GD3, with the exception of Patient 5. Initial evidence of Compound 2 exposure correlated with reduction in lyso-GL1 and GL1 in CSF and plasma. Subsequently, reduced levels of Compound 2 exposure corresponded with an increase in both lyso-GL1 and GL1 in both the CSF and plasma. At Week 52, the CSF lyso-GL1 concentrations for Patient 5 were above the upper limit of quantification (ULOQ; >100 pg/mL), and biomarker results for CSF lyso-GL1 were therefore imputed using the exact ULOQ values. Accordingly, in Patient 5, CSF lyso-GL1 and GL1 was found to increase by about 313% and 37%, respectively, at Week 52 compared to baseline, and levels of plasma lyso-GL1 and GL1 increased by about 43% and 14%, respectively, at Week 52 compared to baseline. Mean results for the other study subjects were as follows (N=10; Patient 5 excluded):

|  | Lyso-GL-1 | | GL-1 | |
| --- | --- | --- | --- | --- |
|  | Baseline | 52-weeks | Baseline | 52-weeks |
| Plasma | 27.6 ng/ml (5.7-79.8) | 13.6 ng/ml (2.5-46.8) | 5.66 µg/mL (4.2-7.9) | 1.28 µg/mL (0.7-2.7) |
| CSF | 45.0 pg/mL (19.8-100) | 14.5 pg/mL (2.5-37.4) | 7.11 ng/ml (4.3-14.3) | 1.38 ng/ml (1.0-3.7) |

Thus, at 52-weeks compared to baseline, plasma and CSF concentrations had changed as follows (N=10; Patient 5 excluded):

|  | Lyso-GL-1 (% change) | GL-1 (% change) |
| --- | --- | --- |
| CSF Concentration | −68% ± 17.2% | −79% ± 12.1% |
| Plasma Concentration | −53% ± 13.5% | −77% ± 11.7% |

SARA ataxia scoring results for the five new patients is presented in the chart below:

| SARA Cumulative Score | At Screening | Week 26 | Week 52 |
| --- | --- | --- | --- |
| Patient 7 | 5.5 | 7.5 | 5.0 |
| Patient 8 | 2.0 | 0.5 | 0 |
| Patient 9 | 0.0 | 0.0 | 0.0 |
| Patient 10 | 2.0 | 2.0 | 1.0 |
| Patient 11 | 3.0 | 3.0 | 2.0 |

As shown in the table, excluding Patient 9, who did not suffer from ataxia at baseline, 4 out of 4 patients exhibited an improvement in ataxia at Week 52. Patient 7 exhibited a transient increase in ataxia scoring, which resolved by Week 52.

To further demonstrate improvements in ataxia, two patients are videotaped at screening and at week 26 and week 52 timepoints attempting to walk along a straight line. A comparison of the video evidence demonstrates that compared to baseline, both patients show a steadier, better coordinated, and faster gait, with fewer touches against the nearby wall for support and fewer sidesteps.

TMT timing for the new patients is shown in the chart below.

| TMT-A (s)- TMT-B (s) | At Screening | Week 26 | Week 52 | Change (%) from Baseline to Week 52 |
| --- | --- | --- | --- | --- |
| Patient 7 | 86 | 83 | 110 | +28% |
| Patient 8 | 100 | 54 | 59 | −41% |
| Patient 9 | 59 | 45 | 75 | +27% |
| Patient 10 | 73 | 33 | 6 | −92% |
| Patient 11 | 18 | 48 | 32 | +78% |

At 52 weeks, three of the new patients showed small increases in the (TMT-B−TMT-A) time of uncertain clinical significance, while two of the new patients showed a decrease in the (TMT-B−TMT-A) time, one patient showing an extremely large decrease (92% drop).

Neurological function was further evaluated in the new patients using functional magnetic resonance imaging (fMRI), as described above. fMRI results continue to indicate that patients with sufficient Compound 2 exposure develop greater coherence between posterior and anterior aspects of the brain, such that the entire brain becomes amenable to efficient information transfer. Where apparent, altered connectivity for the single patient with insufficient Compound 2 exposure (Patient 5) appears within a narrower set of anterior brain regions, and represents less holistic evidence of therapeutic benefit. This enhanced connectivity is seen in regions associated with executive function. Resting-state functional MRI demonstrates enhanced connectivity between default mode and medial frontal networks, suggesting that signaling within these disparate networks becomes more coherent, such that brain activity can be more efficiently transferred between cognitive reserve (posterior) and higher-order executive functions (anterior).

In particular, the results show enhanced connectivity between RSNs 1, 2 and 3 (perception-vision, cognition-language-orthography, and cognition space) and RSNs 6, 7 and 8 (sensorimotor, auditory, and executive control). At an anatomic level, there is a widespread and robust strengthening of connections between occipital-parietal structures and frontal, temporal, and limbic targets. This data is suggestive of increased functional connectivity that is most prominent within sensory, motor, and cerebellar networks which are thought to be disrupted in Gaucher disease.

The results are summarized in the table below for all patients for RSNs 3 and 6 (RSNs 4 and 8 are not included) for the change in correlation coefficient between baseline and 52 weeks (as noted supra, Patient 2 is excluded because of lack of data).

|  | Patient 1 | Patient 3 | Patient 4 | Patient 5 | Patient 6 |
| --- | --- | --- | --- | --- | --- |
| Change in Correlation Coefficient | 0.359 | 0.383 | 0.201 | −0.173 | 0.779 |

|  | Patient 7 | Patient 8 | Patient 9 | Patient 10 | Patient 11 |
| --- | --- | --- | --- | --- | --- |
| Change in Correlation Coefficient | −0.013 | −0.058 | −0.302 | 0.105 | 0.035 |

Statistical analysis of the SARA and TMT results compared to GL-1 concentration in GSF at 52 weeks is found to provide a good therapeutic correlation. For the SARA results, in which lower scores indicate therapeutic improvement, 8 of 11 patients show a positive correlation between reduction in CSF GL-1 (ng/mL) and SARA score (−5 to 5). For TMT, also in which shorter (Trail B minus Trail A) times indicate therapeutic improvement, 6 of 11 patients show a positive correlation between reduction of CSF GL-1 (ng/mL) and TMT time (seconds).

(C) Additional 52-Week Interim Analysis (N=9)

Neurological function was further evaluated using volumetric magnetic resonance imaging (vMRI). The vMRI data was collected at screening sessions at baseline and after 52 weeks of the treatment regime for eight patients ("Group A") and an additional isolated patient (Patient 5). Group A corresponds to the eleven patients described above, excluding Patient 5 and two other patients lacking analyzable vMRI data. Patient 5 was isolated due to having plasma and CSF concentration of Compound 2, lower than the LLOQ after 52 weeks, suggesting failure to comply with the treatment regime.

vMRI data was obtained and subsequently analyzed using FreeSurfer anatomic parcellation and a Tensor-Based Morphometry (TBM) analysis cycle. FreeSurfer is an open-source software package for the analysis and visualization of structural and functional neuroimaging data developed by the Laboratory for Computational Neuroimaging. TBM analysis (also known as Jacobian Integration) consists in estimating the volume changes as captured within the deformation fields resulting from applying a symmetric deformable registration technique between a pair of MR scans (baseline and follow-up), using a non-linear symmetric log-demons deformation technique using robust cross-correlation metric to ensure invertibility of the transformation (symmetric process). The deformation field is then analyzed by computing the determinant of its Jacobian matrix, which is a measure of local volume change. An integration of the determinant over a region of interest provides an estimation of the change rate of the volume of this brain region over time.

The overall pipeline takes as input a baseline (BL) and a follow-up (FU) image and consists of the following steps:
1. Preprocessing and reformatting;
2. Segmentation of baseline (BL) and follow-up (FU) using FreeSurfer;
3. Multi-resolution rigid and affine registration of FU and BL to midspace;
4. Symmetric deformable nonlinear registration between FU and BL;
5. Jacobian image computation;
6. Voxel-wise volume change computation;
7. Region-wise volume change integration; and
8. Output for the changes for regions of interest specified for the study.

TBM is thus an image analysis technique that identifies regional structural differences from the gradients of the nonlinear deformation fields that align images to a common anatomical template. TBM is a well-known tool for analyzing brain vMRI data and further discussion of the application of the technique in that context is, for instance, provided in John Ashburner and Karl J Friston., Human Brain Function, Second edition, Academic Press 2004, Section 1, Chapter 6.3, pages 8 to 13, ISBN: 9780080472959; Moo K Chung., Computational Neuroanatomy, World Scientific 2012, Chapter 3, Pages 49 to 68, ISBN: 9789814472814. doi.org/10.1142/8036; and Thomson et al., Ann N Y Acad. Sci. 2007 February; 1097: 183-214. doi:10.1196/annals.1379.017.

vMRI data was collected for the whole brain tissue and analysis was able to quantify volume changes in individual regions of brain tissue. The results for Group A indicate that brain tissue volume is increased in numerous individual regions of the brain, giving rise to an increase in whole brain volume, after 52 weeks of the treatment regime outlined above. Brain regions with increased volume were also found to overlap with those regions exhibiting increased neuronal connectivity, as determined by fMRI discussed above. Results for Patient conversely show evidence of brain atrophy and evidence of decreasing whole brain volume.

After 52 weeks of treatment, Group A showed increased mean volumes in at least the following brain regions: right accumbens area, left putamen, left entorhinal cortex, right putamen, right postcentral lobe, left pericalcarine lobe, right amygdala, left cuneus, and left lingual, as well as increased mean whole brain volume. These results are shown in the table below.

| Brain Region | Group A mean change in volume (mm$^3$) from Baseline to Week 52 | Group A Standard Deviation | Patient 5 change in volume (mm$^3$) from Baseline to Week 52 |
|---|---|---|---|
| Right Accumbens Area | +12.86 | 9.65 | −52.1 |
| Left Putamen | +94.70 | 78.68 | −51.7 |
| Left Entorhinal Cortex | +34.53 | 32.08 | +41.4 |
| Right Putamen | +97.84 | 100.78 | −63.1 |
| Right Postcentral Lobe | +91.66 | 99.96 | −63.4 |
| Left Pericalcarine Lobe | +18.46 | 22.00 | −29.2 |
| Right Amygdala | +60.78 | 74.88 | −63.4 |
| Left Cuneus | +37.16 | 46.19 | −23.9 |
| Left Lingual | +50.08 | 70.99 | −60.0 |

It was also found that in Group A the treatment regime led to an overall increase in whole brain tissue volume, whereas Patient 5 conversely experienced a decrease in whole brain volume, as can be seen from FIG. 1. Patient 5, who did not successfully undergo the treatment regime, exhibited a relatively severe decrease in whole brain volume, as well as volume reductions in the majority of the above described individual brain regions. These results indicate that the treatment regime not only increased brain tissue volume in Group A, but also prevented and/or delayed the potential loss of brain tissue volume in Group A as a result of GD3 disease progression, as exhibited in Patient 5.

Example 6: Pharmacokinetics of Compound 2 in Healthy Human Volunteers

Two Phase 1 clinical studies were conducted to assess the pharmacokinetics, pharmacodynamics, safety, and tolerability of Compound 2 in healthy, human volunteers in the presence and absence of food. Compound 2 is also known as venglustat.

Study 1

Study 1 was a 2-part single-center trial in healthy adult male volunteers. Part 1 was a double-blind, randomized, placebo-controlled sequential ascending single-dose study of Compound 2 for safety, tolerability, and PK. Part 2 was an open-label, single-cohort, randomized, 2-sequence, 2-period, 2-treatment crossover study of Compound 2 for PK with and without a high-fat meal.

Part 1 of the study enrolled and randomized 55 healthy men (placebo, n=14; 2-, 5-, 15, 25-, 50, and 100-mg doses, n=6 each; 150-mg dose, n=5). Eight healthy men participated in Part 2.

In Part 1, the subjects were randomized to receive 2, 5, 15, 25, 50, 100, or 150 mg of Compound 2 (L-malic salt form, i.e., expressed under L-malic salt form) or matching placebo on the morning of the first day after at least a 10-hour fast. In Part 2, the subjects were randomized to receive a single oral dose of 5 mg Compound 2 either while fasting (at least 10 hours before and 4 hours after administration) or 30 minutes after a standardized high-fat breakfast (~815 kcal). After a 7-day washout period, participants were crossed over to the other condition.

In Study 1, Part 1, blood was sampled for plasma concentrations of Compound 2 at the time of study drug administration (0 hour) and 0.5, 1, 2, 3, 4, 5, 6, 8, 10, 12, 16, 24, 48, 72, and 96 hours post-dose. Urine samples were collected for analysis of Compound 2 concentrations beginning 2 hours before study drug administration through 48 hours afterward.

In Study 1, Part 2, blood was sampled for plasma concentrations if Compound 2 at 0, 0.5, 1, 2, 3, 4, 5, 6, 8, 10, 12, 16, 24, and 48 hours post-dose.

From Part 1, it was found that following single oral doses of 2 to 150 mg doses of Compound 2, maximal plasma concentration ($C_{max}$) occurred at a median time of 3-5.5 hours before plasma concentrations began to decline exponentially, with a geometric mean $t_{1/2}$ of 28.9 hours. Exposure increased close to dose-proportionally throughout the dose range: a 75-fold dose increase resulted in 97.3-, 89.2-, and 85.9-fold increases in geometric mean $C_{max}$, $AUC_{last}$, and $AUC_{inf}$ values, respectively. PK results are shown in the following table (AUC=area under the time concentration curve, either to last measurable concentration or extrapolated to infinity; $t_{1/2}$=terminal half-life; CL/F=apparent total clearance from plasma; CV=coefficient of variation; SD=standard deviation; $t_{max}$=time to $C_{max}$; Vss/F=apparent volume of distribution at steady state):

respectively. Within-subject variability (i.e., fed vs fasted) accounted for less than half the total subject variability.

Study 2

Study 2 was a single-center, double-blind, randomized, placebo-controlled, sequential ascending repeated-dose study of the safety, tolerability, PK, and pharmacodynamics of Compound 2 in healthy adult male and female volunteers.

The study enrolled and randomized 36 healthy adults (19 men and 17 women) (n=9 each to group). The subjects were randomized to receive once-daily doses of Compound 2 at 5, 10, or 20 mg (provided as 5-mg capsules of the L-malic salt form) or placebo for 14 days after at least a 10-hour fast.

Blood was sampled for plasma concentrations of Compound 2 as follows: Day 1 at 0, 0.5, 1, 2, 3, 4, 5, 6, 8, 10, 12, and 16 hours post-dose; On Days 2-5, 8, 11, and 13, at 0 h; On Day 14, at 0.5, 1, 2, 3, 4, 5, 6, 8, 10, and 12 hours post-dose; On Days 15-17, at 24, 48, and 72 hours, respectively, after the Day 14 dose. Urine samples were collected for analysis of Compound 2 concentrations on Day 1 (0 hours post-dose) and continuously on Day 14 from 0-24 hours post-dose. Pharmacodynamic endpoints (plasma GL-1, GL-3, and GM3 concentrations) were assessed on Days 1-5, 8, 11, 13, and 14, at 0 hours post-dose; and on Day 15, at 24 hours after the Day 14 dose.

It was found that in subjects receiving 5, 10, or 20 mg of Compound 2 once daily for 14 days, plasma $C_{max}$ occurred at a median time of 2-5 hours post-dose on Days 1 and 14. $C_{trough}$ values reached a plateau after Day 5. Compound 2

| Parameter | 2 mg (N = 6) | 5 mg (N = 6) | 15 mg (N = 6) | 25 mg (N = 6) | 50 mg (N = 6) | 100 mg (N = 6) | 150 mg (N = 5) |
|---|---|---|---|---|---|---|---|
| $C_{max}$, ng/ml | | | | | | | |
| Mean (SD) | 5.7 (1.2) | 14.7 (1.61) | 53.0 (16.7) | 84.4 (31.8) | 181 (56) | 374 (38) | 529 (109) |
| Geometric mean (CV) | 5.6 (21.4) | 14.6 (10.9) | 50.7 (31.5) | 79.9 (37.7) | 173 (31) | 372 (10.3) | 520 (21) |
| $t_{max}$, median h (range) | 3.50 (3.00-8.00) | 5.50 (4.00-8.00) | 3.50 (2.00-5.00) | 5.00 (4.00-8.00) | 4.00 (3.00-6.00) | 3.00 (2.00-4.00) | 4.00 (1.00-8.00) |
| $AUC_{last}$, ng · h/mL | | | | | | | |
| Mean (SD) | 214 (52) | 560 (71) | 1,830 (520) | 3,380 (1100) | 6,310 (1880) | 13,000 (2330) | 18,600 (5480) |
| Geometric mean (CV) | 209 (24.3) | 556 (12.7) | 1,760 (29) | 3,240 (33) | 6,070 (30) | 12,800 (18) | 18,000 (30) |
| $AUC_{inf}$, ng · h/mL | | | | | | | |
| Mean (SD) | 243 (61) | 652 (122) | 2,070 (600) | 3,810 (1,080) | 7,130 (2,320) | 14,400 (3,010) | 20,600 (6,640) |
| Geometric mean (CV) | 237 (25) | 643 (19) | 1,990 (29) | 3,690 (28) | 6,800 (33) | 14,100 (21) | 19,900 (32) |
| $t_{1/2}$, h | | | | | | | |
| Mean (SD) | 29.2 (43) | 33.3 (8.1) | 29.7 (7.1) | 30.2 (5.5) | 28.9 (5.3) | 27.8 (3.6) | 26.9 (5.7) |
| Geometric mean (CV) | 28.9 (14.8) | 32.5 (24.4) | 29.0 (24.0) | 29.8 (18.1) | 28.5 (18.4) | 27.6 (12.8) | 26.4 (21.3) |
| CL/F, L/h | | | | | | | |
| Mean (SD) | 6.43 (1.41) | 5.86 (1.01) | 5.85 (1.89) | 5.18 (1.31) | 5.75 (2.01) | 5.38 (1.25) | 5.80 (1.55) |
| Geometric mean (CV) | 6.3 (22.0) | 5.8 (17.3) | 5.6 (32.2) | 5.0 (25.3) | 5.5 (34.9) | 5.3 (23.4) | 5.6 (26.7) |
| $V_{ss}$/F, L | | | | | | | |
| Mean (SD) | 275 (54) | 274 (30) | 245 (81) | 240 (78) | 239 (62) | 213 (22) | 228 (50) |
| Geometric mean (CV) | 270 (20) | 273 (11) | 233 (33) | 228 (33) | 232 (26) | 212 (10) | 223 (22) |

From Part 2, it was found that administration of a 5 mg dose with a high-fat meal had no effect on Compound 2 exposure compared with fasting conditions. Median $t_{max}$ was 6.00 hours whether fed or fasting. Fed/fasted geometric mean ratios were 0.92 and 0.91 for $C_{max}$ and $AUC_{last}$, exposure increased close to dose-proportionally over the dose range of 5-20 mg: this 4-fold dose increase resulted in 3.76- and 3.69-fold increases in geometric mean $C_{max}$ and $AUC_{0-24}$ values on Day 14, respectively. PK results from Study 2 are summarized in the following table:

| Parameter | 5 mg (N = 9) | 10 mg (N = 9) | 20 mg (N = 9) |
|---|---|---|---|
| Day 1 | | | |
| $C_{max}$, ng/ml | | | |
| Mean (SD) | 18.5 (3.2) | 38.5 (7.4) | 68.0 (15.7) |
| Geometric mean (CV) | 18.2 (17.3) | 37.8 (19.3) | 66.5 (23.1) |
| $t_{max}$, median h (range) | 5.00 (2.00-8.17) | 3.00 (2.00-5.00) | 3.07 (2.00-6.00) |
| $AUC_{0-24}$, ng · h/mL | | | |
| Mean (SD) | 296 (54) | 635 (132) | 1,100 (211) |
| Geometric mean (CV) | 292 (18) | 623 (21) | 1,080 (19) |
| Day 14 | | | |
| $C_{max}$, ng/ml | | | |
| Mean (SD) | 37.0 (6.4) | 89.7 (29.1) | 142 (40) |
| Geometric mean (CV) | 36.5 (17.2) | 86.0 (32.5) | 137 (28.3) |
| $t_{max}$, median h (range) | 3.00 (2.00-6.00) | 2.00 (2.00-6.00) | 3.00 (2.00-8.00) |
| $AUC_{0-24}$, ng · h/mL | | | |
| Mean (SD) | 642 (121) | 1,550 (464) | 2,420 (705) |
| Geometric mean (CV) | 632 (19) | 1,490 (30) | 2,340 (29) |
| $C_{trough}$, ng/ml | | | |
| Mean (SD) | 19.4 (4.0) | 49.9 (19.3) | 73.3 (24.4) |
| Geometric mean (CV) | 19.0 (20.5) | 47.5 (38.7) | 69.9 (33.2) |
| $t_{1/2}$, h | | | |
| Mean (SD) | 29.3 (4.6) | 31.3 (3.3) | 35.0 (6.3) |
| Geometric mean (CV) | 29.0 (15.8) | 31.2 (10.5) | 34.5 (18.0) |
| $CL_{ss}/F$, L/h | | | |
| Mean (SD) | 5.98 (1.17) | 5.13 (1.25) | 6.58 (1.70) |
| Geometric mean (CV) | 5.9 (19.5) | 5.0 (24.4) | 6.4 (25.8) |
| $CL_{R(0-24)}$, L/h | | | |
| Mean (SD) | 1.55 (0.68) | 1.49 (0.41) | 2.07 (0.58) |
| Geometric mean (CV) | $NA^a$ (44.0) | 1.4 (27.7) | 2.0 (28.0) |

After 14 once-daily doses of Compound 2, its 24-hour unchanged urinary excretion fraction (mean $fe_{0-24}$) ranged between 26.3% and 33.1% without any obvious dose-relatedness. Mean $CL_{R(0-24)}$ ranged between 1.49 L/h and 2.07 L/h, approximately 3.18-3.86-fold lower than observed plasma CL/F.

Plasma GL-1, GL-3, and GM3 in placebo recipients remained similar to baseline throughout, whereas plasma GL-1 and GM3 levels decreased from baseline time- and dose-dependently across the 3 Compound 2 dose groups, as shown in the following table (Point estimates of treatment ratios for glucosylceramide (GL-1), globotriaosylceramide (GL-3), and GM3 ganglioside (GM3) on Day 15 in the repeated ascending dose study):

| Parameter | Comparison | Estimate | 90% Confidence Interval |
|---|---|---|---|
| GL-1 | 5 mg vs placebo | 0.39 | 0.29-0.50 |
| | 10 mg vs placebo | 0.32 | 0.25-0.42 |
| | 20 mg vs placebo | 0.23 | 0.17-0.30 |
| GL-3 | 5 mg vs placebo | 0.61 | 0.47-0.79 |
| | 10 mg vs placebo | 0.69 | 0.53-0.89 |
| | 20 mg vs placebo | 0.67 | 0.51-0.89 |
| GM3 | 5 mg vs placebo | 0.56 | 0.45-0.70 |
| | 10 mg vs placebo | 0.49 | 0.39-0.60 |
| | 20 mg vs placebo | 0.40 | 0.32-0.50 |

Maximal sustained effects on GL-1 occurred on Day 11 in the 5- and 10-mg groups and by Day 8 in the 20-mg group. Mean calculated GL-1 reductions from baseline at Day 15 were 41.9%, 69.6%, and 74.6% in the respective 5-, 10-, and 20-mg groups. GL-1 values were below the lower limit quantification (LLOQ) at baseline in 15-mg Compound 2 recipient and at Day 15 in 3, 5, and 9 subjects in the 5-, 10-, and 20-mg groups, respectively.

Maximal sustained GM3 decreases occurred across all Compound 2 dose groups starting on Day 13. Mean Day 15 plasma GM3 levels were 42.7%, 49.4%, and 57.8% of baseline for the 5-, 10-, and 20-mg dose groups, respectively. GM3 was below the LLOQ at Day 15 in 1 and 2 subjects in the 10- and 20-mg dose groups, respectively.

Plasma GL-3 also decreased with time in all Compound 2 dose groups, but variable and low baseline GL-3 values relative to LLOQ limited mean calculated GL-3 reductions. In the placebo, 5-, 10-, and 20-mg dose groups, GL-3 values were below LLOQ in 1, 3, 1, and 6 subjects, respectively, at baseline and in 4, 9, 7, and 9 subjects, respectively, at Day 15.

Mean estimated plasma GL-1 reductions from baseline (90% CI) attributable to Compound 2 $C_{trough}$ in the 5, 10, and 20 mg dose groups (19.0, 47.5, and 69.9 ng/mL, respectively) were 67.0% (54.4-79.7%), 74.4% (63.7-85.2%), and 76.3% (64.8-87.8%), respectively.

CONCLUSIONS

In these studies, Compound 2 exposure in healthy subjects ($C_{max}$ and AUC) was close-to-dose-proportional when administered as single doses ranging from 2-150 mg or as repeated, once-daily dosings ranging from 5-20 mg for 14 days. Compared with fasting, a high-fat meal had no effect on exposure in subjects who received a single 5-mg dose. With repeated once-daily doses from 5-20 mg, steady state was achieved within 5 days; neither age nor gender affected accumulation. Pharmacodynamically, repeated once-daily doses of Compound 2 reduced plasma concentrations of GL-1 and GM3 in a time- and dose-dependent manner, consistent with Compound 2-mediated GCS inhibition, although baseline levels of GL-3 were too low to be useful as a pharmacodynamic biomarker. The dose-dependent GL-1 reduction corroborated the intended mechanism of action of Compound 2: inhibition of GL-1 formation from ceramide by GCS.

In all studies, safety profile was assessed by monitoring treatment-emergent adverse events (TEAEs) through 10 days after last dose of study medication, including serious adverse events [SAEs]), ECG monitoring, laboratory values, and physical examinations. There were no deaths, SAEs, severe TEAEs, or TEAEs leading to study discontinuation in any of the studies.

No clinically relevant hematologic or biochemical abnormalities were reported in any of the studies. Vital signs showed no relevant changes from baseline in any of the studies. ECG parameters showed no relevant changes in the single ascending dose and food effect studies; in the multiple ascending dose study no ECG parameters changed statistically significantly from average baseline versus placebo in recipients of Compound 2 at any dose. It is to be understood that while the invention has been described in conjunction with the above embodiments, that the foregoing description and examples are intended to illustrate and not limit the scope of the invention. Other aspects, advantages, and modifications within the scope of the invention will be apparent to those skilled in the art to which the invention pertains.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed:

1. A method for increasing brain tissue volume, or preventing or delaying loss of brain tissue volume, in a human subject in need thereof, wherein said subject has a lysosomal storage disease and a brain tissue volume which is lower than a reference standard, wherein the subject has a lower brain tissue volume in one or more brain regions where loss of neuronal connectivity is assessed to be present in comparison to the reference standard, said method comprising administering to the subject an effective amount of a compound of formula (I),

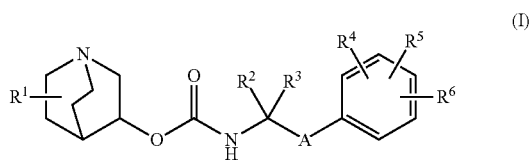

or a pharmaceutically acceptable salt or prodrug thereof, wherein:
   $R^1$ is selected from hydrogen, halogen, cyano, nitro, hydroxy, thio, amino, $C_{1-6}$-alkyl, $C_{2-6}$-alkenyl, $C_{2-6}$-alkynyl, $C_{1-6}$-alkyloxy, $C_{2-6}$-alkenyloxy, and $C_{2-6}$-alkynyloxy, wherein said alkyl, alkenyl, alkynyl, alkyloxy, alkenyloxy, or alkynyloxy is optionally substituted with one or more groups selected from halogen, cyano, nitro, hydroxy, thio, and amino;
   $R^2$ and $R^3$ are independently selected from $C_{1-3}$-alkyl, optionally substituted by one or more halogens, or $R^2$ and $R^3$ together form a cyclopropyl or cyclobutyl group, optionally substituted by one or more halogens;
   $R^4$, $R^5$ and $R^6$ are each independently selected from hydrogen, halogen, nitro, hydroxy, thio, amino, $C_{1-6}$-alkyl, and $C_{1-6}$-alkyloxy, wherein said alkyl or alkyloxy is optionally substituted by one or more groups selected from halogen, hydroxy, cyano, and $C_{1-6}$-alkyloxy; and
   A is a 5- or 6-membered aryl or heteroaryl group, optionally substituted with 1, 2, or 3 groups independently selected from halogen, hydroxy, thio, amino, nitro, $C_{1-6}$-alkoxy, and $C_{1-6}$-alkyl.

2. The method of claim 1, wherein the subject has a lower whole brain tissue volume in comparison to the reference standard.

3. The method of claim 1, wherein the method results in an increase in brain tissue volume, or prevention or delay in loss of brain tissue volume, in one or more brain regions selected from: right accumbens, left putamen, left entorhinal cortex, right putamen, right postcentral lobe, left pericalcarine, right amygdala, left cuneus and left lingual.

4. The method of claim 1, wherein the method results in an increase in brain tissue volume, or prevention or delay in loss of brain tissue volume, in one or more brain regions selected from: right accumbens, left putamen, left entorhinal cortex, right putamen, right postcentral lobe, left pericalcarine, right amygdala, left cuneus, and left lingual, as measured using volumetric magnetic resonance imaging (vMRI).

5. The method of claim 1, wherein the increase in brain tissue volume is at least 5 mm$^3$, in one or more brain regions.

6. The method of claim 1, wherein the increase in whole brain tissue volume is at least 5 mm$^3$.

7. The method of claim 1, wherein the method results in increased brain volume in one or more brain regions associated with executive function.

8. The method of claim 1, wherein the increase in brain volume is accompanied by an enhancement in neuronal connectivity.

9. The method of claim 1, wherein the method results in an increase in the whole brain tissue volume.

10. The method of claim 1, wherein the subject has Gaucher disease Type 3.

11. The method of claim 1, wherein said compound is selected from: quinuclidin-3-yl (2-(4'-fluoro-[1,1'-biphenyl]-3-yl)propan-2-yl)carbamate), (S)-quinuclidin-3-yl (2-(2-(4-fluorophenyl)thiazol-4-yl)propan-2-yl)carbamate, and (S)-quinuclidin-3-yl (2-(4'-(2-methoxyethoxy)-[1,1'-biphenyl]-4-yl)propan-2-yl)carbamate, or a pharmaceutically acceptable salt or prodrug thereof.

12. The method of claim 1, wherein said compound is quinuclidin-3-yl (2-(4'-fluoro-[1,1'-biphenyl]-3-yl)propan-2-yl)carbamate.

13. The method of claim 1, wherein said compound is (S)-quinuclidin-3-yl (2-(2-(4-fluorophenyl)thiazol-4-yl)propan-2-yl)carbamate.

14. The method of claim 1, wherein said compound is (S)-quinuclidin-3-yl (2-(2-(4-fluorophenyl)thiazol-4-yl)propan-2-yl)carbamate in malate salt form.

15. The method of claim 1, wherein said compound, or pharmaceutically acceptable salt or prodrug thereof, is administered by systemic administration.

16. The method of claim 1, wherein said compound, or pharmaceutically acceptable salt or prodrug thereof, is administered orally.

17. The method of claim 1, wherein the subject undergoes concurrent treatment with enzyme replacement therapy (ERT).

18. The method of claim 1, wherein the subject is administered a daily dose of about 1 mg to about 50 mg of the compound.

19. The method of claim 1, wherein the subject is administered a single daily dose of 15 mg (measured as the quantity of free base) of (S)-quinuclidin-3-yl (2-(2-(4-fluorophenyl)thiazol-4-yl)propan-2-yl)carbamate in malate salt form.

20. A method for increasing brain tissue volume, or preventing or delaying loss of brain tissue volume, in a human subject in need thereof, wherein said subject has a lysosomal storage disease and a brain tissue volume which is lower than a reference standard, wherein the subject has a lower brain tissue volume in one or more brain regions selected from: right accumbens, left putamen, left entorhinal cortex, right putamen, right postcentral lobe, left pericalcarine, right amygdala, left cuneus, and left lingual in comparison to the reference standard, said method comprising administering to the subject an effective amount of a compound of formula (I),

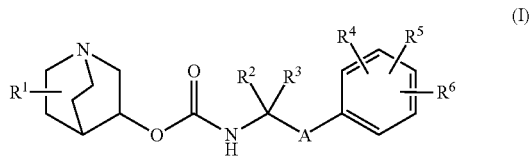

or a pharmaceutically acceptable salt or prodrug thereof, wherein:
- $R^1$ is selected from hydrogen, halogen, cyano, nitro, hydroxy, thio, amino, $C_{1-6}$-alkyl, $C_{2-6}$-alkenyl, $C_{2-6}$-alkynyl, $C_{1-6}$-alkyloxy, $C_{2-6}$-alkenyloxy, and $C_{2-6}$-alkynyloxy, wherein said alkyl, alkenyl, alkynyl, alkyloxy, alkenyloxy, or alkynyloxy is optionally substituted with one or more groups selected from halogen, cyano, nitro, hydroxy, thio, and amino;
- $R^2$ and $R^3$ are independently selected from $C_{1-3}$-alkyl, optionally substituted by one or more halogens, or $R^2$ and $R^3$ together form a cyclopropyl or cyclobutyl group, optionally substituted by one or more halogens;
- $R^4$, $R^5$, and $R^6$ are each independently selected from hydrogen, halogen, nitro, hydroxy, thio, amino, $C_{1-6}$-alkyl, and $C_{1-6}$-alkyloxy, wherein said alkyl or alkyloxy is optionally substituted by one or more groups selected from halogen, hydroxy, cyano, and $C_{1-6}$-alkyloxy; and
- A is a 5- or 6-membered aryl or heteroaryl group, optionally substituted with 1, 2, or 3 groups independently selected from halogen, hydroxy, thio, amino, nitro, $C_{1-6}$-alkoxy, and $C_{1-6}$-alkyl.

21. The method of claim 20, wherein the subject is administered a single daily dose of 15 mg (measured as the quantity of free base) of (S)-quinuclidin-3-yl (2-(2-(4-fluorophenyl)thiazol-4-yl)propan-2-yl)carbamate in malate salt form.

22. The method of claim 20, wherein the method results in an increase in brain tissue volume, or prevention or delay in loss of brain tissue volume, in one or more brain regions selected from: right accumbens, left putamen, left entorhinal cortex, right putamen, right postcentral lobe, left pericalcarine, right amygdala, left cuneus and left lingual.

23. The method of claim 20, wherein the method results in increased brain volume in one or more brain regions associated with executive function.

24. The method of claim 20, wherein the increase in brain volume is accompanied by an enhancement in neuronal connectivity.

25. The method of claim 20, wherein the method results in an increase in the whole brain tissue volume.

26. The method of claim 20, wherein the subject has Gaucher disease Type 3.

27. The method of claim 20, wherein said compound, or pharmaceutically acceptable salt or prodrug thereof, is administered orally.

28. The method of claim 20, wherein the subject undergoes concurrent treatment with enzyme replacement therapy (ERT).

29. A method for increasing brain tissue volume, or preventing or delaying loss of brain tissue volume, in a human subject in need thereof, wherein said subject has a lysosomal storage disease and a brain tissue volume which is lower than a reference standard, wherein the subject has a lower brain tissue volume in one or more brain regions associated with executive function in comparison to the reference standard, said method comprising administering to the subject an effective amount of a compound of formula (I),

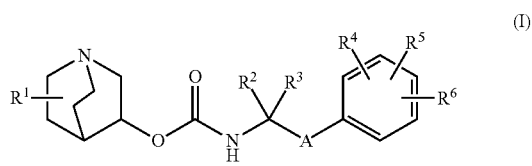

or a pharmaceutically acceptable salt or prodrug thereof, wherein:
- $R^1$ is selected from hydrogen, halogen, cyano, nitro, hydroxy, thio, amino, $C_{1-6}$-alkyl, $C_{2-6}$-alkenyl, $C_{2-6}$-alkynyl, $C_{1-6}$-alkyloxy, $C_{2-6}$-alkenyloxy, and $C_{2-6}$-alkynyloxy, wherein said alkyl, alkenyl, alkynyl, alkyloxy, alkenyloxy, or alkynyloxy is optionally substituted with one or more groups selected from halogen, cyano, nitro, hydroxy, thio, and amino;
- $R^2$ and $R^3$ are independently selected from $C_{1-3}$-alkyl, optionally substituted by one or more halogens, or $R^2$ and $R^3$ together form a cyclopropyl or cyclobutyl group, optionally substituted by one or more halogens;
- $R^4$, $R^5$, and $R^6$ are each independently selected from hydrogen, halogen, nitro, hydroxy, thio, amino, $C_{1-6}$-alkyl, and $C_{1-6}$-alkyloxy, wherein said alkyl or alkyloxy is optionally substituted by one or more groups selected from halogen, hydroxy, cyano, and $C_{1-6}$-alkyloxy; and
- A is a 5- or 6-membered aryl or heteroaryl group, optionally substituted with 1, 2, or 3 groups independently selected from halogen, hydroxy, thio, amino, nitro, $C_{1-6}$-alkoxy, and $C_{1-6}$-alkyl.

30. The method of claim 29, wherein said compound, or pharmaceutically acceptable salt or prodrug thereof, is administered orally.

31. The method of claim 29, wherein the subject undergoes concurrent treatment with enzyme replacement therapy (ERT).

32. The method of claim 29, wherein the subject is administered a single daily dose of 15 mg (measured as the quantity of free base) of (S)-quinuclidin-3-yl (2-(2-(4-fluorophenyl)thiazol-4-yl)propan-2-yl)carbamate in malate salt form.

33. The method of claim 29, wherein the method results in an increase in brain tissue volume, or prevention or delay in loss of brain tissue volume, in one or more brain regions selected from: right accumbens, left putamen, left entorhinal cortex, right putamen, right postcentral lobe, left pericalcarine, right amygdala, left cuneus and left lingual.

34. The method of claim 29, wherein the method results in increased brain volume in one or more brain regions associated with executive function.

35. The method of claim 29, wherein the increase in brain volume is accompanied by an enhancement in neuronal connectivity.

36. The method of claim 29, wherein the method results in an increase in the whole brain tissue volume.

37. The method of claim 29, wherein the subject has Gaucher disease Type 3.

* * * * *

UNITED STATES PATENT AND TRADEMARK OFFICE
CERTIFICATE OF CORRECTION

PATENT NO. : 12,083,115 B2
APPLICATION NO. : 17/166863
DATED : September 10, 2024
INVENTOR(S) : Crawford et al.

It is certified that error appears in the above-identified patent and that said Letters Patent is hereby corrected as shown below:

In the Specification

Column 23, Line 55, "(Ixa) and (Ixb)" should be changed to "(IXa) and (IXb)"

Column 24, Line 35, "S" should be changed to "$^{32}S$"

Column 27, Line 67, "g/mL" should be changed to "μg/mL"

Column 28, Line 19-20, "from 18 to years old" should be changed to "from 18 to 40 years old"

Column 33, Line 9, "g/mL" should be changed to "μg/mL"

Column 33, Line 27-28, "from 18 to years old" should be changed to "from 18 to 40 years old"

Column 38, Line 12, "g/mL" should be changed to "μg/mL"

Column 38, Line 30-31, "from 18 to years old" should be changed to "from 18 to 40 years old"

Column 43, Line 52, "pg/mL" should be changed to "μg/mL"

Column 44, Line 3-4, "from 18 to years old" should be changed to "from 18 to 40 years old"

Column 48, Line 16, "pg/mL" should be changed to "μg/mL"

Column 48, Line 23-24, "from 18 to years old" should be changed to "from 18 to 40 years old"

Column 50, Line 50, ">12.0 g/dL" should be changed to "≥12.0 g/dL"

Column 59, Line 18, "2.OM" should be changed to "2.0M"

Signed and Sealed this
Thirty-first Day of December, 2024

Derrick Brent
*Acting Director of the United States Patent and Trademark Office*

CERTIFICATE OF CORRECTION (continued)
U.S. Pat. No. 12,083,115 B2

Column 59, Line 26, "4.OM" should be changed to "4.0M"

Column 60, Line 43, "(Compound" should be changed to "(Compound 1)"

Column 64, Line 23, "$NH_4C_1$" should be changed to "$NH_4Cl$"

Column 64, Line 43, "$NH_{40}H$" should be changed to "$NH_4OH$"

Column 73, Line 25, "5.OM" should be changed to "5.0M"

Column 75, Line 53, "$C_{o2}$" should be changed to "$CO_2$"

Column 79, Line 54, "100 000" should be changed to "≥100 000"

Column 79, Line 58, "≥3 years" should be changed to ">3 years"

In the Claims

Column 94, Line 33-34, Claim 11, "(2-(4'-fluoro-[1,1'-biphenyl]-3-yl)propan-2-yl)carbamate)" should be changed to "(2-(4'-fluoro-[1,1'-biphenyl]-3-yl)propan-2-yl)carbamate"